(12) United States Patent
Stypulkowski et al.

(10) Patent No.: US 8,706,181 B2
(45) Date of Patent: Apr. 22, 2014

(54) TARGET THERAPY DELIVERY SITE SELECTION

(75) Inventors: Paul H. Stypulkowski, North Oaks, MN (US); Jonathon E. Giftakis, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 13/358,179

(22) Filed: Jan. 25, 2012

(65) Prior Publication Data

US 2012/0191157 A1 Jul. 26, 2012

Related U.S. Application Data

(60) Provisional application No. 61/436,059, filed on Jan. 25, 2011.

(51) Int. Cl.
*A61B 5/04* (2006.01)
*A61N 1/00* (2006.01)

(52) U.S. Cl.
USPC ........... 600/378; 600/13; 600/544; 607/2; 607/45; 607/116

(58) Field of Classification Search
USPC ............. 600/13, 378, 544; 607/2, 45, 116
See application file for complete search history.

(56) References Cited

U.S. PATENT DOCUMENTS

| | | | |
|---|---|---|---|
| 5,978,702 A * | 11/1999 | Ward et al. | ........... 607/3 |
| 6,066,163 A | 5/2000 | John | |
| 6,263,237 B1 | 7/2001 | Rise | |
| 6,463,328 B1 | 10/2002 | John | |
| 6,622,036 B1 | 9/2003 | Suffin | |
| 6,671,555 B2 | 12/2003 | Gielen et al. | |
| 6,708,064 B2 | 3/2004 | Rezai | |
| 7,006,872 B2 | 2/2006 | Gielen et al. | |
| 7,024,247 B2 | 4/2006 | Gliner et al. | |
| 7,089,059 B1 | 8/2006 | Pless | |
| 7,231,245 B2 | 6/2007 | Greenwald et al. | |
| 7,242,983 B2 * | 7/2007 | Frei et al. | ........... 607/45 |
| 7,277,758 B2 | 10/2007 | DiLorenzo | |
| 7,353,064 B2 | 4/2008 | Gliner et al. | |

(Continued)

FOREIGN PATENT DOCUMENTS

| | | |
|---|---|---|
| WO | 0176469 A2 | 10/2001 |
| WO | 2008013722 A1 | 1/2008 |
| WO | 2009129486 A2 | 10/2009 |

OTHER PUBLICATIONS

International Search Report and the Written Opinion for corresponding PCT Application No. PCT/US2012/022558, (10 pgs.).

(Continued)

*Primary Examiner* — Niketa Patel
*Assistant Examiner* — Christopher A Flory
(74) *Attorney, Agent, or Firm* — Shumaker & Sieffert, PA

(57) ABSTRACT

In some examples of selecting a target therapy delivery site for treating a patient condition, a relatively high frequency electrical stimulation signal is delivered to at least two areas within a first region (e.g., an anterior nucleus of the thalamus) of a brain of a patient, and changes in brain activity (e.g., as indicated by bioelectrical brain signals) within a second region (e.g., a hippocampus) of the brain of the patient in response to the delivered stimulation are determined. The target therapy delivery site, an electrode combination, or both, may be selected based on the changes in brain activity.

48 Claims, 21 Drawing Sheets

(56) References Cited

U.S. PATENT DOCUMENTS

| | | | |
|---|---|---|---|
| 7,353,065 B2 | 4/2008 | Morrell | |
| 7,418,290 B2 | 8/2008 | Devlin et al. | |
| 7,532,935 B2* | 5/2009 | Maschino et al. | 607/45 |
| 7,623,927 B2* | 11/2009 | Rezai | 607/45 |
| 8,027,730 B2* | 9/2011 | John | 607/45 |
| 2001/0031993 A1 | 10/2001 | Salo et al. | |
| 2002/0013612 A1 | 1/2002 | Whitehurst | |
| 2002/0151939 A1* | 10/2002 | Rezai | 607/40 |
| 2003/0083724 A1 | 5/2003 | Jog et al. | |
| 2003/0181954 A1* | 9/2003 | Rezai | 607/45 |
| 2004/0093983 A1 | 5/2004 | Mishima et al. | |
| 2004/0111127 A1 | 6/2004 | Gliner | |
| 2004/0172091 A1* | 9/2004 | Rezai | 607/45 |
| 2005/0010262 A1* | 1/2005 | Rezai et al. | 607/46 |
| 2005/0043774 A1 | 2/2005 | Devlin et al. | |
| 2005/0065427 A1 | 3/2005 | Magill et al. | |
| 2005/0081847 A1 | 4/2005 | Lee et al. | |
| 2005/0216064 A1 | 9/2005 | Heruth et al. | |
| 2005/0216071 A1 | 9/2005 | Devlin et al. | |
| 2006/0058627 A1 | 3/2006 | Flaherty et al. | |
| 2006/0217781 A1* | 9/2006 | John | 607/45 |
| 2006/0259099 A1 | 11/2006 | Goetz et al. | |
| 2006/0264957 A1 | 11/2006 | Cragg et al. | |
| 2007/0027499 A1* | 2/2007 | Maschino et al. | 607/45 |
| 2007/0027500 A1 | 2/2007 | Maschino et al. | |
| 2007/0028212 A1 | 2/2007 | Meijer et al. | |
| 2007/0067001 A1* | 3/2007 | Lozano et al. | 607/42 |
| 2007/0100392 A1 | 5/2007 | Maschino et al. | |
| 2007/0123758 A1 | 5/2007 | Miesel et al. | |
| 2007/0129769 A1 | 6/2007 | Bourget et al. | |
| 2007/0142874 A1 | 6/2007 | John | |
| 2007/0150024 A1 | 6/2007 | Leyde et al. | |
| 2007/0161919 A1 | 7/2007 | DiLorenzo | |
| 2007/0167991 A1 | 7/2007 | DiLorenzo | |
| 2007/0173901 A1 | 7/2007 | Reeve | |
| 2007/0213785 A1 | 9/2007 | Osorio et al. | |
| 2007/0213786 A1 | 9/2007 | Sackellares et al. | |
| 2007/0265489 A1 | 11/2007 | Fowler et al. | |
| 2007/0265536 A1 | 11/2007 | Giftakis et al. | |
| 2007/0293901 A1 | 12/2007 | Rousso et al. | |
| 2008/0004660 A1 | 1/2008 | Assaf et al. | |
| 2008/0033502 A1 | 2/2008 | Harris et al. | |
| 2008/0046036 A1* | 2/2008 | King et al. | 607/59 |
| 2008/0058874 A1* | 3/2008 | Westlund et al. | 607/2 |
| 2008/0154332 A1* | 6/2008 | Rezai | 607/45 |
| 2008/0183097 A1 | 7/2008 | Leyde et al. | |
| 2008/0188906 A1* | 8/2008 | Barolat et al. | 607/46 |
| 2008/0249431 A1 | 10/2008 | Bier et al. | |
| 2008/0255632 A1* | 10/2008 | Rezai | 607/46 |
| 2008/0269631 A1 | 10/2008 | Denison et al. | |
| 2009/0082641 A1 | 3/2009 | Giftakis et al. | |
| 2009/0099627 A1 | 4/2009 | Molnar et al. | |
| 2009/0264957 A1 | 10/2009 | Giftakis et al. | |
| 2009/0264967 A1 | 10/2009 | Giftakis et al. | |
| 2010/0114237 A1* | 5/2010 | Giftakis et al. | 607/45 |
| 2010/0121213 A1 | 5/2010 | Giftakis et al. | |
| 2010/0121214 A1 | 5/2010 | Giftakis et al. | |
| 2010/0228310 A1* | 9/2010 | Shuros et al. | 607/17 |
| 2010/0256707 A1* | 10/2010 | Ridder | 607/57 |
| 2010/0324628 A1* | 12/2010 | Westlund et al. | 607/62 |
| 2011/0137371 A1 | 6/2011 | Giftakis et al. | |
| 2011/0307030 A1* | 12/2011 | John | 607/45 |

OTHER PUBLICATIONS

Erwin B. Montgomery, Jr., M.D., "Deep Brain Stimulation Programming," Feb. 20, 2006, 37 pages.

Wright et al., "Cortical excitability predicts seizures in acutely drug-reduced temporal lobe epilepsy patients," Neurology, 2006;67:1646-1651 (downloaded on Oct. 21, 2010).

* cited by examiner

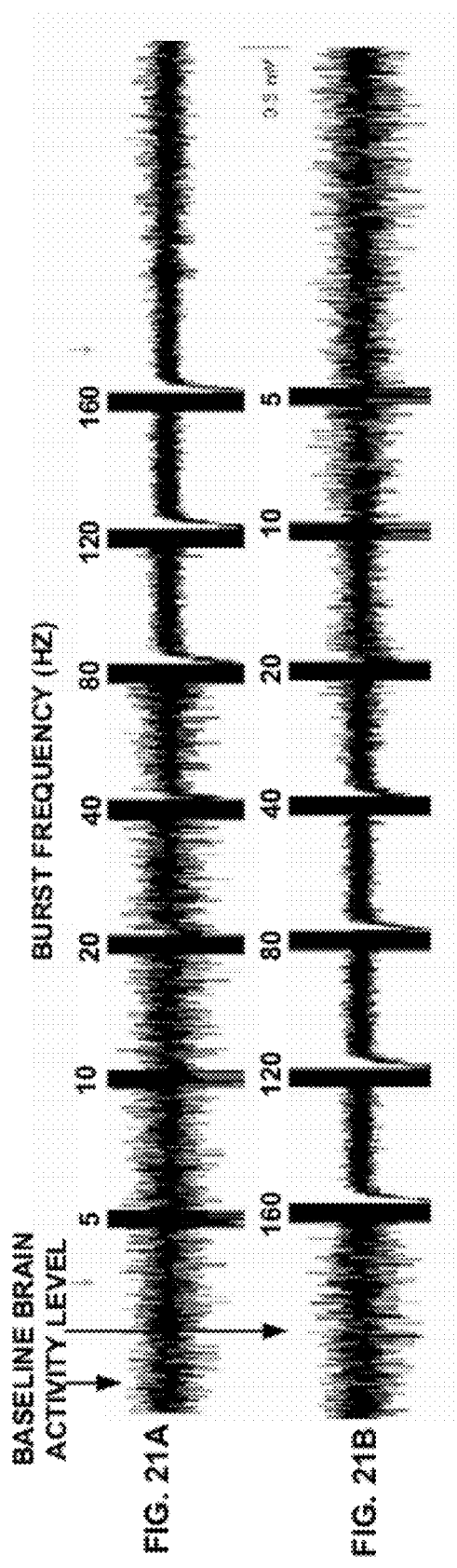
FIG. 21A
FIG. 21B
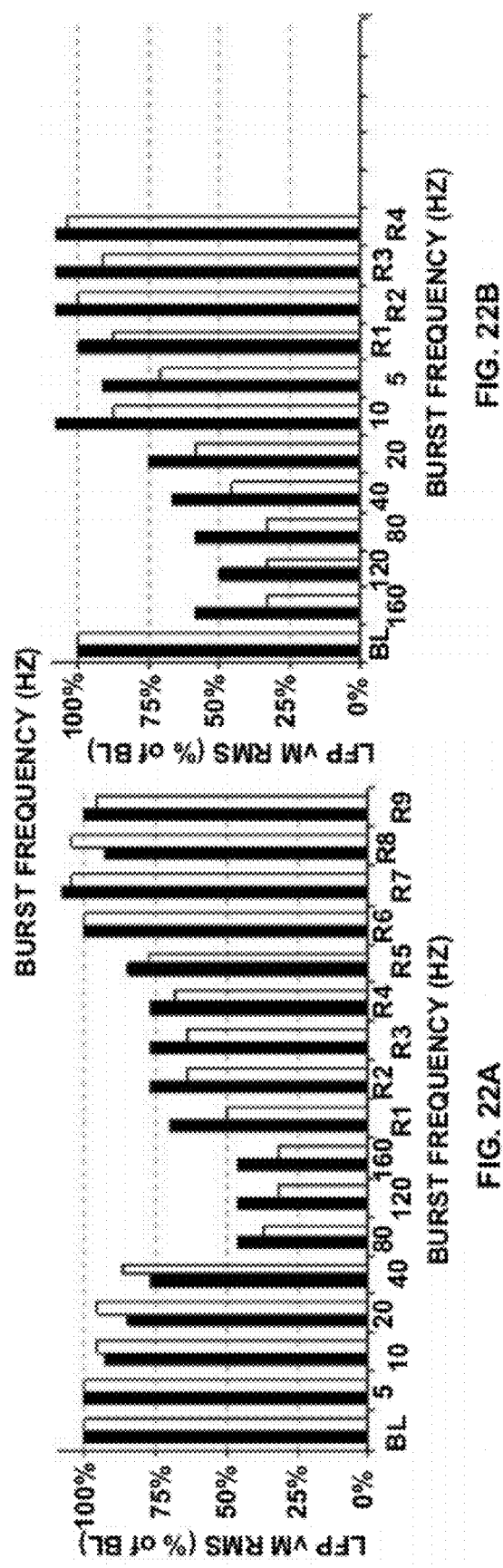
FIG. 22A
FIG. 22B

TARGET THERAPY DELIVERY SITE SELECTION

This application claims the benefit of U.S. Provisional Application Ser. No. 61/436,059 by Stypulkowski et al., which was filed on Jan. 25, 2011, and is entitled "TARGET THERAPY DELIVERY SITE ELECTION." U.S. Provisional Application Ser. No. 61/436,059 by Stypulkowski et al. is incorporated herein by reference in its entirety

TECHNICAL FIELD

The disclosure relates to medical devices and, more particularly, to the selection of a target therapy delivery site.

BACKGROUND

Implantable medical devices, such as electrical stimulators or therapeutic agent delivery devices, may be used in different therapeutic applications, such as deep brain stimulation (DBS) or the delivery of pharmaceutical agent to a target tissue site within a patient. A medical device may be used to deliver therapy to a patient to treat a variety of symptoms or patient conditions such as chronic pain, tremor, Parkinson's disease, other types of movement disorders, seizure disorders (e.g., epilepsy), obesity or mood disorders. In some therapy systems, an external or implantable electrical stimulator delivers electrical therapy to a target tissue site within a patient with the aid of one or more implanted electrodes, which may be deployed by medical leads or on a housing of the stimulator. In addition to, or instead of, electrical stimulation therapy, a medical device may deliver a therapeutic agent to a target tissue site within a patient with the aid of one or more fluid delivery elements, such as a catheter or a therapeutic agent eluting patch.

SUMMARY

In general, the disclosure relates to devices, systems, and methods for selecting a target therapy delivery site in a patient for treating a patient condition, such as a seizure disorder (e.g., epilepsy). In some examples, a target therapy delivery site is selected based on the functional connectivity between an area of an anterior nucleus of a thalamus (referred to herein as the "anterior nucleus" or the "AN") of a brain of a patient and a hippocampus (HC) of the brain. Functional connectivity may be characterized by the effect of electrical stimulation delivery to an area of the AN on the brain activity level within the HC. Delivery of stimulation to different areas within the AN may have different effects on the level of brain activity within the HC. Thus, in some examples, the target therapy delivery site within the AN is selected by delivering stimulation to different areas within the AN and determining the level of brain activity within the HC resulting from the delivery of stimulation to each of the respective areas within the AN. In this way, the functional connections between different areas of the AN and the HC are mapped. The target therapy delivery site can be selected to be the area within the AN that is associated with a desirable level of brain activity (e.g., a determined brain activity level or a change in the brain activity level) within the HC. The level of brain activity within the HC can be determined based on, for example, a bioelectrical brain signal sensed within the AN and/or a bioelectrical brain signal sensed within the HC after delivering stimulation to an area of the AN.

In some examples, an electrode combination with which electrical stimulation therapy is delivered to the brain of the patient or with which electrical activity is sensed within the brain may be selected based on the mapping of the functional connections between different areas of the AN and the HC.

In one example, the disclosure is directed to a method comprising, controlling a medical device to deliver electrical stimulation to a plurality of different areas of an AN of a thalamus of a brain of a patient, wherein the electrical stimulation comprises a frequency greater than or equal to about 80 Hertz, and wherein the electrical stimulation is delivered to each area of the plurality of different areas of the AN at a different time. The method further comprises, for each area of the plurality of different areas of the AN of the thalamus, determining a level of brain activity in a HC of the brain of the patient resulting from the delivery of the electrical stimulation to the area of the AN, and selecting at least one of the areas of the AN of the thalamus of the brain of the patient as a target therapy delivery site based on the associated level of brain activity in the HC of the brain.

In another example, the disclosure is directed to a system comprising a stimulation generator configured to generate and deliver electrical stimulation, a sensing module configured to sense a bioelectrical brain signal of the patient, and a processor configured to control the stimulation generator to deliver electrical stimulation to each area of a plurality of different areas of an AN of a thalamus of a brain of a patient at a different time, wherein the electrical stimulation comprises a frequency greater than or equal to about 80 Hertz. The processor is further configured to determine, for each area of the plurality of different areas of the AN or the thalamus, a level of brain activity in a HC of the brain of the patient resulting from the delivery of the electrical stimulation to the area based on the bioelectrical brain signal, and selects at least one of the areas of the AN of the thalamus of the brain of the patient as a target therapy delivery site based on the associated level of brain activity in the HC of the brain.

In another example, the disclosure is directed to a system comprising means for delivering electrical stimulation to a brain of a patient and means for controlling the means for delivering electrical stimulation to deliver electrical stimulation to each area of a plurality of different areas of an AN of a thalamus of the brain at a different time, wherein the electrical stimulation comprises a frequency greater than or equal to about 80 Hertz. The system further comprises means for determining, for each area of the plurality of different areas of the AN of the thalamus, a level of brain activity in a HC of the brain of the patient resulting from the delivery of the electrical stimulation to the area, and means for selecting at least one of the areas of the AN of the thalamus of the brain of the patient as a target therapy delivery site based on the associated level of brain activity in the HC of the brain.

In another example, the disclosure is directed to a computer-readable storage medium comprising instructions that, when executed by a processor, cause the processor to control a stimulation generator to deliver electrical stimulation to a plurality of different areas of an AN of a thalamus of a brain of a patient, wherein the electrical stimulation comprises a frequency greater than or equal to about 80 Hertz, and wherein the electrical stimulation is delivered to each area of the plurality of different areas of the AN at a different time. The instructions further cause the processor to, for each area of the plurality of different areas of the AN of the thalamus, determine a level of brain activity in a HC of the brain of the patient resulting from the delivery of the electrical stimulation to the area, and select at least one of the areas of the AN of the thalamus of the brain of the patient as a target therapy delivery site based on the associated level of brain activity in the HC of the brain.

In another aspect, the disclosure is directed to a computer-readable storage medium comprising instructions. The instructions, when executed by a programmable processor, cause the programmable processor to perform any part of the techniques described herein. The instructions may be, for example, software instructions, such as those used to define a software or computer program. The computer-readable medium may be a computer-readable storage medium such as a storage device (e.g., a disk drive, or an optical drive), memory (e.g., a Flash memory, random access memory or RAM) or any other type of volatile or non-volatile memory that stores instructions (e.g., in the form of a computer program or other executable) to cause a programmable processor to perform the techniques described herein. The computer-readable storage medium may be an article of manufacture, and may be non-transitory.

The details of one or more examples of the disclosure are set forth in the accompanying drawings and the description below. Other features, objects, and advantages will be apparent from the description and drawings, and from the claims.

BRIEF DESCRIPTION OF DRAWINGS

FIGS. 21A and 21B are plots illustrating example effects on brain activity in a hippocampus of a brain of an ovine subject by delivery of stimulation to an anterior nucleus of a thalamus of the brain at various example stimulation pulse rates.

FIGS. 22A and 22B are bar graphs illustrating the amplitudes of the bioelectrical brain signals shown in FIGS. 21A and 21B.

DETAILED DESCRIPTION

Figure 1:
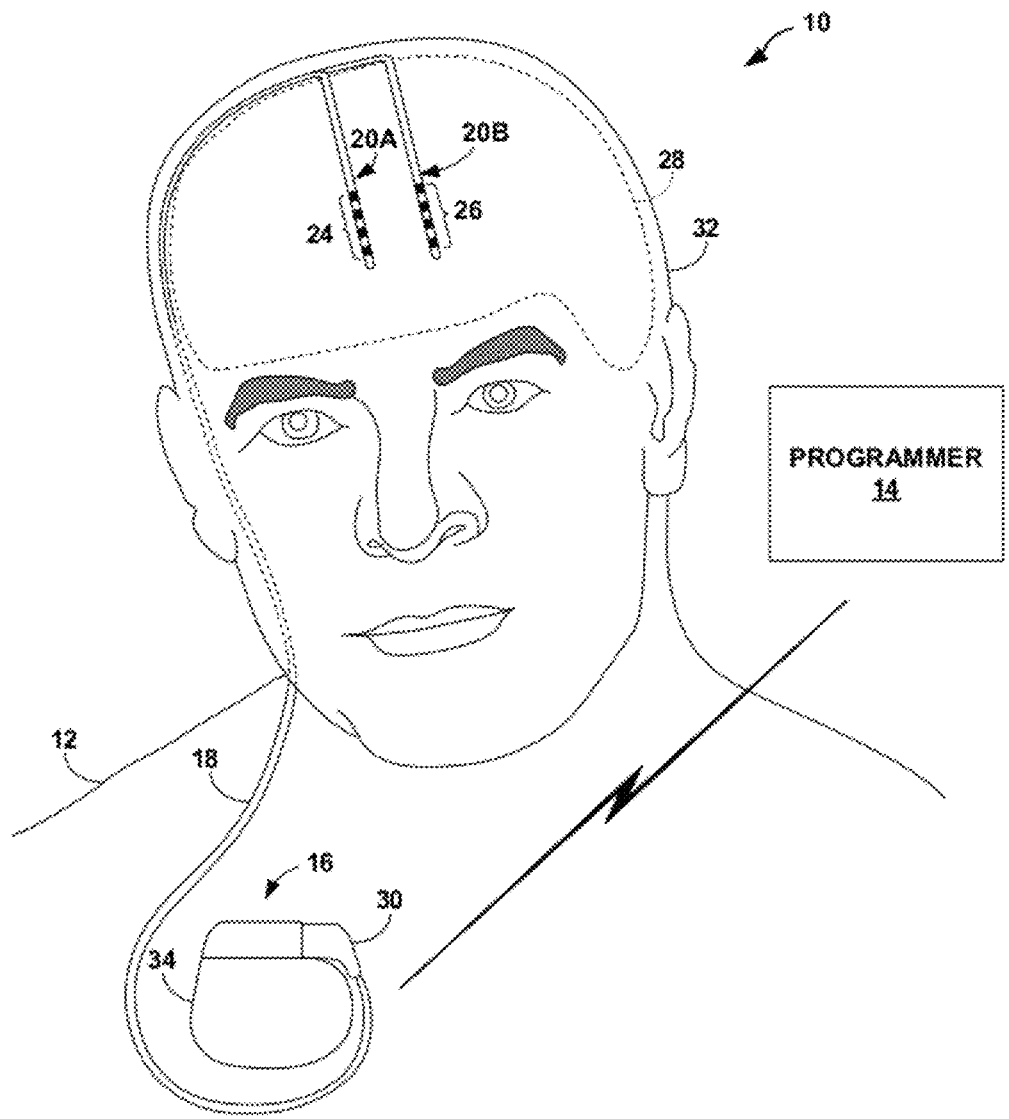
FIG. 1 is a conceptual diagram illustrating an example deep brain stimulation (DBS) system configured to deliver an example electrical stimulation therapy to a target tissue site within a brain of a patient.

FIG. 1 is a conceptual diagram illustrating an example therapy system 10 that is configured to deliver therapy to patient 12 to manage a disorder of patient 12. In some examples, therapy system 10 may deliver therapy to patient 12 to manage a seizure disorder (e.g., epilepsy) of patient 12, which is characterized by the occurrence of seizures. Therapy system 10 may be used to manage the seizure disorder of patient 12 by preventing the onset of seizures, minimizing the severity of seizures, shortening the duration of seizures, minimizing the frequency of seizures, and the like. Patient 12 ordinarily will be a human patient. In some cases, however, therapy system 10 may be applied to other mammalian or non-mammalian non-human patients. While examples of the disclosure are described in some cases with regard to management of seizure disorders, in other examples, therapy system 10 may also provide therapy to manage symptoms of other patient conditions, such as, but not limited to, Alzheimer's disease, psychological disorders, mood disorders, movement disorders or other neurogenerative impairment.

Therapy system 10 includes medical device programmer 14, implantable medical device (IMD) 16, lead extension 18, and one or more leads 20A and 20B (collectively "leads 20") with respective sets of electrodes 24, 26. IMD 16 includes a stimulation generator that is configured to generate and deliver electrical stimulation therapy to one or more regions of brain 28 of patient 12 via a subset of electrodes 24, 26 of leads 20A and 20B, respectively. In the example shown in FIG. 1, therapy system 10 may be referred to as a deep brain stimulation (DBS) system because IMD 16 provides electrical stimulation therapy directly to tissue within brain 28, e.g., a tissue site under the dura mater of brain 28. In other examples, leads 20 may be positioned to deliver therapy to a surface of brain 28 (e.g., the cortical surface of brain 28). In some examples, delivery of stimulation to one or more regions of brain 28, such as an anterior nucleus of the thalamus (also referred to herein as the "anterior nucleus," "anterior thalamic nucleus" or "AN") or cortex of brain 28, may provide an effective treatment to manage a seizure disorder of patient 12. Thus, in some examples, IMD 16 may provide electrical stimulation therapy to an AN of brain 28 of patient 12.

Electrical stimulation generated from the stimulation generator (shown in FIG. 3) of IMD 16 may help prevent the onset of events associated with the patient's disorder or mitigate symptoms of the disorder. For example, electrical stimulation therapy delivered by IMD 16 to a target therapy delivery site within brain 28 may help minimize the occurrence of seizures or minimize the duration, severity or frequency of seizures if patient 12 has a seizure disorder.

IMD 16 may deliver electrical stimulation therapy to brain 28 of patient 12 according to one or more stimulation therapy programs. A therapy program defines one or more electrical stimulation parameter values for therapy generated and delivered from IMD 16 to brain 28 of patient 12. In examples in which IMD 16 delivers electrical stimulation in the form of electrical pulses, for example, the stimulation therapy may be characterized by selected pulse parameters, such as pulse amplitude, pulse rate, and pulse width. In addition, if different electrodes are available for delivery of stimulation, the therapy program may include one or more electrode combinations, which can include selected electrodes (e.g., selected from electrodes 24, 26) and their respective polarities. The exact therapy parameter values of the stimulation therapy that helps prevent or mitigate seizures, such as the amplitude or magnitude (electrical current or voltage) of the stimulation signals, the duration of each signal (e.g., in the case of stimulation pulses, a pulse width or duty cycle), the waveform of the stimuli (e.g., rectangular, sinusoidal or ramped signals), the frequency of the signals, and the like, may be specific for the particular target stimulation site (e.g., the area of the brain) involved as well as the particular patient and patient condition. While stimulation pulses are primarily described herein, stimulation signals may be of any form, such as continuous-time signals (e.g., sine waves) or the like.

In addition to delivering stimulation therapy to manage a disorder of patient 12, therapy system 10 is configured to monitor one or more bioelectrical brain signals of patient 12. For example, IMD 16 may include a sensing module that senses bioelectrical brain signals within one or more regions of brain 28. In some examples, the sensing module of IMD 16 may receive the bioelectrical signals from electrodes 24, 26 or other electrodes positioned to monitored brain signals of patient 12. In the example shown in FIG. 1, the signals generated by electrodes 24, 26 are conducted to the sensing module within IMD 16 via conductors within the respective lead 20A, 20B. Electrodes 24, 26 may also be used to deliver electrical stimulation from the therapy module to target sites within brain 28 as well as sense brain signals within brain 28. In some examples, the sensing module of IMD 16 may sense bioelectrical brain signals via one or more of the electrodes 24, 26 that are also used to deliver electrical stimulation to brain 28. In other examples, one or more of electrodes 24, 26 may be dedicated to sensing bioelectrical brain signals while one or more different electrodes 24, 26 may be dedicated to delivering electrical stimulation.

As described in further detail below, in some examples, bioelectrical signals sensed by IMD 16 within brain 28 of patient 12 or a separate sensing device implanted or external to patient 12 may be used to select a target therapy delivery site. The target therapy delivery site can be, for example, the location within brain 28 at which IMD 16 delivers electrical stimulation (or other therapy, such a therapeutic agent). In some cases, one or more electrodes 24, 26 are implanted at the target therapy delivery site. In this way, the target implantation site for electrodes 24, 26 of leads 20 or the electrode combination (e.g., the subset of electrodes 24, 26) with which IMD delivers electrical stimulation to brain 28 can be selected based on the target therapy delivery site for patient 12.

Depending on the particular stimulation electrodes and sense electrodes used by IMD 16, IMD 16 may monitor brain signals and deliver electrical stimulation at the same region of brain 28 or at different regions of brain 28. In some examples, the electrodes used to sense bioelectrical brain signals may be located on the same lead used to deliver electrical stimulation, while in other examples, the electrodes used to sense bioelectrical brain signals may be located on a different lead than the electrodes used to deliver electrical stimulation. In some examples, a bioelectrical brain signal of patient 12 may be monitored with external electrodes, e.g., scalp electrodes positioned over a temporal lobe of brain 28. Moreover, in some examples, the sensing module that senses bioelectrical brain signals of brain 28 (e.g., the sensing module that generates an electrical signal indicative of the activity within brain 28) is in a physically separate housing from outer housing 34 of IMD 16. However, in the example shown in FIG. 1 and the examples primarily referred to herein for ease of description, the sensing module and therapy module of IMD 16 are enclosed within a common outer housing 34.

Bioelectrical brain signals monitored and sensed by IMD 16 may reflect changes in electrical current produced by the sum of electrical potential differences across brain tissue. Examples of the monitored bioelectrical brain signals include, but are not limited to, an electroencephalogram (EEG) signal, an electrocorticogram (ECoG) signal, a local field potential (LFP) sensed from within one or more regions of a patient's brain and/or action potentials from single cells within brain 28.

In the example shown in FIG. 1, IMD 16 may be implanted within a subcutaneous pocket above the clavicle of patient 12. In other examples, IMD 16 may be implanted within other regions of patient 12, such as a subcutaneous pocket in the abdomen or buttocks of patient 12 or proximate the cranium of patient 12. Implanted lead extension 18 is coupled to IMD 16 via connector block 30 (also referred to as a header), which may include, for example, electrical contacts that electrically couple to respective electrical contacts on lead extension 18. The electrical contacts electrically couple the electrodes 24, 26 carried by leads 20 to IMD 16. Lead extension 18 traverses from the implant site of IMD 16 within a chest cavity of patient 12, along the neck of patient 12 and through the cranium of patient 12 to access brain 28. IMD 16 is constructed of a biocompatible material that resists corrosion and degradation from bodily fluids. IMD 16 can comprise a hermetic outer housing 34, which substantially encloses components, such as a processor, therapy module, and memory.

In the example shown in FIG. 1, leads 20 are implanted within the right and left hemispheres, respectively, of brain 28 in order deliver electrical stimulation to one or more regions of brain 28, which may be selected based on many factors, such as the type of patient condition for which therapy system 10 is implemented to manage. Other implant sites for leads 20 and IMD 16 are contemplated. For example, IMD 16 may be implanted on or within cranium 32 or leads 20 may be implanted within the same hemisphere or IMD 16 may be coupled to a single lead that is implanted in one or both hemispheres of brain 28.

Leads 20 may be positioned to deliver electrical stimulation to one or more target tissue sites within brain 28 to manage patient symptoms associated with a condition of patient 12. Leads 20 may be implanted to position electrodes 24, 26 at a target implantation site within brain 28 via any suitable technique, such as through respective burr holes in a skull of patient 12 or through a common burr hole in the cranium 32. Leads 20 may be placed at any location within brain 28 such that electrodes 24, 26 are capable of providing electrical stimulation to one or more target therapy delivery sites within brain 28 during treatment.

Different neurological or psychiatric disorders may be associated with activity in one or more of regions of brain 28, which may differ between patients. For example, in the case of a seizure disorder or Alzheimer's disease, leads 20 may be implanted to deliver electrical stimulation to regions within the Circuit of Papez, such as, e.g., the anterior nucleus, the internal capsule, the cingulate, the fornix, the mammillary bodies, the mammillothalamic tract (mammillothalamic fasciculus), and/or hippocampus. Regions of brain 28 may be functionally connected to one another via neurological pathways such that activity within one region of brain 28 may affect activity within another region of brain 28. For example, electrical stimulation delivered by IMD 16 to a particular region of brain 28 may influence brain signals in one or more other regions of brain 28. In some examples, brain activity can be indicated by a signal characteristic (e.g., an amplitude, frequency, and/or frequency domain characteristic) of a bioelectrical brain signal. As an example, the signal characteristic of a bioelectrical brain signal sensed within a particular region of brain 28 may change as the brain activity in the region changes.

One example of functionally connected regions of brain 28 includes the Circuit of Papez (described below with respect to FIG. 5). Electrical stimulation delivered from IMD 16 to a particular region of the Circuit of Papez may influence brain signals in one or more other regions of the Circuit of Papez.

As described in further detail below, in some examples, a target therapy delivery site may be selected based on the effect of relatively high frequency electrical stimulation delivered to a first region of brain 28 on the brain activity in a second region of brain 28 that is different than the first region, but functionally connected to the first region. A target implantation site for electrodes 24, 26 of leads 20, an electrode combination with which IMD 16 delivers stimulation to brain 28 or senses activity in brain 28, or both, may be selected based on the target therapy delivery site. In some examples described herein, a target implantation site for electrodes 24, 26 of leads 20 is selected based on brain activity within one region of the Circuit of Papez after (e.g., immediately after or some predetermined duration of time after) a relatively high frequency electrical stimulation signal is delivered to a different region of the Circuit of Papez. As an example, a target therapy delivery site within an AN of brain 28 can be selected based on the extent of a functional connection between the target therapy delivery site and a HC of brain 28. The relative strength of a functional connection between the AN and the HC may be characterized by the effect of stimulation delivery to a region of the AN on the brain activity level within the HC. In examples described herein, a meaningful functional connection between an area of the AN and the HC is identified when the activity in the HC is suppressed in response to relatively high frequency stimulation delivered to the area of the AN.

The suppression of activity in the HC can be indicated by, for example, a decrease in a time domain signal characteristic (e.g., amplitude and/or frequency) of a bioelectrical brain signal indicative of activity in the HC or a decrease in the signal characteristic relative to the amplitude and/or frequency, respectively, of the bioelectrical brain signal sensed prior to the delivery of stimulation to the AN or another reference point. In other examples, the suppression of activity in the HC can be indicated by, for example, a distribution of energy in the frequency bands of the bioelectrical brain signal indicative of activity in the HC, such as an increase in the energy level of a relatively low frequency band (e.g., at a frequency of approximately 2 Hz, such as 2 Hz), which is discussed in further detail below. In other examples, the suppression of activity in the HC that is indicative of a meaningful functional connection between an area of the AN and the HC is indicated by a power level in one or more frequency bands of interest of the bioelectrical brain signal indicative of activity in the HC.

While examples in which a target therapy delivery site within the AN of brain 28 is selected based on brain activity within the HC are primarily referred to herein, in other examples, the techniques described herein may also be used to select a target stimulation site within other regions of brain 28.

In some examples, a functional connection between two regions of brain 28 is characterized by the effect of relatively high frequency stimulation delivery (e.g., greater than about 80 Hertz (Hz), such as about 80 Hz to about 160 Hz) to a first region of brain 28 on a brain activity level within a second region of brain 28. In some cases, a level of brain activity in a region of brain 28 is indicated by one or more characteristics of a bioelectrical brain signal sensed within the second region of brain 28 or within a different region of brain 28 known to have a functional connection to the second region. The level of brain activity within brain 28 can be indicated by, for example, an amplitude of a bioelectrical brain signal, a variance of the bioelectrical brain signal over time, or a frequency domain characteristic (e.g., an energy level within one or more specific frequency bands) of the bioelectrical brain signal. The amplitude value may comprise an average, peak, median or instantaneous amplitude value over a period of time or a maximum amplitude or an amplitude in a particular percentile of the maximum (e.g., an amplitude value that represents 95% of the maximum amplitude value). In addition, in some examples, the amplitude value may be an absolute amplitude value or a root mean square amplitude value.

IMD 16 may deliver therapy to the brain 28 in a manner that influences the brain signals within one or more regions of brain 28. For example, IMD 16 may deliver therapy to the AN, HC, or other suitable region of brain 28 to control a brain state of patient 12 (e.g., as indicated by bioelectrical brain signals sensed within the Circuit of Papez) in a manner that effectively treats a disorder of patient 12. For example, in the case of a seizure disorder, IMD 16 may deliver therapy to a region of brain 28 via a selected subset of electrodes 24, 26 (referred to herein as an electrode combination) to suppress a level of brain activity within the AN, HC, or another brain region associated with the occurrence of seizures (e.g., a seizure focus of brain 28). IMD 16 may deliver therapy to brain 28 via a selected subset of electrodes 24, 26 to change one or more characteristics of a bioelectrical brain signal exhibited in one or more regions of brain 28 that is associated with an undesirable baseline brain state (e.g., a baseline brain state exhibited by patient 12 in the absence of therapy) to characteristics associated with a desirable brain state. In a desirable brain state, the bioelectrical brain signals sensed via the sensing module of IMD 16 may be indicative of a patient state in which the patient condition is treated, e.g., one or more of symptoms of the patient disorder or mitigated or even eliminated. For example, in the case of a seizure disorder, in a desirable brain state, the possibility of an onset of a seizure or a severity, duration, or frequency of seizures may be reduced.

Although leads 20 are shown in FIG. 1 as being coupled to a common lead extension 18, in other examples, leads 20 may be coupled to IMD 16 via separate lead extensions or directly coupled to IMD 16. Moreover, although FIG. 1 illustrates system 10 as including two leads 20A and 20B coupled to IMD 16 via lead extension 18, in some examples, system 10 may include one lead or more than two leads.

In the examples shown in FIG. 1, electrodes 24, 26 of leads 20 are shown as ring electrodes. Ring electrodes may be relatively easy to program and are typically capable of delivering an electrical field to any tissue adjacent to leads 20. In other examples, electrodes 24, 26 of leads 20 may have different configurations. For example, electrodes 24, 26 of leads 20 may have a complex electrode array geometry that is capable of producing shaped electrical fields. The complex electrode array geometry may include multiple electrodes (e.g., partial ring or segmented electrodes) around the perimeter of each lead 20, rather than a ring electrode. In this manner, electrical stimulation may be directed to a specific direction from leads 20 to enhance therapy efficacy and reduce possible adverse side effects from stimulating a large volume of tissue. In some examples, outer housing 34 of IMD 16 may include one or more stimulation and/or sensing electrodes. For example, housing 34 can comprise an electrically conductive material that is exposed to tissue of patient 12 when IMD 16 is implanted in patient 12, or an electrode can be attached to housing 34. In other examples, one or both leads 20 may have a shape other than elongated cylinders as shown in FIG. 1. For example, leads 20 may be paddle leads, spherical leads, bendable leads, or any other type of shape effective in treating patient 12.

External programmer 14 is configured to wirelessly communicate with IMD 16 as needed to provide or retrieve therapy information. Programmer 14 is an external computing device that the user, e.g., the clinician and/or patient 12, may use to communicate with IMD 16. For example, programmer 14 may be a clinician programmer that the clinician uses to communicate with IMD 16 and program one or more therapy programs for IMD 16. Alternatively, programmer 14 may be a patient programmer that allows patient 12 to select programs and/or view and modify therapy parameters. The clinician programmer may include more programming features than the patient programmer. In other words, more complex or sensitive tasks may only be allowed by the clinician programmer to prevent an untrained patient from making undesired changes to IMD 16.

Programmer 14 may be a hand-held computing device with a display viewable by the user and an interface for providing input to programmer 14 (i.e., a user input mechanism). For example, programmer 14 may include a small display screen (e.g., a liquid crystal display (LCD) or a light emitting diode (LED) display) that presents information to the user. In addition, programmer 14 may include a touch screen display, keypad, buttons, a peripheral pointing device or another input mechanism that allows the user to navigate though the user interface of programmer 14 and provide input. If programmer 14 includes buttons and a keypad, the buttons may be dedicated to performing a certain function, e.g., a power button, or the buttons and the keypad may be soft keys that change in function depending upon the section of the user interface currently viewed by the user. In some examples, the screen (not shown) of programmer 14 may be a touch screen that allows the user to provide input directly to the user interface shown on the display. The user may use a stylus or their finger to provide input to the display.

In other examples, programmer 14 may be a larger workstation or a separate application within another multi-function device, rather than a dedicated computing device. For example, the multi-function device may be a notebook computer, tablet computer, workstation, cellular phone, personal digital assistant or another computing device that may run an application that enables the computing device to operate as a secure medical device programmer 14. A wireless adapter coupled to the computing device may enable secure communication between the computing device and IMD 16.

When programmer 14 is configured for use by the clinician, programmer 14 may be used to transmit initial programming information to IMD 16. This initial information may include hardware information, such as the type of leads 20, the arrangement of electrodes 24, 26 on leads 20, the position of leads 20 within brain 28, initial programs defining therapy parameter values, and any other information that may be useful for programming into IMD 16. Programmer 14 may also be capable of completing functional tests (e.g., measuring the impedance of electrodes 24, 26 of leads 20).

The clinician may also store therapy programs within IMD 16 with the aid of programmer 14. During a programming session, the clinician may determine one or more therapy programs that may provide efficacious therapy to patient 12 to address symptoms associated with the seizure disorder (or other patient condition). During the programming session, patient 12 may provide feedback to the clinician as to the efficacy of the specific program being evaluated or the clinician may evaluate the efficacy based on one or more physiological parameters of patient (e.g., heart rate, respiratory rate or muscle activity).

Programmer 14 may also assist the clinician in the identification of a target implantation site for leads 20 or an electrode combination for stimulation therapy delivery for patient 12. For example, as discussed with respect to FIGS. 23-25, programmer 14 can display indications of a plurality of areas the AN of brain 28 (which may each be an potential target therapy delivery site) and one or more associated metrics, where the metrics indicate the relative functional connection between the respective area of the AN and the HC of brain 28. Based on the displayed metrics, a clinician may select one or more of the areas of the AN as a target therapy delivery site. In some examples, programmer 14 may associate each of the areas of the AN with a particular subset of electrodes 24, 26, such that programmer 14 or the clinician may also select an electrode combination for therapy delivery based on the displayed bioelectrical brain signals.

Programmer 14 may also be configured for use by patient 12 in some examples. When configured as a patient programmer, programmer 14 may have limited functionality (compared to a clinician programmer) in order to prevent patient 12 from altering critical functions of IMD 16 or applications that may be detrimental to patient 12. In this manner, programmer 14 may only allow patient 12 to adjust values for certain therapy parameters or set an available range of values for a particular therapy parameter.

Whether programmer 14 is configured for clinician or patient use, programmer 14 is configured to communicate to IMD 16 and, optionally, another computing device, via wireless communication. Programmer 14, for example, may be configured to communicate via wireless communication with IMD 16 using radio frequency (RF) telemetry techniques known in the art. Programmer 14 may also communicate with another programmer or computing device via a wired or wireless connection using any of a variety of local wireless communication techniques, such as RF communication according to the 802.11 or Bluetooth specification sets, infrared (IR) communication according to the IRDA specification set, or other standard or proprietary telemetry protocols. Programmer 14 may also communicate with other programming or computing devices via exchange of removable media, such as magnetic or optical disks, memory cards or memory sticks. Further, programmer 14 may communicate with IMD 16 and another programmer via remote telemetry techniques known in the art, communicating via a local area network (LAN), wide area network (WAN), public switched telephone network (PSTN), or cellular telephone network, for example.

Therapy system 10 may be implemented to provide chronic stimulation therapy to patient 12 over the course of several months or years. However, system 10 may also be employed on a trial basis to evaluate therapy before committing to full implantation. If implemented temporarily, some components of system 10 may not be implanted within patient 12. For example, patient 12 may be fitted with an external medical device, such as a trial stimulator, rather than IMD 16. The external medical device may be coupled to percutaneous leads or to implanted leads via a percutaneous extension. If the trial stimulator indicates DBS system 10 provides effective treatment to patient 12, the clinician may implant a chronic stimulator within patient 12 for relatively long-term treatment. In addition, the trial stimulator can be used to select a target therapy delivery site for patient 12.

Figure 2:
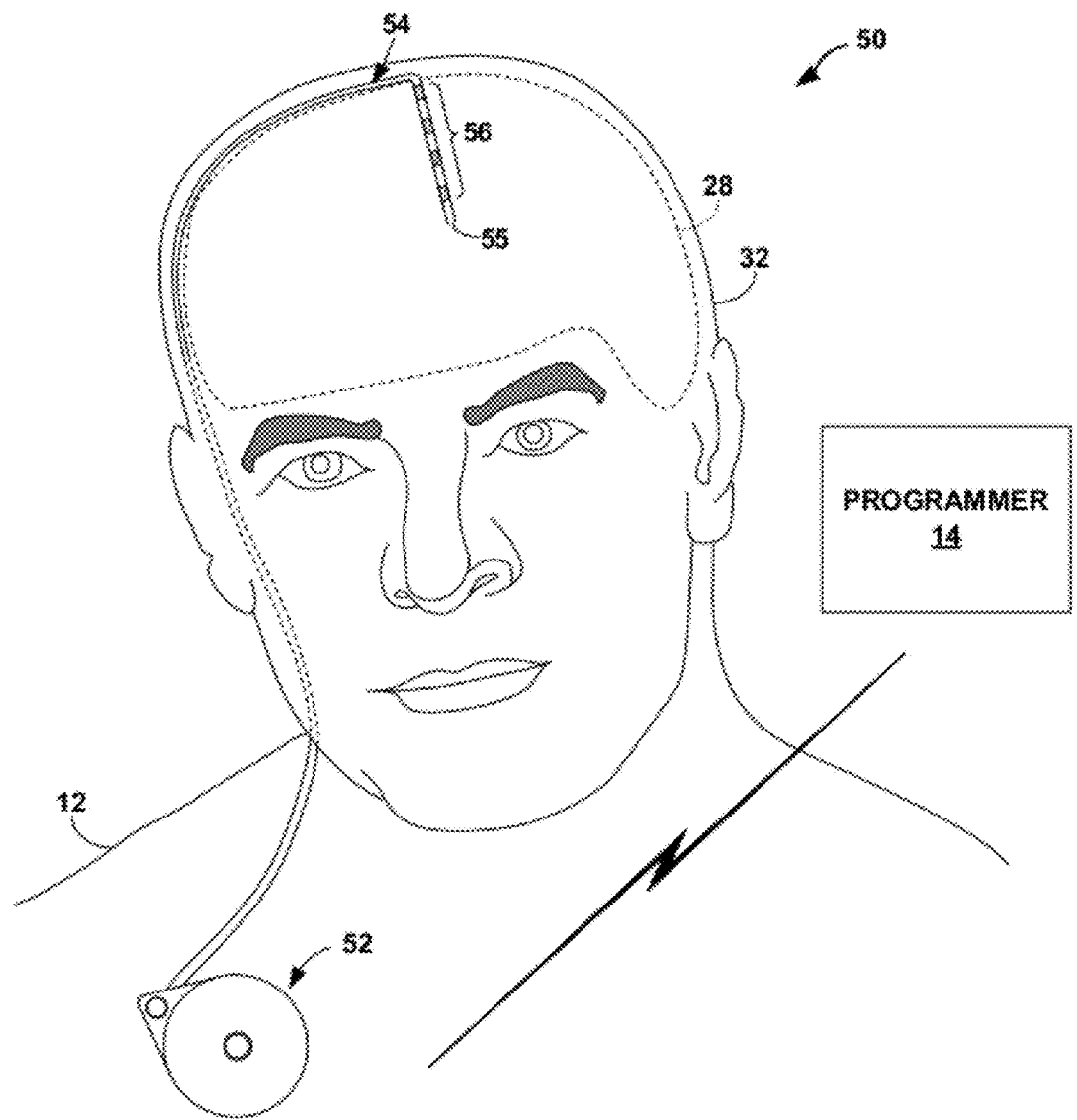
FIG. 2 is a conceptual diagram illustrating an example therapy system configured to deliver a therapeutic agent to a tissue site within a brain of a patient.

FIG. 2 is a conceptual diagram illustrating an example therapy system 50 for delivery of a therapeutic agent to a tissue site within brain 28 of a patient 12. Therapy system 50 includes IMD 52 and catheter 54, which includes a plurality of electrodes 56 for sensing one or more bioelectrical brain signals within brain 28 of patient 12. IMD 52 is configured to deliver at least one therapeutic agent, such as a pharmaceutical agent (e.g., anti-seizure medication), anti-inflammatory agent, gene therapy agent, or the like, to a target tissue site within brain 28 of patient 12 via catheter 54, which is in fluid communication with IMD 52. Catheter 54 may be coupled to IMD 52 either directly or with the aid of an extension (not shown in FIG. 1).

In some examples, IMD 52 includes a fluid pump or another device that delivers a therapeutic agent in some metered or other desired flow dosage to the therapy site within patient 12 from a reservoir within IMD 52 via catheter 54. For treatment of a seizure disorder, drug therapy may be intended to minimize the severity, duration or frequency of seizures. Examples of pharmaceutical agents that IMD 52 may deliver to patient 12 to manage a seizure include, but are not limited to, adenosine, lorazepam, carbamazepine, oxcarbazepine, valproate, divalproex sodium, acetazolamide, diazepam, phenytoin, phenytoin sodium, felbamate, tiagabine, levetiracetam, clonazepam, lamotrigine, primidone, gabapentin, phenobarbital, topiramate, clorazepate, ethosuximide, and zonisamide. In other examples, IMD 52 delivers a therapeutic agent to tissue sites within patient 12 other than brain 28.

Electrodes 56 are configured to sense bioelectrical signals within brain 28 of patient 12 to allow system 50 to monitor one or more bioelectrical brain signals within brain 28. In some examples, electrodes 56 may be substantially similar to one or more of electrodes 24, 26 (FIG. 1). Although FIG. 2 illustrates catheter 54 including four sense electrodes 56, in other examples, a catheter may include any suitable number of sense electrodes, such as one, two, three or greater than four. In addition, although sense electrodes 56 are located proximal to the fluid delivery port 55 of catheter 54 in the example shown in FIG. 2, in other examples, one or more of sense electrodes 56 may be distal to fluid delivery port 55 of catheter 54. Catheter 54 may include more than one fluid delivery port. Thus, in some examples, one or more sense electrodes 56 may be located between fluid delivery ports of catheter 54.

Although the examples of this disclosure are primarily described with regard to the selection of a target therapy delivery site for electrical stimulation therapy, such examples may be similarly applied to the selection of a target therapy delivery site for therapy provided by the delivery of a therapeutic agent. In one example, for the treatment of a seizure disorder, IMD 52 may deliver a therapeutic agent, such as, e.g., adenosine, to a target therapy delivery site selected using the techniques described below, e.g., based on the functional connections between a plurality of areas of an AN and the HC of brain 28. Thus, the systems, devices, and techniques described herein are applicable to selecting a target therapy delivery site for therapy delivered by therapy system 50.

Figure 3:
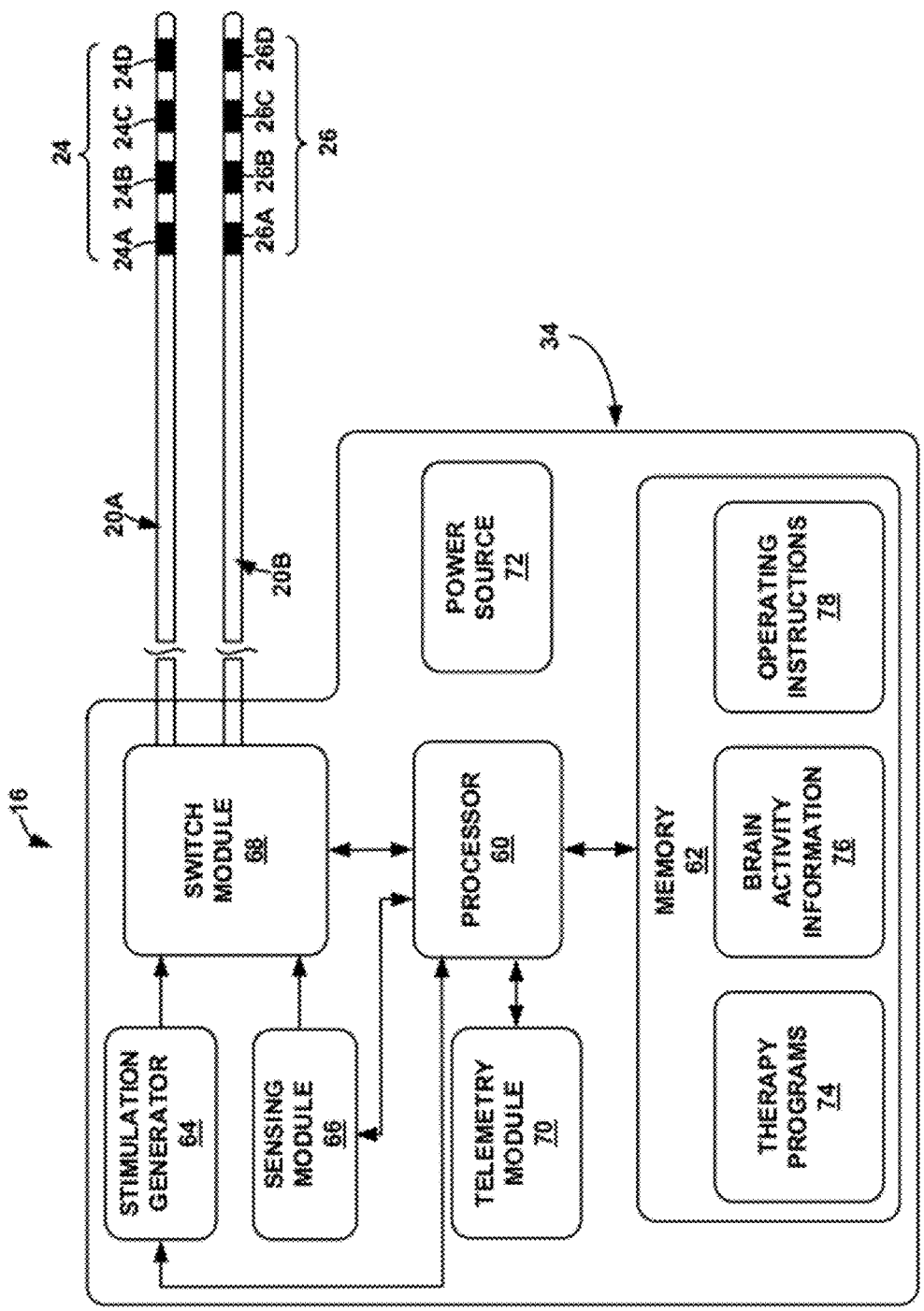
FIG. 3 is functional block diagram illustrating components of an example medical device.

FIG. 3 is functional block diagram illustrating components of IMD 16. In the example shown in FIG. 3, IMD 16 includes processor 60, memory 62, stimulation generator 64, sensing module 66, switch module 68, telemetry module 70, and power source 72. Memory 62 may include any volatile or non-volatile media, such as a random access memory (RAM), read only memory (ROM), non-volatile RAM (NVRAM), electrically erasable programmable ROM (EEPROM), flash memory, and the like. Memory 62 may store computer-readable instructions that, when executed by processor 60, cause IMD 16 to perform various functions described herein.

In the example shown in FIG. 3, memory 62 stores therapy programs 74, brain activity information 76, and operating instructions 78 in separate memories within memory 62 or separate areas within memory 62. Each stored therapy program 74 defines a particular program of therapy in terms of respective values for electrical stimulation parameters, such as a stimulation electrode combination, electrode polarity, current or voltage amplitude, and, if stimulation generator 64 generates and delivers stimulation pulses, the therapy programs may define values for a pulse width, and pulse rate of a stimulation signal. In examples when IMD 16 delivers electrical stimulation therapy on a cyclic basis (as compared to a substantially continuous basis), memory 62 stores, e.g., as part of therapy programs 74, cycle parameter information, such as, on cycle time duration and off cycle duration. In some examples, the therapy programs may be stored as a therapy group, which defines a set of therapy programs with which stimulation may be generated. The stimulation signals defined by the therapy programs of the therapy group may be delivered together on an overlapping or non-overlapping (e.g., time-interleaved) basis.

Brain activity information 76 stored by memory 62 can include information collected during the mapping of the functional connection between plurality of areas of the AN of brain 28 and the HC of brain 28 (e.g., using the techniques described with respect to FIGS. 6-9), as well as any other information indicative of activity within one or more regions of brain 28. Examples of information stored by brain activity information 76 include, but are not limited to, bioelectrical brain signal data generated by sensing module 66 via at least one of electrodes 24, 26 and, in some cases, at least a portion of outer housing 34 of IMD 16, an electrode on outer housing 34 of IMD 16 or another reference, and metrics indicative of a functional connection between a particular area of the AN of brain 28 and the HC of brain 28. In some examples, processor 60 may determine the brain activity level within a particular region of brain 28 of patient 12 based on bioelectrical brain signals sensed by sensing module 66 via a subset of electrodes 24, 26, which may be referred to herein as a sense electrode combination. Thus, in some examples, processor 60 stores sensed bioelectrical brain signals as brain activity information 76. Operating instructions 78 guide general operation of IMD 16 under control of processor 60, and may include instructions for monitoring brains signals within one or more brain regions via electrodes 24, 26 and/or selecting one or more therapy cycle parameters based on the monitored brain signals.

Stimulation generator 64, under the control of processor 60, generates stimulation signals for delivery to patient 12 via selected combinations of electrodes 24, 26. In some examples, during therapy delivery (versus mapping of the AN to the HC) to manage a seizure disorder, stimulation generator 64 generates and delivers stimulation signals to one or more target regions of brain 28 (FIG. 1), e.g., the AN, of patient 12 via a select combination of electrodes 24, 26 (referred to herein as a stimulation electrode combination) where the stimulation signals have a frequency in a range of about 3 Hertz (Hz) to about 250 Hz, a voltage of about 0.1 volts to about 10.5 volts, and a pulse width of about 60 microseconds to about 450 microseconds. In some examples, the stimulation signals have a frequency of 120 Hz, a voltage of about 4 volts, and a pulse width of about 100 microseconds. In addition, in some examples, the stimulation signals have a frequency of 145 Hz, a voltage of about 5 volts, and a pulse width of about 145 microseconds.

In some examples, stimulus frequencies below approximately 40 Hz (such as, e.g., between approximately 5 Hz and 40 Hz, between approximately 5 Hz and 10 Hz, approximately 10 Hz, or approximately 5 Hz) may be used to increase excitability in the HC of brain 28, while in some examples, stimulus frequencies greater than 40 Hz (such as, e.g., between approximately 40 Hz and 160 Hz, between approximately 80 Hz and 160 Hz, approximately 80 Hz, or approximately 160 Hz) may be used to suppress excitability in the HC of brain 28. It is believed that suppression of excitability in the HC may help treat seizure disorders, such as by reducing the possibility of an onset of a seizure, by reducing a duration or severity of a seizure, and/or by reducing the frequency of seizures.

During the selection of a target therapy delivery site within AN of brain 28, processor 60 controls stimulation generator 64 to generate and deliver relatively high frequency stimulation, such as stimulation signals having a frequency greater than about 80 Hz, such as about 80 Hz to about 160 Hz, e.g., stimulation pulses having pulse rates of about 80 Hz to about 160 Hz. Other stimulation parameter values, and other therapy cycles are contemplated. Other ranges of therapy parameter values may also be useful, and may depend on the target stimulation site within patient 12, which may or may not be within brain 28.

Processor 60 may include any one or more of a microprocessor, a controller, a digital signal processor (DSP), an application specific integrated circuit (ASIC), a field-programmable gate array (FPGA), discrete logic circuitry, and the functions attributed to processor 60 herein may be embodied as firmware, hardware, software or any combination thereof. Processor 60 is configured to control stimulation generator 64 according to therapy programs 74 stored in memory 62 to apply particular stimulation parameter values specified by one or more programs, such as amplitude, pulse width, and pulse rate.

Figure 4:
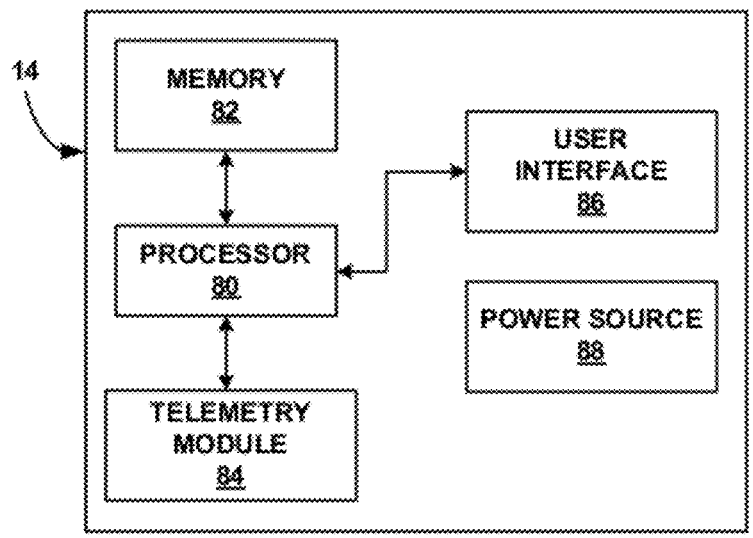
FIG. 4 is a functional block diagram illustrating components of an example medical device programmer.

In the example shown in FIG. 4, the set of electrodes 24 of lead 20A includes electrodes 24A, 24B, 24C, and 24D, and the set of electrodes 26 of lead 20B includes electrodes 26A, 26B, 26C, and 26D. Processor 60 may control switch module 68 to apply the stimulation signals generated by stimulation generator 64 to selected combinations of electrodes 24, 26. In particular, switch module 68 may couple stimulation signals to selected conductors within leads 20, which, in turn, deliver the stimulation signals across the electrodes 24, 26 of the selected stimulation electrode combination. Switch module 68 may be a switch array, switch matrix, multiplexer, or any other type of switching module configured to selectively couple stimulation energy to selected electrodes 24, 26 and to selectively sense bioelectrical brain signals with selected electrodes 24, 26. Hence, stimulation generator 64 is coupled to electrodes 24, 26 via switch module 68 and conductors within leads 20. In some examples, however, IMD 16 does not include switch module 68.

Stimulation generator 64 may be a single channel or multi-channel stimulation generator. In particular, stimulation generator 64 may be capable of delivering, a single stimulation pulse, multiple stimulation pulses or continuous signal at a given time via a single electrode combination or multiple stimulation pulses at a given time via multiple electrode combinations. In some examples, however, stimulation generator 64 and switch module 68 may be configured to deliver multiple channels on a time-interleaved basis. For example, switch module 68 may serve to time divide the output of stimulation generator 64 across different electrode combinations at different times to deliver multiple programs or channels of stimulation energy to patient 12.

Sensing module 66 is configured to sense bioelectrical brain signals of patient 12 via a sense electrode combination, which can include a selected subset of electrodes 24, 26 or with one or more electrodes 24, 26 and at least a portion of a conductive outer housing 34 of IMD 16, an electrode on an outer housing of IMD 16 or another reference. Processor 60 may control switch module 68 to electrically connect sensing module 66 to selected electrodes 24, 26. In this way, sensing module 66 may selectively sense bioelectrical brain signals with different combinations of electrodes 24, 26 (and/or a reference other than an electrode 24, 26). As previously described, processor 60 may monitor the brain state of patient 12 via the sensed bioelectrical brain signals. In some examples, processor 60 may select an electrode combination for delivering efficacious stimulation therapy to patient 12 based on one or more characteristics of the bioelectrical brain signals monitored by sensing module 66. In addition, in some examples, an implantation site for leads 20 may be selected based on one or more characteristics of the bioelectrical brain signals monitored by sensing module 66. Although sensing module 66 is incorporated into a common outer housing 34 with stimulation generator 64 and processor 60 in FIG. 4, in other examples, sensing module 66 is in a separate outer housing from outer housing 34 of IMD 16 and communicates with processor 60 via wired or wireless communication techniques.

Telemetry module 70 supports wireless communication between IMD 16 and an external programmer 14 or another computing device under the control of processor 60. Processor 60 of IMD 16 may receive, as updates to programs, values for various stimulation parameters such as amplitude and electrode combination, from programmer 14 via telemetry module 70. The updates to the therapy programs may be stored within therapy programs 74 portion of memory 62. Telemetry module 70 in IMD 16, as well as telemetry modules in other devices and systems described herein, such as programmer 14, may accomplish communication by RF communication techniques. In addition, telemetry module 70 may communicate with external medical device programmer 14 via proximal inductive interaction of IMD 16 with programmer 14. Accordingly, telemetry module 70 may send information to external programmer 14 on a continuous basis, at periodic intervals, or upon request from IMD 16 or programmer 14. For example, processor 60 may transmit brain state information 76 to programmer 14 via telemetry module 70.

Power source 72 is configured to deliver operating power to various components of IMD 16. Power source 72 may include, for example, a small rechargeable or non-rechargeable battery and a power generation circuit to produce the operating power. Recharging may be accomplished through proximal inductive interaction between an external charger and an inductive charging coil within IMD 16. In some examples, power requirements may be small enough to allow IMD 16 to utilize patient motion and implement a kinetic energy-scavenging device to trickle charge a rechargeable battery. In other examples, traditional batteries may be used for a limited period of time.

FIG. 4 is a functional block diagram illustrating components of an example medical device programmer 14 (FIG. 1). Programmer 14 includes processor 80, memory 82, telemetry module 84, user interface 86, and power source 88. Processor 80 controls user interface 86 and telemetry module 84, and stores and retrieves information and instructions to and from memory 82. Programmer 14 may be configured for use as a clinician programmer or a patient programmer. Processor 80 may comprise any combination of one or more processors including one or more microprocessors, DSPs, ASICs, FPGAs, or other equivalent integrated or discrete logic circuitry. Accordingly, processor 80 may include any suitable structure, whether in hardware, software, firmware, or any combination thereof, to perform the functions ascribed herein to processor 80.

A user, such as a clinician or patient 12, may interact with programmer 14 through user interface 86. User interface 86 includes a display (not shown), such as a LCD or LED display or other type of screen, to present information related to the therapy, such as information related to bioelectrical signals sensed via a plurality of sense electrode combinations in response to the delivery of stimulation to brain 28. In addition, user interface 86 may include an input mechanism to receive input from the user. The input mechanisms may include, for example, buttons, a keypad (e.g., an alphanumeric keypad), a peripheral pointing device or another input mechanism that allows the user to navigate though user interfaces presented by processor 80 of programmer 14 and provide input.

As discussed above, if programmer 14 includes buttons and a keypad, the buttons may be dedicated to performing a certain function, or the buttons and the keypad may be soft keys that change function depending upon the section of the user interface currently viewed by the user. In addition, or instead, the screen (not shown) of programmer 14 may be a touch screen that allows the user to provide input directly to the user interface shown on the display. The user may use a stylus or their finger to provide input to the display. In other examples, user interface 86 also includes audio circuitry for providing audible instructions or sounds to patient 12 and/or receiving voice commands from patient 12, which may be useful if patient 12 has limited motor functions. Patient 12, a clinician or another user may also interact with programmer 14 to manually select therapy programs, generate new therapy programs, modify therapy programs through individual or global adjustments, and transmit the new programs to IMD 16.

In some examples, at least some of the control of stimulation delivery by IMD 16 may be implemented by processor 80 of programmer 14. For example, in some examples, processor 80 may control stimulation generator 64 of IMD 16 to generate and deliver electrical stimulation to a plurality of areas of AN of brain 28 and may further control sensing module 66 to sense a bioelectrical brain signal within brain 28 that is indicative of the brain activity level within the HC of brain 28. As described in further detail below, in some cases, the bioelectrical brain signal that indicates the brain activity level within HC may be sensed within HC or may be sensed within AN. It is believed that neural activity in the HC may be reflected back to the AN via a pathway in the Circuit of Papez, such that the bioelectrical brain signal sensed within AN may be a surrogate for brain activity within the HC. As discussed in further detail below with respect to FIG. 6, the brain activity level within the HC can be determined after the delivery of stimulation to each area of the AN, such that each area of the AN is associated with a brain activity level within the HC. Processor 80, automatically or with the aid of a clinician, may select one or more of the areas of the AN as a target therapy delivery site based on the brain activity level within the HC of brain 28 associated with the areas of the AN. For example, in the case of a seizure disorder, processor 80 may select the one or more areas of the AN associated with the lowest brain activity level in the HC as a target therapy delivery site. As another example, in the case of Alzheimer's disease therapy, processor 80 may select the one or more areas of the AN associated with the highest brain activity level in the HC as a target therapy delivery site.

Memory 82 may include instructions for operating user interface 86 and telemetry module 84, and for managing power source 88. Memory 82 may also store any therapy data retrieved from IMD 16, such as, but not limited to, brain activity information. The clinician may use this therapy data to determine the progression of the patient condition in order to plan future treatment for the seizure disorder (or other patient condition) of patient 12. Memory 82 may include any volatile or nonvolatile memory, such as RAM, ROM, EEPROM or flash memory. Memory 82 may also include a removable memory portion that may be used to provide memory updates or increases in memory capacities. A removable memory may also allow sensitive patient data to be removed before programmer 14 is used by a different patient.

Wireless telemetry in programmer 14 may be accomplished by RF communication or proximal inductive interaction of external programmer 14 with IMD 16. This wireless communication is possible through the use of telemetry module 84. Accordingly, telemetry module 84 may be similar to the telemetry module contained within IMD 16. In alternative examples, programmer 14 may be capable of infrared communication or direct communication through a wired connection. In this manner, other external devices may be capable of communicating with programmer 14 without needing to establish a secure wireless connection.

Power source 88 is configured to deliver operating power to the components of programmer 14. Power source 88 may include a battery and a power generation circuit to produce the operating power. In some examples, the battery may be rechargeable to allow extended operation. Recharging may be accomplished by electrically coupling power source 88 to a cradle or plug that is connected to an alternating current (AC) outlet. In addition, recharging may be accomplished through proximal inductive interaction between an external charger and an inductive charging coil within programmer 14. In other examples, traditional batteries (e.g., nickel cadmium or lithium ion batteries) may be used. In addition, programmer 14 may be directly coupled to an alternating current outlet to operate. Power source 88 may include circuitry to monitor power remaining within a battery. In this manner, user interface 86 may provide a current battery level indicator or low battery level indicator when the battery needs to be replaced or recharged. In some cases, power source 88 may be capable of estimating the remaining time of operation using the current battery.

Figure 5:
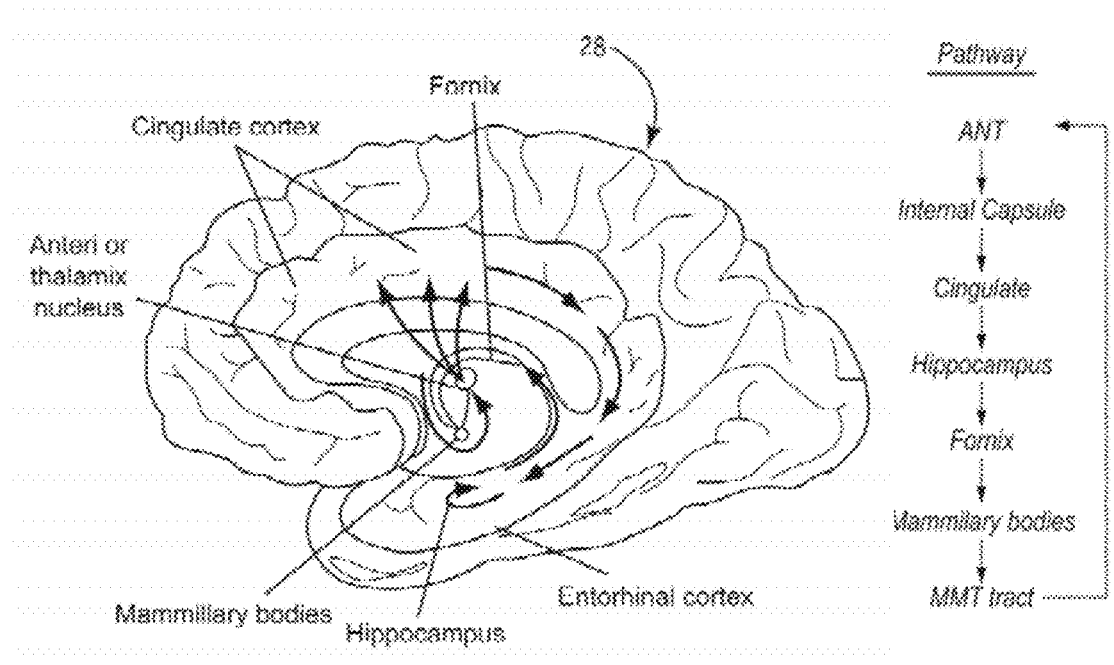
FIG. 5 is a conceptual diagram illustrating example regions of a brain of a patient, and, in particular, regions of the brain included in the Circuit of Papez.

FIG. 5 is a conceptual diagram illustrating example regions of brain 28 of patient 12 and, in particular, regions of brain 28 included in the Circuit of Papez (also referred to as the Papez Circuit). The regions of the brain 28 within the Circuit of Papez are believed to be involved in the generation and spread of seizure activity. The Circuit of Papez is one of the major pathways of the limbic system, and the regions of brain 28 within the Circuit of Papez includes the AN, internal capsule, cingulate (labeled as the cingulate cortex in FIG. 5), HC, fornix, entorhinal cortex, mammillary bodies, and mammillothalamic tract (MMT). The regions of brain 28 within the Circuit of Papez may be considered to be functionally related (also referred to herein as functionally connected), such that activity within one part of the Circuit of Papez may affect activity within another part of the Circuit of Papez. In this way, the delivery of stimulation to one region (e.g., the AN) of the Circuit of Papez may affect the brain activity level within another region of the Circuit of Papez (e.g., the HC).

In some examples, electrodes 24, 26 are implanted to deliver electrical stimulation therapy generated via stimulation generator 64 (FIG. 3) to and/or monitor bioelectrical brain signals within one or more regions of the brain in the Circuit of Papez, such as, e.g., the AN, the internal capsule, the cingulate, the formix, the mammillary bodies, the mammillothalamic tract, and/or HC. In some examples, a disorder of patient 12 may be effectively managed by controlling or influence the brain activity level within one or more regions of the Circuit of Papez. For example, with respect to seizure disorders, therapy may be delivered from IMD 16 to regions within the Circuit of Papez to suppress brain activity (also referred to as cortical activity) within regions of the Circuit of Papez, such as, e.g., the HC. Suppression of brain activity within the HC via therapy may reduce the likelihood of a seizure by patient 12. As another example, for treatment of Alzheimer's disease, therapy may be delivered from IMD 16 to regions within the Circuit of Papez to increase cortical activity within the regions of the Circuit of Papez, such as, e.g., the HC. Increasing brain activity within the HC via therapy may reduce symptoms of Alzheimer's disease, such as memory loss.

The delivery of stimulation to the AN of brain 28 may be useful for managing a seizure disorder because the AN is a central site of the Circuit of Papez, and, as a result, stimulating the AN may help target a plurality of seizure foci that may be present in the Circuit of Papez even if the seizure focus is not in the AN. Such a relationship may help minimize the burden on a clinician in identifying a useful target stimulation site by locating the exact seizure focus. This can be referred to as a remote stimulation approach. Moreover, stimulating in the AN can be less invasive to the patient because the leads can be relatively easily implanted in the AN compared to, e.g., the HC, although leads can be implanted in the HC as well in some examples.

For some patients, the HC of brain 28 may be a seizure focus. Accordingly, for at least some of those patients, reducing a brain activity level within the HC may be desirable for managing a seizure disorder. The reduced brain activity level within the HC may help mitigate symptoms of the seizure disorder, such as by lowering likelihood of an occurrence of a seizure, reducing the severity or duration of seizures, and/or reducing the frequency of seizures. Stimulation (or another type of therapy) may be delivered directly to the AN rather than directly to the HC for various reasons, such as to reduce invasiveness of the therapy system. As described in further detail below with respect to FIG. 6-10, identifying an area within the AN that has a functional connection to the HC that results in the suppression of brain activity in the HC when stimulation is delivered to the area of the AN may be useful for selecting a target therapy delivery site and selecting a stimulation electrode combination with which IMD 16 delivers electrical stimulation to the AN. The relative strength of the functional connection between the AN and the HC is mapped using various devices, systems, and techniques described herein. The AN of brain 28 can be subdivided into a plurality of areas using any suitable technique. As discussed below with respect to FIGS. 11A-15 in some examples, an area of the AN is defined by a subset of electrodes and/or a lead position in the AN.

The level of a functional connection between the AN and the HC may be characterized by the effect of stimulation delivery on an area of the AN on the brain activity level within the HC. As illustrated in FIG. 5, regions within the Circuit of Papez may be connected to one another via neurological pathways such that activity within one region of brain 28 may affect activity within another region of brain 28. As such, electrical stimulation delivered from IMD 16 to a particular region of the Circuit of Papez may influence brain signals in one or more other regions of the Circuit of Papez. Due to, for example, the neural pathways between the different parts of brain 28, different areas within a first region (e.g., the AN) of the Circuit of Papez may have a different level of functional connection to a second region (e.g., the HC) of the Circuit of Papez, such that the effect of the stimulation delivery to the first region on the second region may depend on the part of the area of the first region to which stimulation is delivered. Accordingly, delivery of stimulation to different areas within the AN may have different effects on the level of brain activity within the HC. Thus, in some examples, the functional connectivity between the AN and HC is mapped by delivering stimulation to different areas within the AN and determining the resulting level of brain activity in the HC. An "area" of the AN (or another region of brain 28) has a volume less than the entire AN, such that the AN is made up of plurality of areas.

In some examples, a processor of a device (e.g., IMD 16 or programmer 14) can automatically select the target therapy delivery site within the AN is selected based on the mapping. For example, in one example, the processor selects the area of the AN that is associated with the desirable level of brain activity (e.g., the determined brain activity level or a change in the brain activity level) within the HC as a target therapy delivery site. As described above, the level of brain activity within the HC can be determined based on a bioelectrical brain signal sensed within the HC of brain 28 or within another region of brain 28 functionally related to HC, such as the AN of brain 28. In the case of a seizure disorder, suppression of brain activity within the HC via therapy may reduce the likelihood of a seizure by patient 12. Thus, for stimulation delivery to treat a seizure disorder of patient 12, it can be desirable in at least some examples to select an area within the AN that is associated with the lowest level of brain activity within the HC. In the case of stimulation delivery to manage Alzheimer's disease, on the other hand, it may be desirable in at least some examples to select an area within the AN that is associated with the highest level of brain activity within the HC.

In some existing techniques, a target therapy delivery site within brain 28 for treating a seizure disorder of patient 12 is selected by delivering a relatively low frequency stimulation (e.g., about 5 Hz) to a region of brain 28 and determining an evoked potential in a region believed to be the seizure focus. For example, in one technique, a relatively low frequency stimulation is delivered to an area of the AN of brain 28 and the local field potential in the HC evoked by the delivery of stimulation to the area of AN is determined. This local field potential sensed immediately following the delivery of stimulation to the area of AN can be referred to as the evoked potential (e.g., characterized by the peak amplitude of a sensed bioelectrical brain signal), which results when the brain activity in the thalamus propagates to the HC. Thus, the evoked potential is an excitatory response of the HC to the stimulation delivered to the thalamus; the relatively low frequency stimulation generates a spike in brain activity in the HC.

As discussed in further detail below, in some examples, the level of brain activity in the HC of brain 28 of patient 12 can be determined based on at least one characteristic of a sensed bioelectrical brain signal (e.g., sensed within the AN or HC), which can be a frequency domain characteristic or a time domain characteristic of the bioelectrical brain signal. Examples of a time domain characteristic include, but are not limited to, a mean, median, instantaneous, peak or lowest amplitude of the bioelectrical brain signal within a predetermined period of time. Examples of a frequency domain characteristic include, but are not limited to, a power level in one or more frequency bands of a bioelectrical brain signal (e.g., sensed within the AN or HC) sensed over a predetermined period of time or a ratio of power levels in at least two frequency bands of the bioelectrical brain signal.

In some currently proposed techniques, a target stimulation site within the thalamus is selected to be the area of the thalamus that resulted in the greatest evoked potential in the HC (e.g., the brain signal with the greatest average peak amplitude for a time period following the delivery of the stimulation to the thalamus). It is believed that the area of the thalamus that is associated with the greatest evoked potential has the strongest functional connection to the HC, such that delivery of stimulation to the area of the thalamus may provide efficacious stimulation therapy for managing the seizure disorder of patient 12.

While the selection of a target stimulation site based on an evoked potential sensed in the HC in response to the delivery of a relatively low frequency stimulation to the AN may be useful, the techniques described herein that include delivering a relatively high frequency (e.g., greater than about 80 Hz) stimulation to the AN and determining the area of the AN that resulted in the relatively greatest suppression of activity in the HC (i.e., the lowest brain activity level) are also useful for selecting a target stimulation site. The relatively high frequency stimulation is believed to better simulate stimulation therapy that is configured to treat the seizure disorder. That is, for some patients, an efficacious stimulation therapy includes delivering a stimulation signal that has a relatively high frequency. As a result, the mapping of the AN and HC that is based on the high frequency stimulation may better reflect the functional connectivity that is relevant to the stimulation therapy for managing a seizure disorder.

In addition, it is believed that the suppression of brain activity in the HC resulting from the delivery of the relatively high frequency stimulation to the AN may better correlate to the desired result of therapy to manage a seizure disorder. As a result, mapping the functional connectivity between different areas of the AN and the HC using the relatively high frequency stimulation may help better identify a target therapy delivery site within the AN that may lead to efficacious seizure disorder therapy for patient 12. As discussed above, in some examples, during therapy delivery to manage a seizure disorder, IMD 16 may deliver therapy to the brain 28 in a manner that influences the brain signals within the HC of brain 28. For example, IMD 16 can deliver therapy to AN of brain 28 via a selected subset of electrodes 24, 26 to lower the activity level in the HC.

The brain activity level within the HC may indicate, for example, the possibility of the onset of one or more symptoms of the patient condition. For example, brain activity levels can be associated with respective risks of the occurrence of a seizure event (e.g., the onset of seizure or the onset of a specific type of seizure, such as a seizure associated with a motor component). The level of brain activity within the HC of brain 28 can be indicated by, for example, one or more characteristics of a bioelectrical brain signal sensed within the HC. Example characteristics include, but are not limited to, a mean, median, peak-to-peak, instantaneous, or lowest amplitude of the signal, the variance of the signal over time, or a frequency domain characteristic (e.g., an energy level within one or more specific frequency bands) of the bioelectrical brain signal.

In addition, in some examples, the level of brain activity within the HC of brain 28 can be indicated by a characteristics of a bioelectrical brain signal sensed within the AN. As discussed below with respect to FIG. 9, it is believed that the brain activity within the AN following the delivery of stimulation to the AN may reflect the brain activity within the HC, such that a bioelectrical brain signal sensed within the AN can be used as a surrogate for a bioelectrical brain signal sensed within the HC.

The techniques for selecting one or more target therapy delivery sites based on a brain activity level within the HC in response to therapy delivery to the AN may be used during a implantation of leads 20 to select an initial implantation site for leads 20 or during follow-up programming of therapy system 10, e.g., to change the target therapy delivery site by selecting a different subset of electrodes 24, 26 for delivering therapy to patient 12. The follow-up programming of therapy system 10 may take place automatically or semi-automatically (e.g., initiated and/or authorized by a user). Various factors may render the reselection of a target therapy delivery site for patient 12 or the adjustment of the electrodes that are used to deliver stimulation to brain 28 desirable. For example, leads 20 may migrate from an initial target stimulation site within patient 12 and/or the patient condition or disorder may progress, regress or otherwise change during the course of therapy delivery by IMD 16. Therefore, periodically changing the target stimulation site and/or the subset electrodes 24, 26 that are used to deliver therapy to patient 12 can be useful to accommodate any changes in the patient condition that may benefit from such a change in a therapy delivery site.

In addition, in some examples, in addition to, or instead of selecting a target therapy delivery site and subsequently selecting a stimulation electrode combination based on the selected target therapy delivery site, an stimulation electrode combination may be directly selected based on the mapping between different areas of the AN and the HC. For example, the stimulation electrode combination that results in the most suppression of activity in the HC may be selected as the stimulation electrode combination. In some examples, processor 80 of programmer 14 or another device may automatically select the target therapy delivery site or stimulation electrode combination (and sense electrode combination in some examples) based on the mapping between the AN and HC of brain 28 using the techniques described herein.

Figure 6:
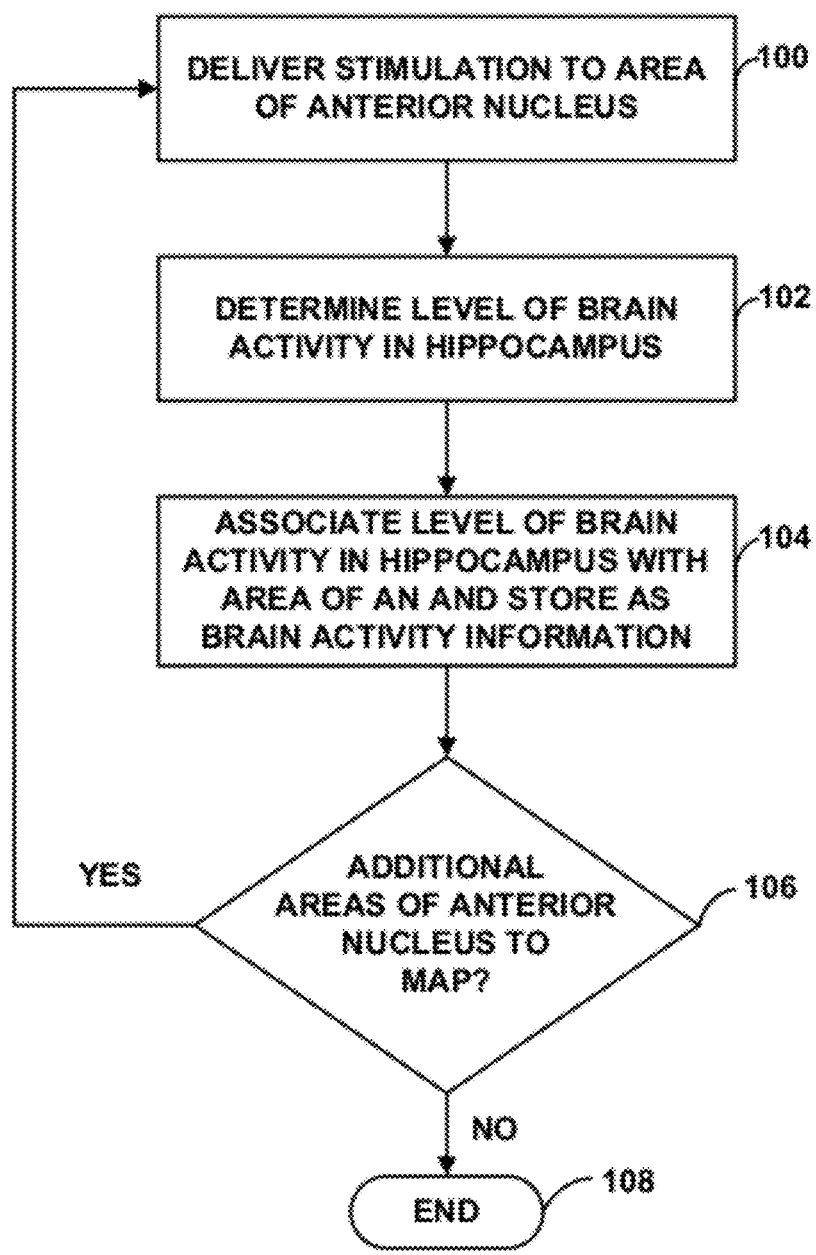
FIG. 6 is a flow diagram illustrating an example technique for mapping functional connections between a plurality of areas within an anterior nucleus of a thalamus of a brain and a hippocampus of the brain.

FIG. 6 is a flow diagram illustrating an example technique for mapping the relative functional connection between each area of plurality of areas within the AN to the HC using a relatively high frequency stimulation. While the technique shown in FIG. 6, as well as the other figures are described with respect to processor 60 of IMD 16, in other examples, a processor of another device, such as processor 80 of programmer 14 (FIG. 4) can perform any part (e.g., part or all) of the techniques described herein, alone or in combination with another device.

In accordance with the technique shown in FIG. 6, processor 60 of IMD 16 controls stimulation generator 64 to generate and deliver a relatively high frequency stimulation signal to an area of AN of brain 28 of patient 12 (100). The stimulation signal may have a frequency of greater than or equal to about 80 Hz, such as a frequency in a range of about 80 Hz to about 160 Hz. Thereafter, and prior to delivery of any further stimulation to brain 28, processor 60 determines a level of brain activity in the HC of brain 28 that results from the delivery of stimulation to the area of the AN (102). Processor 60 determines the level of brain activity (e.g., based on a sensed bioelectrical brain signal, such as a local field potential) in the HC while any effects of the stimulation delivery to the area of the AN are still observed, such as within about one minute from the end of the stimulation delivery to the area of the AN, although other time ranges can be used. In some cases, processor 60 may continue monitoring the level of brain activity until the brain activity returns to a baseline state, e.g., within about 6 to about 10 minutes, such as about 6 minutes to about 7 minutes, although it may take longer or shorter than about 6 minutes to about 7 minutes for the brain activity in the HC to return to a baseline state.

As discussed in further detail below with respect to FIGS. 7 and 8, in some examples, processor 60 determines the level of brain activity in the HC based on a bioelectrical brain signal sensed within the HC, while in other examples, processor 60 determines the levels of brain activity in the HC based on a bioelectrical brain signal sensed within the AN, such as a local field potential.

As discussed in further detail below, in some examples, processor 60 determines the level of brain activity in the HC based on at least one characteristic of a sensed bioelectrical brain signal (e.g., sensed within the AN or HC), which can be a frequency domain characteristic or a time domain characteristic of the bioelectrical brain signal. Examples of a time domain characteristic include, but are not limited to, a mean, median, peak or lowest amplitude of the bioelectrical brain signal within a predetermined period of time. Examples of a frequency domain characteristic include, but are not limited to, a power level in one or more frequency bands of a bioelectrical brain signal (e.g., sensed within the AN or HC) sensed over a predetermined period of time or a ratio of power levels in at least two frequency bands of the bioelectrical brain signal.

Processor 60 associates the determined level of brain activity in HC with the area of the AN to which the stimulation was delivered, and stores the level of brain activity in the HC and the associated area of the AN as brain activity information 76 in memory 62 of IMD 16 (FIG. 3) or a memory of another device (104). With this information, processor 60 can map the area of the AN of brain 28 with the HC of brain 28 because the level of brain activity in the HC resulting from the delivery of stimulation to the area of the AN provides a relative indication of the functional connectivity between the area of the AN and the HC. The level of brain activity in the HC resulting from the delivery of stimulation to the area of the AN can be determined while the stimulation is being delivered to the area of the AN or after termination of the delivery of stimulation to the area of the AN (while no stimulation is being delivered to the AN). The mapping of a plurality of areas of the AN with the HC can provide a clinician with useful information, such as relative strengths of the functional connection between the different areas of the AN and the HC. The brain activity level within the HC that is associated with an area of the AN can indicate, for example, whether the relatively high frequency stimulation delivered to the area of the AN had a suppressive effect on the brain activity within the HC, and, in some cases, a relative magnitude of the suppressive effect (e.g., a value that enables the clinician to compare the suppressive effect between the different areas of the AN).

In order to select a target therapy delivery site within brain 28, it can be desirable to deliver stimulation to each area of a plurality of areas within AN of brain 28 (at different times), and, for each area of the AN to be mapped, determine the brain activity level in the HC resulting from the delivery of the stimulation to the respective area. The areas of the AN can be predetermined and stored by memory 62 of IMD 16, memory 82 of programmer 14 (FIG. 4), or a memory of another device. As discussed below with respect to FIGS. 11A-15 each area of the AN can correspond to a different position (e.g., a different depth level relative to cranium 32 of patient 12) of leads 20 implanted within the AN. In other examples, each area of the AN of brain 28 can correspond to a different subset of electrodes 24, 26 that are implanted in the AN. Other ways of subdividing AN into a plurality of different areas are contemplated.

In accordance with the technique shown in FIG. 6, after determining the first level of brain activity in the HC of brain 28 and storing the information in memory 62, processor 60 determines whether there are any additional areas of the AN to map (106). If there are not any additional areas of the AN to map, processor 60 ends the mapping technique (108). On the other hand, in response to determining there are additional areas to map, processor 60 controls stimulation generator 64 to generate and deliver a relatively high frequency stimulation to another area of AN (100) and, prior to delivery of any further stimulation to brain 28, processor 60 determines a level of brain activity in the HC of brain 28 (102). For each area of the AN to be mapped, processor 60 associates the determined level of brain activity in HC with the area of the AN to which the stimulation was delivered, and stores the level of brain activity in the HC and the associated area of the AN as brain activity information 76 in memory 62 of IMD 16 (FIG. 3) or a memory of another device (104). Processor 60 performs the technique shown in FIG. 6 to map at least two different areas of the AN, such that the functional connection between the HC and at least two different potential therapy delivery sites in the AN may be compared.

Figure 7:
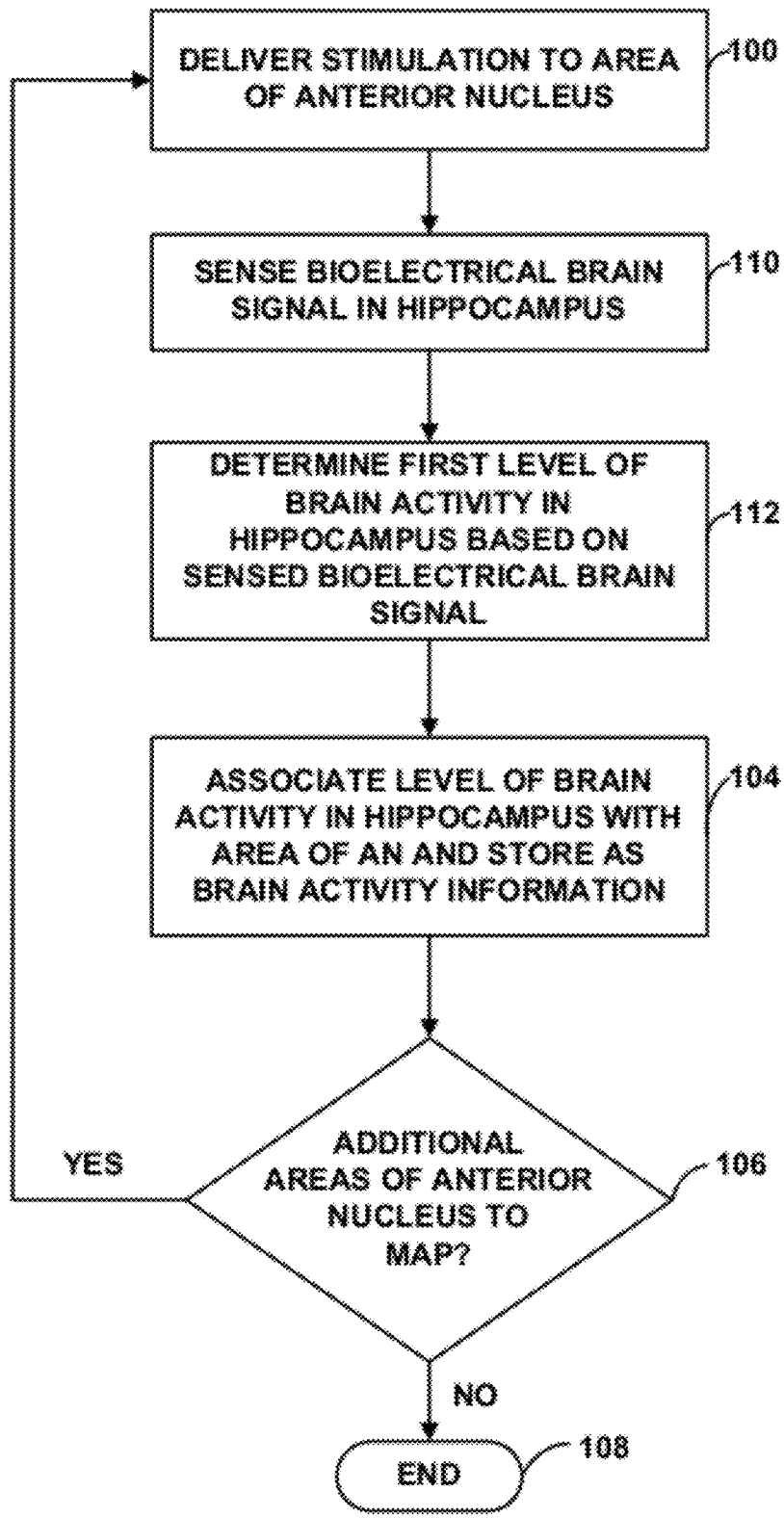
FIGS. 7 and 8 are flow diagrams of examples of the technique shown in FIG. 6 in more detail.

FIG. 7 is a flow diagram of an example of the technique shown in FIG. 6. In particular, FIG. 7 provides an example technique for determining the level of brain activity In the HC. In the example technique shown in FIG. 7, processor 60 controls stimulation generator 64 to generate and deliver stimulation to an area of the AN of brain 28 of patient 12 (100), and processor 60 controls sensing module 66 to sense a bioelectrical brain signal within the HC of brain 28 of patient 12 (110). Sensing module 66 senses the bioelectrical brain signal at a time that is relevant to determining the effect of the stimulation to the area of the AN on brain activity in the HC. Sensing module 66 can begin sensing bioelectrical brain signal within the HC at any suitable time, such as after the delivery of stimulation to the area of the AN of brain 28 has been initiated, or, in some cases, after stimulation generator 64 terminates the delivery of stimulation to the area of the AN of brain 28. In other examples, sensing module 66 may sense the bioelectrical brain signal within the HC prior to and during the delivery of stimulation to AN of brain 28 (100).

Processor 60 determines a first level of brain activity in the HC based on the sensed bioelectrical brain signal (112). The relevant brain activity level is the activity level in the HC that is generated in response to the delivery of stimulation to the area of the AN (100). Accordingly, in some examples, processor 60 determines a level of brain activity in the HC based on a bioelectrical brain signal sensed after the initiation of the delivery of the stimulation to the area of the AN, and within a predetermined period of time after the termination of the delivery of stimulation to the area of the AN. The predetermined period of time can be, for example, about 1 second, and can be selected by a clinician and stored by memory 62 of IMD 16 or a memory of another device (e.g., programmer 14) prior to the mapping technique shown in FIG. 7 is initiated.

In some examples, processor 60 determines the level of brain activity in the HC of brain 28 of patient 12 based on at least one characteristic of the bioelectrical brain signal, which can be a frequency domain characteristic or a time domain characteristic of the bioelectrical brain signal. For example, the level of brain activity within the HC of brain 28 of patient 12 can be indicated by the average, peak-to-peak, peak, median or instantaneous amplitude of a bioelectrical brain signal sensed within the HC over a predetermined period of time (e.g., the average amplitude over about one second to about five minutes following the delivery of stimulation to the area of the AN) or the peak-to-peak variability of the bioelectrical brain signal. As other examples, the level of brain activity within the HC of brain 28 of patient 12 can be indicated by the variance between the instant, median, or mean amplitude of a bioelectrical brain signal over time, where the variance may be between subsequent slots of time or between a sensed bioelectrical brain signal and a stored average, peak, median or instantaneous of the amplitude determined based on a prior period of time.

As other examples, processor 60 may determine the level of brain activity in the HC of brain 28 of patient 12 based on a frequency domain characteristic of the bioelectrical brain signal. The frequency domain characteristic can be determined based on, for example, a spectral analysis of a bioelectrical brain signal. The spectral analysis may indicate the distribution over frequency of the power contained in a signal, based on a finite set of data.

In some examples, the frequency domain characteristic may comprise a relative power level in a particular frequency band or a plurality of frequency bands. While "power levels" within a selected frequency band of a sensed bioelectrical brain signal are generally referred to herein, the power level may be a relative power level. A relative power level may include a ratio of a power level in a selected frequency band of a sensed brain signal to the overall power of the sensed brain signal. The power level in the selected frequency band may be determined using any suitable technique. In some examples, processor 60 of IMD 16 may average the power level of the selected frequency band of a sensed brain signal over a predetermined time period, such as about ten seconds to about two minutes, although other time ranges are also contemplated. In other examples, the selected frequency band power level may be a median power level over a predetermined range of time, such as about ten seconds to about two minutes. The activity within the selected frequency band of a brain signal, as well as other frequency bands of interest, may fluctuate over time. Thus, the power level in the selected frequency band at one instant in time may not provide an accurate and precise indication of the energy of the brain signal in the selected frequency band. Averaging or otherwise monitoring the power level in the selected frequency band over time may help capture a range of power levels, and, therefore, a better indication of the patient's pathological state in the particular brain region sensed by IMD 16.

The overall power of a sensed bioelectrical brain signal may be determined using any suitable technique. In one example, processor 60 of IMD 16 (or another device, such as programmer 14) may determine an overall power level of a sensed bioelectrical brain signal based on the total power level of a swept spectrum of the brain signal. To generate the swept spectrum, processor 60 may control sensing module 66 to tune to consecutive frequency bands over time, and processor 60 may assemble a pseudo-spectrogram of the sensed bioelectrical brain signal based on the power level in each of the extracted frequency bands. The pseudo-spectrogram may be indicative of the energy of the frequency content of the bioelectrical brain signal within a particular window of time.

After determining the level of brain activity in the HC based on the sensed bioelectrical brain signal (112), processor 60 associates the level of the brain activity with the area of the AN and stores level of brain activity in the HC of brain 28 and the associated area of the AN in memory 62 of IMD 16 as brain activity information 76 or in a memory of another device (e.g., programmer 14) (104). In some cases, the stored brain activity level can be a value of a characteristic of the bioelectrical brain signal sensed in the HC (e.g., an amplitude value or a value of a frequency domain characteristic). In addition or instead, processor 60 can store the bioelectrical brain signal sensed in the HC as the brain activity level. The stored signal can include, for example, a raw bioelectrical brain signal sensed by sensing module 66 of IMD 16 (or another sensing module), a parameterized bioelectrical brain signal generated by sensing module 66 or data generated based on the raw bioelectrical brain signal, such as a signal characteristic extracted from the sensed bioelectrical brain signal.

As with the technique shown in FIG. 6, after determining the level of brain activity in the HC of brain 28 and storing the information in memory 62, processor 60 determines whether there are any additional areas of the AN to map (106). If there are not any additional areas of AN to map, processor 60 ends the mapping technique (108). On the other hand, if there are additional areas to map, processor 60 repeats the technique shown in FIG. 7 for each additional area of the AN.

Figure 8:
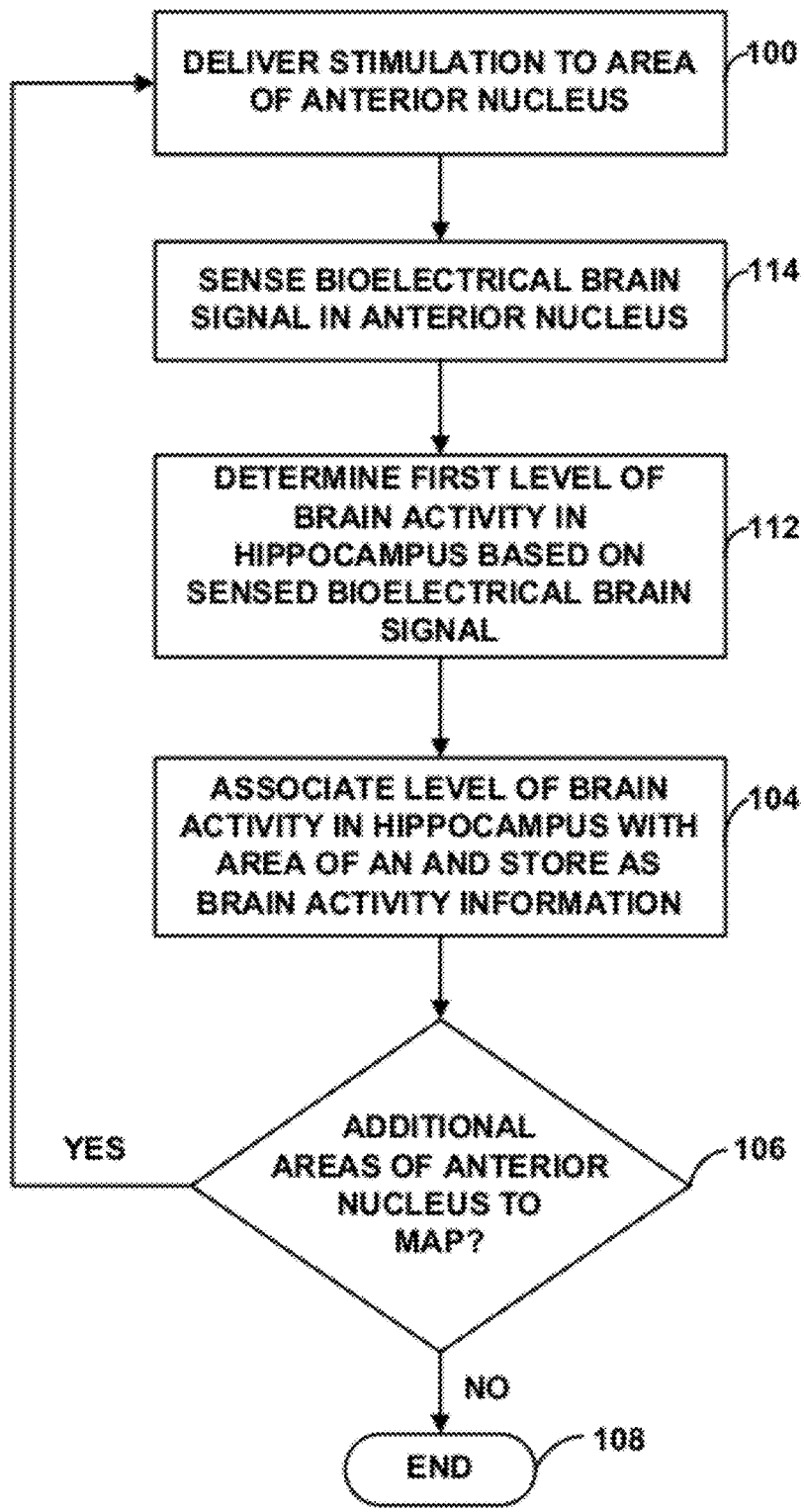

FIG. 8 is a flow diagram of another example of the technique shown in FIG. 6. The technique shown in FIG. 8 is similar to the technique shown in FIG. 7, but instead of sensing a bioelectrical brain signal in the HC (110) and determining a level of brain activity in the HC based on a bioelectrical brain signal sensed in the HC (112), processor 60 controls sensing module 66 to sense a bioelectrical brain signal within the AN of brain 28 of patient 12 (114) and determines the level of brain activity in the HC based on a bioelectrical brain signal sensed in the AN (112). Based on at least observations discussed below with respect to FIGS. 16A-17E, it is believed that brain activity in the AN following the delivery of high frequency stimulation (e.g., greater than about 80 Hz) to the AN may reflect the brain activity in the HC. Thus, in the example technique shown in FIG. 8, the brain activity in the AN of brain 28 of patient 12 after the delivery of relatively high frequency stimulation to the AN is used as a surrogate for the brain activity in HC of patient 12.

The bioelectrical brain signal sensed in the AN (114) can be, for example, sensed in the same area in which the electrical stimulation was delivered. In other examples, the bioelectrical brain signal sensed in the AN (114) is sensed in a different area from the area to which the electrical stimulation was delivered.

The same techniques described above with respect to determining a level of brain activity in the HC based on a bioelectrical brain signal sensed in the HC can be used to determine the level of brain activity in the HC based on a bioelectrical brain signal sensed in the AN.

Figure 9:
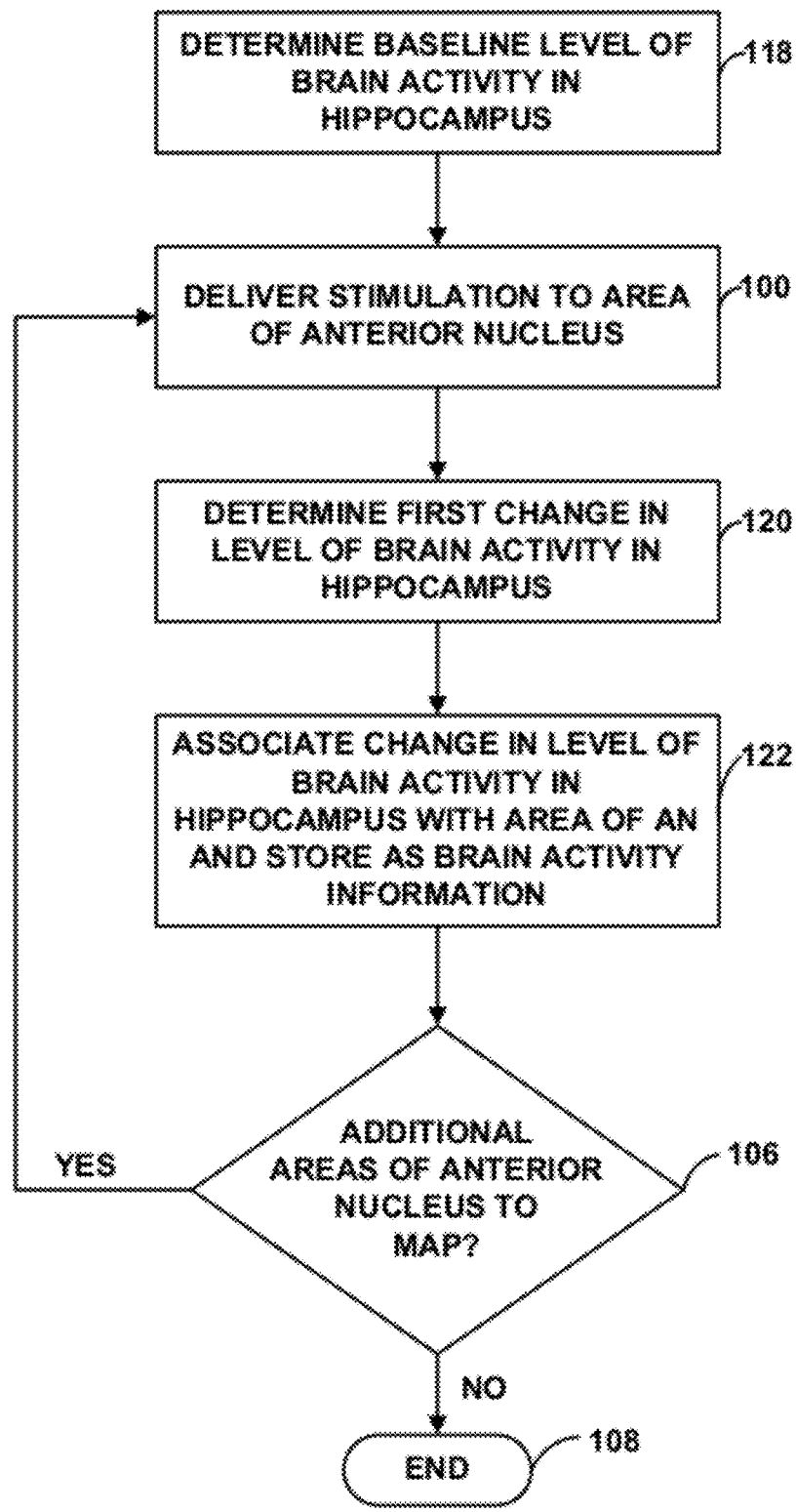
FIG. 9 is a flow diagram of an example technique for mapping a plurality of areas within an anterior nucleus of a thalamus of a brain to the hippocampus of the brain, where the mapping associates each area of the plurality of areas of the anterior nucleus of a thalamus with a change in the level of brain activity in the hippocampus relative to a baseline level of brain activity in the hippocampus.

In some examples, a level of brain activity in the HC associated with an area of the AN during mapping of the AN to the HC can include a characteristic of the bioelectrical brain signal (e.g., an amplitude or a frequency domain characteristic), as discussed above with respect to FIG. 6. In addition, in some examples, the level of brain activity in the HC associated with an area of the AN during mapping can be a change in the level of brain activity in the HC relative to a baseline level of brain activity in the HC. FIG. 9 is a flow diagram of a technique for mapping a plurality of areas of the AN to the HC, where the mapping associates each area of the plurality of areas of the AN with a change in the level of brain activity in the HC relative to a baseline level of brain activity in the HC.

In accordance with the technique shown in FIG. 9, processor 60 of IMD 16 determines the baseline level of brain activity in the HC of brain 28 of patient 12 based on one or more characteristics of a sensed bioelectrical brain signal that is indicative of activity in the HC (118). If the activity in the HC is determined based on a bioelectrical signal sensed within the HC (e.g., as discussed with respect to FIG. 7), processor 60 may determine the baseline brain activity level based on one or more characteristics of a bioelectrical brain signal sensed within the HC. On the other hand, if the activity in the HC is determined based on a bioelectrical sensed within the AN (e.g., as discussed with respect to FIG. 8), processor 60 may determine the baseline brain state of patient 12 based on one or more characteristics of a bioelectrical brain signal sensed within the AN. In some examples, processor 60 stores an indication of the baseline brain activity level within the HC as brain activity information 76 in memory 62 of IMD 16 or a memory of another device (e.g., programmer). The activity level may be stored as, for example, a raw bioelectrical brain signal sensed by sensing module 66 of IMD 16 (or another sensing module), a parameterized bioelectrical brain signal generated by sensing module 66 or data generated based on the raw bioelectrical brain signal, such as a signal characteristic extracted from the sensed bioelectrical brain signal.

Processor 60 may determine the baseline level of brain activity in the HC of patient 12 based on a bioelectrical brain signal that indicates brain activity known or believed by a clinician to be unaffected by delivery of stimulation therapy from stimulation generator 64 of IMD 16. The baseline level of brain activity can be, for example, the activity level within the HC in the absence of therapy for treating the patient condition. Thus, in some examples, processor 60 can determine the baseline level of brain activity within the HC of brain 28 of patient 12 prior to any delivery of stimulation by IMD 16 or after a washout period resulting from the stimulation delivery (e.g., after any carryover effects from stimulation therapy have substantially or completely dissipated). In some cases, the baseline brain activity level may represent the patient condition that is undesirable (e.g., a brain state in which one or more symptoms associated with the patient disorder to be treated via therapy are observed or a brain state in which a patient event is likely to occur). The baseline level of brain activity within the HC can be determined based on a bioelectrical brain signal sensed over any suitable duration, such as, but not limited to, about three minutes to about five minutes.

Processor 60 may identify one or more characteristics of a sensed bioelectrical brain signal and store the identified characteristic(s) as indicators of the baseline brain activity level. For example, the baseline brain activity level within the HC can be indicated by the average, peak-to-peak, peak, median or instantaneous amplitude of a bioelectrical brain signal sensed within the HC or AN over a predetermined period of time (e.g., the average amplitude over a period of time of about one second to about five minutes), the variability of the bioelectrical brain signal over time, a frequency domain characteristic (e.g., a relative power in a particular frequency band or a ratio of power levels), or a variability of one or more frequency domain characteristics (e.g., the average, peak, mean or instantaneous energy level within a selected frequency band over predetermined period of time) over time.

After determining the baseline level of brain activity in the HC (118), processor 60 can control stimulation generator 64 of IMD 16 to generate and deliver stimulation to an area of the AN (100), as described with respect to the technique shown in FIG. 6. In the example shown in FIG. 9, processor 60 determines a change in the level of brain activity in the HC after the delivery of stimulation to the area of the AN (120), which is indicative of the strength of the functional connection between the area of the AN and the HC. The change in the level of brain activity in the HC can be determined, for example, based on a bioelectrical brain signal sensed within the HC or AN at a time after the initiation of the stimulation delivery to the area of the AN, e.g., immediately after the initiation of the stimulation of delivery to the area of the AN, and ending at some time prior to delivery of stimulation to another area of the AN. Moreover, the level of brain activity within the HC can be determined based on a bioelectrical brain signal sensed within the AN and/or HC after termination of the electrical stimulation to the area of the AN or while the electrical stimulation is still being delivered to the area of the AN.

The change in the level of brain activity in the HC after the delivery of stimulation to the area of the AN can be, for example, a percentage change of the brain activity level relative to the baseline brain activity level, a gross value indicative of the change the brain activity level relative to the baseline brain activity level, or any combination thereof. For example, if the level of brain activity in the HC is indicated by an amplitude of a bioelectrical brain signal, the change in the level of brain activity in the HC resulting from the delivery of stimulation to the area of the AN can be a difference between the baseline amplitude and the amplitude of the sensed within the HC over a predetermined duration of time following the delivery of stimulation to the AN.

After determining a change in the level of brain activity in the HC after the delivery of stimulation to the area of the AN (120), processor 60 associates the change in the level of brain activity in the HC with the area of the AN to which the stimulation was delivered to effect the change (122). Processor 60 can store the level of brain activity in the HC and the associated area of the AN to which the stimulation was delivered to effect the change in memory 62 of IMD 16 as brain activity information 76 or in a memory of another device. As with the technique shown in FIG. 6, after associating the change in the level of brain activity in the HC with the area of the AN to which the stimulation was delivered to effect the change, processor 60 can determine whether there are any additional areas of the AN to map (106). In response to determining there are not any additional areas of AN to map, processor 60 ends the mapping technique (108). On the other hand, in response to determining there are additional areas to map, for each additional area of the AN to map, processor 60 can repeat the technique that includes delivering stimulation to a different area of the AN (100), determining a change in the level of brain activity in the HC resulting from the delivery of stimulation, and associating and storing the change in the level of brain activity in the HC with the area of the AN.

In some examples, the baseline brain activity level in the HC can be established prior to delivery of stimulation to another area of the AN, such that for at least two areas of the AN (e.g., each area of the plurality of areas being mapped), there is a different baseline brain activity level. However, in other examples, the same baseline brain activity level can be used to map the plurality of areas of the AN to the HC using the technique shown in FIG. 9.

As discussed above, in some examples, after the relative strength of the functional connections between a plurality of areas of the AN and the HC are mapped, e.g., using the techniques described with respect to FIGS. 6-9, a target therapy delivery site or stimulation electrode combination can be selected based on the information provided by the mapping. The information provided by the mapping includes, for example, an indicator of a level of brain activity (e.g., a bioelectrical brain signal or a specific characteristic extracted from the bioelectrical brain signal) associated with the delivery of stimulation to the area of the AN.

Figure 10:
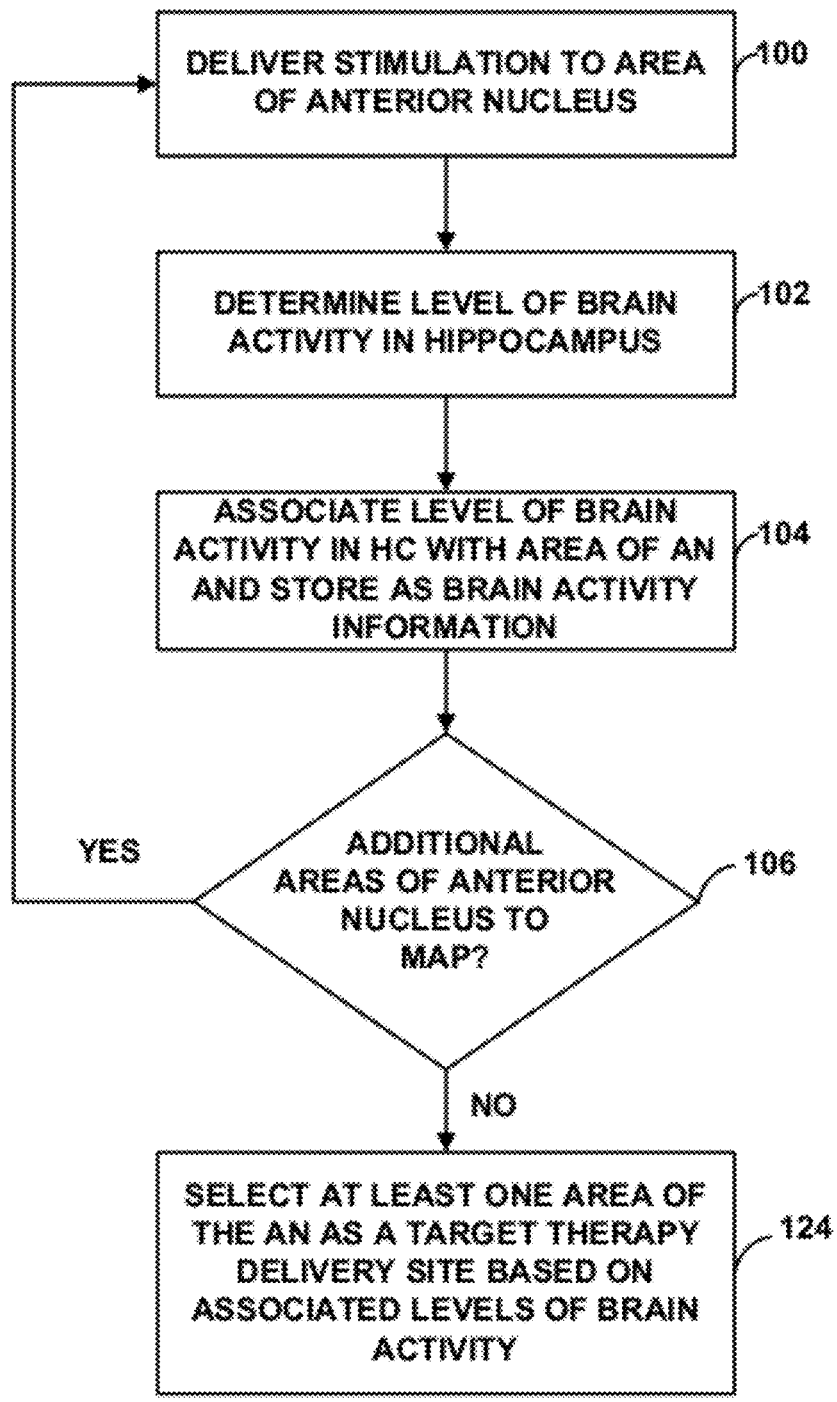
FIG. 10 is a flow diagram of an example technique that can be used to select a target therapy delivery site after mapping a plurality of areas within an anterior nucleus of a thalamus of a brain to the hippocampus of the brain.

FIG. 10 is a flow diagram of an example technique that can be used to select a target therapy delivery site after mapping a plurality of different areas the AN area to HC. In accordance with the technique shown in FIG. 10, for each area of an AN to be mapped, processor 60 controls stimulation generator 64 to deliver a relatively high frequency stimulation to the respective area of the AN (100), determines a level of brain activity in the HC resulting from the stimulation (102), associates the level of brain activity in the HC with the area of the AN and stores the level of brain activity in the HC and associated area of the AN in memory 62 of IMD 16 or another device (104). Thereafter, processor 60 selects at least one of the areas of the AN as a target therapy delivery site based on the brain activity levels associated with the areas of the AN (124).

In some examples, processor 60 selects the area of the AN associated with the lowest brain activity level in the HC relative to the other areas of the AN that have been mapped as the target therapy delivery site. The lowest relative brain activity level in the HC may indicate, for example, that the associated area of the AN has a relatively meaningful functional connection (relative to the other areas of the AN that were mapped) with the HC, which may result in a efficacious delivery of stimulation to the AN to suppress brain activity in the HC. As discussed above, in the case of a seizure disorder, it can be desirable to suppress brain activity in the HC to manage the seizure disorder. It is believed that such suppression of brain activity in the HC may help to suppress cortical excitability, which may help treat seizure disorders, such as by reducing the possibility of an onset of a seizure, by reducing a duration or severity of a seizure, and/or by reducing the frequency of seizures.

In other examples, rather than automatically selecting the area of the AN as a target therapy delivery site, processor 60 may transmit the stored brain activity information 76 (e.g., the brain activity levels and associated areas of the AN) to programmer 14 or another computing device. Processor 80 of programmer 14 (FIG. 4) can then generate a display that provides information about a plurality of areas of the AN and, for each area of the AN, a metric indicative of the relative brain activity level within the HC resulting from the delivery of stimulation to the area, and present the display to a clinician via a display of user interface 86. A clinician may then select the target therapy delivery site based on the brain activity information. An example user interface is shown and described with respect to FIGS. 23-25.

As described above, an area within the AN may correspond to different electrodes 24, 26 on leads, such that different subsets of electrodes may be positioned in respective areas within the AN, and/or different positions of leads 20 within the AN of brain 28. In some examples, in order to map a plurality of areas within the AN with the HC, the stimulation can be delivered to each area of the plurality of areas by changing a position of one or both leads 20 within the AN. In other examples, in order to map a plurality of areas within the AN with the HC, the stimulation can be delivered to each area of the plurality of areas by changing the electrodes 24, 26 with which IMD 16 delivers electrical stimulation to the AN, while the leads 20 remain in one position. In addition, in other examples, a combination of changing the position of one or both leads 20 and stimulation electrode combination with which IMD 16 uses to deliver stimulation to the AN can be used to amp the plurality of areas in the AN with the HC.

Figure 11A:
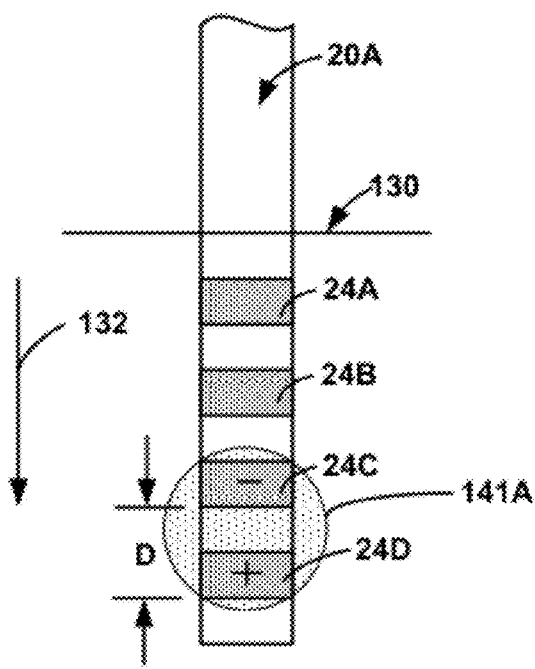
FIGS. 11A and 11B are schematic illustrations of an implantable lead at different positions within an anterior nucleus of a thalamus of a brain of a patient.
Figure 11B:
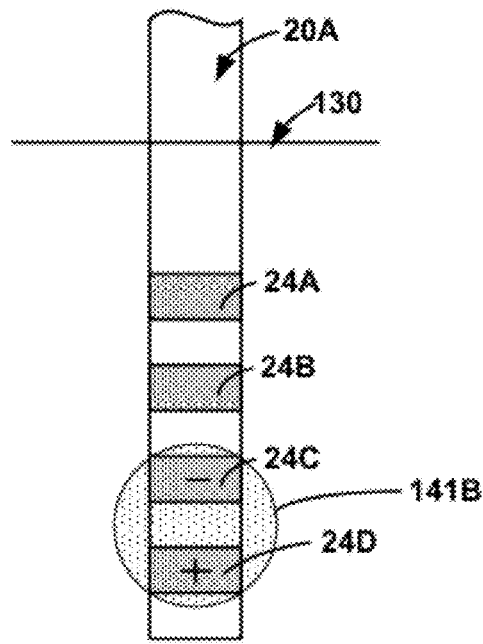

FIGS. 11A and 11B are schematic illustrations of lead 20A at different positions within the AN of brain 28 of patient 12. One lead 20A is shown in FIGS. 11A and 11B for ease of description. In FIG. 11A, lead 20A is at a first position within the AN, where the position can be defined with respect to an arbitrary point or with respect to an anatomical landmark, such as cranium 32 (FIG. 1) of patient 12 or a ventricle of brain 28 of patient 12. In the example shown in FIGS. 11A and 11B, the position of lead 20A is described with respect to line of reference 130, which can be arbitrary or can be associated with a known anatomical landmark (e.g., an inner or outer surface of cranium 32) within patient 12. Arrow 132 indicates a deep direction, which is an anatomical direction that points further away from the surface (e.g., cranium 32 or skin) of patient 12. Thus, the direction opposite arrow 132 is a superficial direction. In the first position of lead 20A, shown in FIG. 11A, electrode 24D is positioned at a first depth relative to line of reference 130.

In a second position of lead 20A, shown in FIG. 11B, electrode 24D is positioned at a second depth relative to line of reference 130, where the second depth is deeper than the first depth. In this way, when lead 20A is moved from the first position shown in FIG. 11A to the second position shown in 11B, electrodes 24 are also shifted in the deep direction. If each of the electrodes 24 has substantially the same length (measured in a direction substantially parallel to a longitudinal axis of lead 20A and in the deep direction shown in FIG. 11A), and lead 20A is moved in the deep direction by a distance D that is substantially equal to the total length of an electrode 24 and the space between adjacent electrodes 24 in order to move lead 20A from the first position (FIG. 11A) to the second position (FIG. 11B), in the second position of lead 20A, electrode 24C is positioned at the first depth, at which electrode 24D was positioned when lead 20A was in the first position. In some examples, distance D is about 2 millimeters (mm), although other distances are contemplated and depend on the type of lead that is implanted in patient 12.

Although electrode 24D (which is a distal most electrode of lead 20A in the example shown in FIGS. 11A and 11B) is shown as an anode, in other examples, in order to map the functional connections between a plurality of areas of the AN and the HC, electrode 24D can be designated a cathode and another electrode can be designated as the anode.

Figure 12:
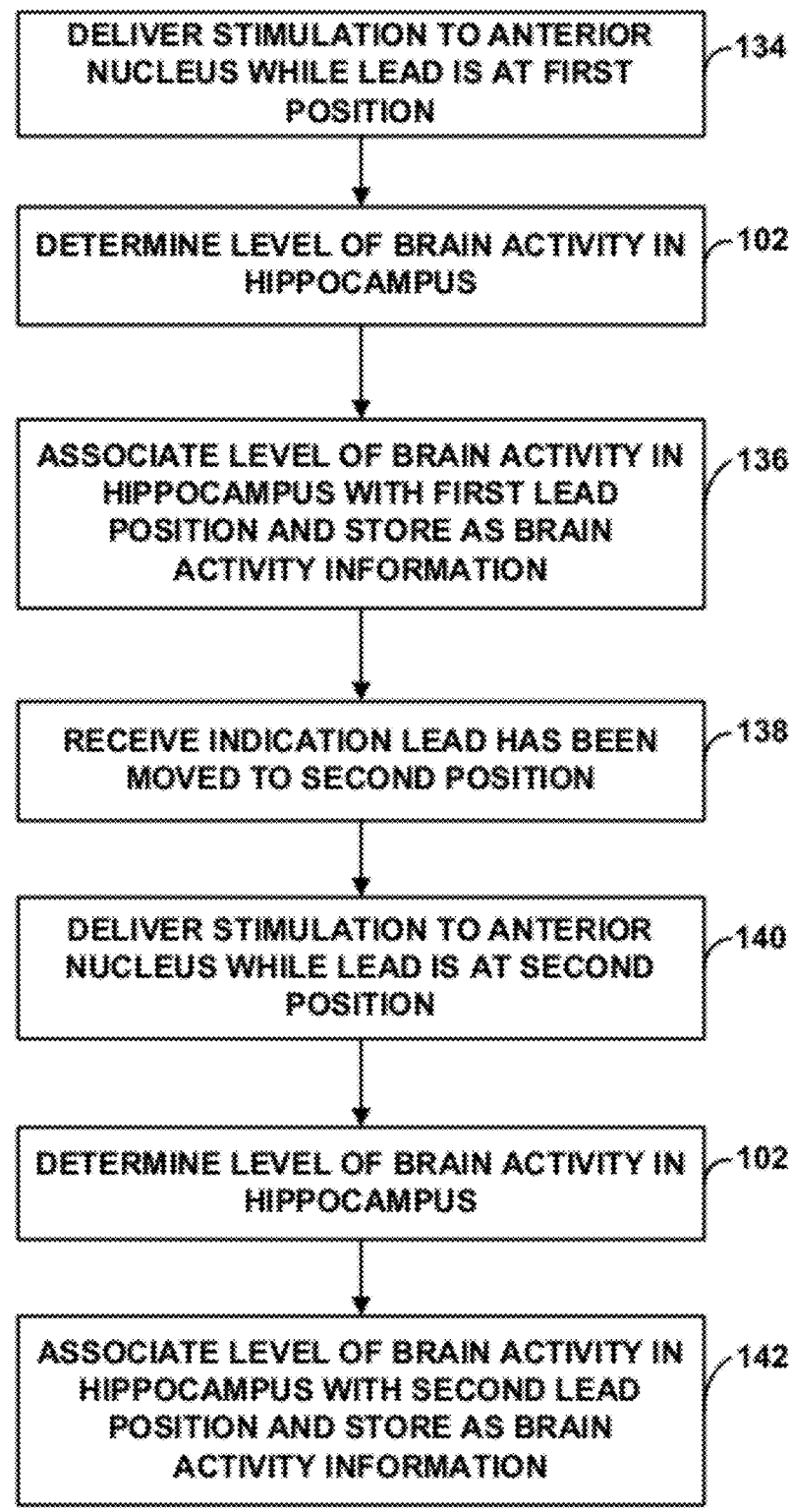
FIG. 12 is a flow diagram of an example technique for mapping the functional connections between a plurality of different areas of an anterior nucleus of a thalamus of a brain and the hippocampus, where each area of the anterior nucleus corresponds to a different lead position.

FIG. 12 is a flow diagram of an example technique for mapping the functional connectivity between a plurality of different areas of the AN with the HC, where each area of the AN corresponds to a different lead position. While FIG. 12, as well as FIGS. 11A, 11B, 14, and 15 are described with respect to a position of a single lead 20A, in other examples, the techniques described herein can be used with more than one lead, such as lead 20B in addition to lead 20A. In the example shown in FIG. 12, while lead 20A is at a first position, processor 60 of IMD 16 controls stimulation generator 64 to generate and deliver a relatively high frequency stimulation (e.g., greater than or equal to about 80 Hz) to the AN of brain 28 of patient 12 via a subset of electrodes 24 (134). The stimulation is delivered to a first area of AN, which corresponds to the first position of lead 20A, as well as the position of the subset of electrodes on lead 20A.

Processor 60 determines the level of brain activity in the HC of brain 28 that results from the delivery of stimulation to the AN of brain 28 of patient 12 when lead 20A is in the first position (102), e.g., using the techniques discussed above with respect to FIG. 6. Processor 60 then associates the level of brain activity in the HC with the first lead position (which corresponds to a particular area of the AN), and stores the level of brain activity in the HC and the associated lead position in memory 62 of IMD 16 as brain activity information 76 (136). Instead of, or in addition to, storing the level of brain activity in the HC and the associated lead position in memory 62 of IMD 16, processor 60 can store the information in a memory of another device, such as programmer 24.

After mapping the area of the AN of brain 28 associated with the first position of lead 20A with the HC, processor 60 maps another area of the AN with HC. In the example shown in FIG. 12, processor 60 receives an indication that lead 20A has been moved to a second position that is different than the first position. The indication can be, for example, a signal that is transmitted to processor 60 from programmer 14 via the respective telemetry modules 70, 84 (FIGS. 3 and 4, respectively). A user, such as a clinician, may interact with programmer 14 via user interface 86 (FIG. 4) after lead 20 is manually moved or moved with the aid of a device (e.g., a computer controlled device). Upon receiving the user input, processor 80 of programmer 14 (FIG. 4) can transmit the indication that lead 20A has been moved to a second position to processor 60 of IMD 16 via the respective telemetry modules 84, 70.

While lead 20A is at the second position, processor 60 of IMD 16 controls stimulation generator 64 to generate and deliver a relatively high frequency stimulation (e.g., greater than or equal to about 80 Hz) to the AN of brain 28 of patient 12 via the same subset of electrodes 24 that was used to deliver stimulation while lead 10A was at the first position (140). The stimulation is delivered to a second area of AN, which corresponds to the second position of lead 20A, as well as the position of the subset of electrodes on lead 20A. The second area of AN is different than the first area of AN because, as a result of the movement of lead 20A, the subset of electrodes are positioned to deliver stimulation to a different portion of AN.

For example, referring to FIGS. 11A and 11B, if electrodes 24C, 24D define the subset of electrodes that are used to deliver stimulation when lead 20A is at the first and second positions, electrodes 24C, 24D are at a different depth when lead 20A is moved to the second position (FIG. 11B) from the first position (FIG. 11A). As shown in FIG. 11A, when electrodes 24C, 24D are at a first depth, stimulation delivered via electrodes 24C, 24D may activate a first area 141A of AN. As shown in FIG. 11B, when electrodes 24C, 24D are at a first depth, stimulation delivered via electrodes 24C, 24D may activate a second area 141B of AN. First and second areas 141A, 141B, which may define a volume of tissue, may partially overlap, but do not completely overlap. In this way, moving lead 20A but delivering stimulation via the same subset of electrodes can result in the delivery of stimulation to different areas of AN. Because different areas of AN may have a different functional connection to HC (e.g., because of the arrangement of neural pathways in the AN and the other factors), stimulation delivery to first and second areas 141A, 141B may have different effects on the brain activity level within the HC.

Processor 60 determines the level of brain activity in the HC of brain 28 that results from the delivery of stimulation to the AN of brain 28 of patient 12 while the lead was in the second position (102), e.g., using the techniques discussed above with respect to FIGS. 6-9. Processor 60 than associates the level of brain activity in the HC with the second lead position, and stores the level of brain activity in the HC and the associated lead position in memory 62 of IMD 16 as brain activity information 76 or in a memory of another device (142).

The technique described with respect to mapping the areas of the AN of brain 28 corresponding to the first and second positions of lead 20A can be repeated for a plurality of lead 20A positions. In some cases, lead 20A can be moved to two positions, while in other cases, lead 20A can be moved to more than two positions (e.g., three positions, four positions, or more than four positions), and the area of the AN corresponding to each of the positions of lead 20A can be mapped. In some cases, a position of lead 20A may be moved until a particular change in the brain activity level resulting from the stimulation is identified. For example, if the brain activity level in the HC resulting from the delivery of stimulation to each of the areas of the AN decreases with each of the first few subsequent lead positions, but then the brain activity level begins to increase with the next lead position, processor 60 may determine that the area of AN that has the most meaning functional connection to the HC for the seizure disorder therapy has been passed, such that one of the previous areas of the AN may be better suited as a target therapy delivery site.

Figure 13:
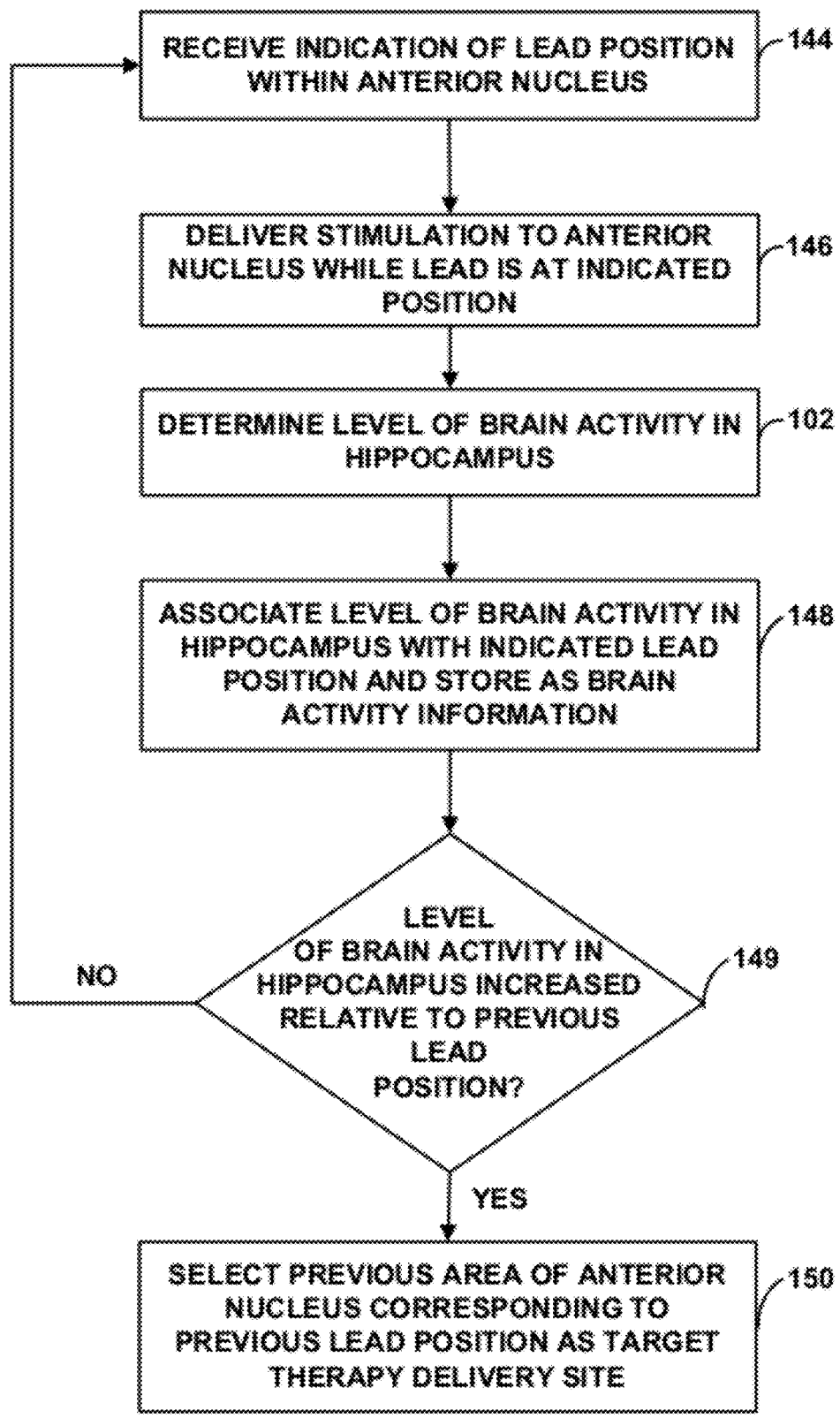
FIG. 13 is a flow diagram of an example technique for selecting a target therapy delivery site based on the mapping of the relative functional connections between a plurality of areas within an anterior nucleus of a thalamus of a brain and a hippocampus of the brain.

FIG. 13 is a flow diagram of an example technique for selecting a target therapy delivery site based on the aforementioned technique. The technique shown in FIG. 13 can be useful for identifying an area within the AN of brain 28 that has a relatively meaningful functional connection to the HC. In the example technique shown in FIG. 13, processor 60 of IMD 16 receives an indication of that lead 20A is at a particular position within the AN of brain 28 of patient 12 (144). In some examples, processor 60 receives the indication by way of a signal that is transmitted by programmer 14, as discussed above with respect to the indication of the second position of lead 20A in FIG. 12. While lead 20A is at the indicated position, processor 60 controls stimulation generator 64 of IMD 16 to generate and deliver a relatively high frequency stimulation (e.g., greater than or equal to about 80 Hz) to the AN of brain 28 of patient 12 via a subset of electrodes 24 (146). If a different position of lead 20A was previously mapped, the subset of electrodes 24 used to deliver stimulation to the AN while lead 20A was at the previous position can be used to deliver stimulation while lead is a the indicated position. As discussed above, delivering stimulation via the same electrodes for each lead position may help consistently change the area of the AN to which stimulation is delivered upon changing the position of lead 20A.

Processor 60 determines the level of brain activity in the HC of brain 28 that results from the delivery of stimulation to the AN of brain 28 of patient 12 while the lead was at the indicated position (102), e.g., using the techniques discussed above with respect to FIG. 6. Processor 60 associates the level of brain activity in the HC with the indicated lead position, and stores the level of brain activity in the HC and the associated lead position in memory 62 of IMD 16 as brain activity information 76 or in a memory of another device (148).

In order to select a target therapy delivery site within the AN that has a relatively meaningful functional connection to the HC (e.g., in the case of seizure disorder therapy, an area of the AN for which stimulation delivery resulted in suppression of activity in the HC), it can be desirable to compare the brain activity in the HC resulting from stimulation delivery to each of a plurality of different areas of the AN. As discussed above, with respect to a seizure disorder, it can be desirable to reduce the activity within the HC of brain 28 of patient 12 by delivering stimulation to the AN of brain 28. Accordingly, in the case of a seizure disorder, processor 60 determines which area of the AN is associated with the lowest relative level of brain activity in the HC.

In accordance with the technique shown in FIG. 13, processor 60 determines whether the level of brain activity in the HC that resulted from the delivery of stimulation to the AN of brain 28 of patient 12 while the lead was in the indicated position has increased relative to the previous lead position that was mapped (149). In response to determining no additional lead positions have been mapped (e.g., brain activity information 76 does not include any other HC activity levels and associated lead positions) or the level of brain activity in the HC has not increased relative to the previous lead position, processor 60 waits and does not control stimulation generator 64 to deliver any further stimulation until an indication of another position of lead 20A within the AN (144). If the level of brain activity in the HC has not increased relative to the previous lead position, processor 60 may determine that the area of the AN that is associated with the lowest relative level of brain activity in the HC has not yet been identified.

In some examples, processor 60 transmits an indication to programmer 14 that the area of the AN of brain 28 that is associated with the lowest relatively level of activity within the HC has not yet been reached or at least has not known to have been reached yet. Programmer 14 can then provide an indication to a user, such as a clinician, that lead 20A should be moved to another position. Upon receiving an indication that lead 10A has been moved to another position of lead 20A within the AN (144), processor 60 repeats the process described above with respect to the previous position of lead 20A in order to determine the level of brain activity associated with the next position of lead 20A (146, 102, 148, 149).

On the other hand, in response to determining the level of brain activity in the HC that resulted from the delivery of stimulation to the AN of brain 28 of patient 12 while the lead was in the indicated position has increased relative to the previous lead position that was mapped (149), processor 60 selects the area of the AN corresponding to the previously mapped lead position as the target therapy delivery site (150). The previously mapped lead position corresponds to an area of the AN of brain 28 that resulted in the relatively greatest amount of suppression of brain activity in the HC.

In some examples, lead 20A may be moved back to the previous position that lead 20A was in when the previous area of the AN was mapped. In other examples, lead 20A may remain in the same position and processor 60 can control stimulation generator 64 to deliver therapeutic stimulation to the selected target therapy delivery site, even while lead 20A is at the indicated position (and not at the previously mapped lead position) by, for example, delivering stimulation via a subset of electrodes 24 that correspond to the area of the AN associated with the previously mapped lead position. If lead 20A is moved between different positions by distance D (FIG. 11A), a subset of electrodes 24 may be positioned at the previously mapped lead position. As a result, the area of the AN to which stimulation was delivered when the desirable level of brain activity in the HC was observed can be targeted again without requiring lead 20A to be moved back to a previous position. While lead 20A can also be physically moved to the previously mapped position, it may be less invasive and stressful to tissue of brain 28 to instead select a different subset of electrodes 24 to target the area of AN corresponding to the previously mapped position and regain the effect of stimulation delivered to that area of the AN.

Figure 14:
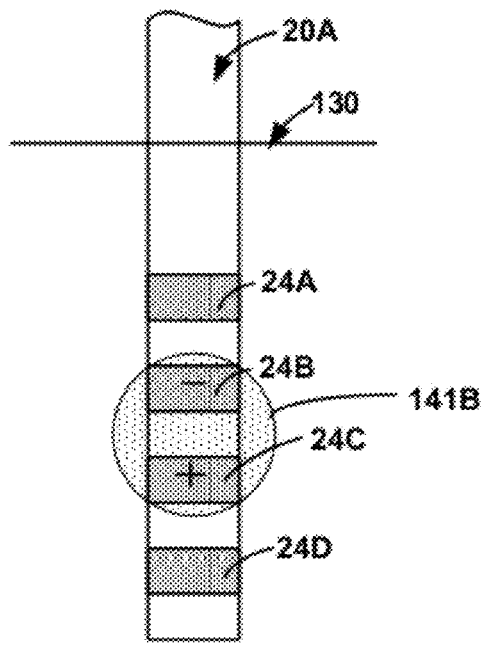
FIG. 14 is a schematic illustration of a lead within an anterior nucleus of a thalamus of a brain.

As an example of this technique, if processor 60 determines that delivery of stimulation to a first area of the AN of brain 28 associated with the first lead position shown in FIG. 11A resulted in a lower level of brain activity in the HC than the delivery of stimulation to a second area of the AN of brain 28 associated with the second lead position shown in FIG. 11B, processor 60 can deliver stimulation to the first area of the AN while lead 20A remains in the second position (FIG. 11B). As shown in FIG. 14, delivering stimulation via subset of electrodes 24B, 24C while lead 20A is in the second position can result in delivery of stimulation to area 141A of AN of brain 28, which is the area 141A of the AN of brain 28 corresponding to the first position of lead 20A shown in FIG. 11A. When lead 20A is in the second position, electrode 24B has substantially the same depth (relative to reference line 130) as electrode 24C when lead 20A is in the first position, and electrode 24C has substantially the same depth (relative to reference line 130) as electrode 24D when lead 20A is in the first position.

In other examples, in addition to or instead of changing a position of one or both leads 20A, 20B within AN in order to change an area of the AN to which stimulation is delivered, in order to map a plurality of areas within the AN with the HC, the stimulation can be delivered to each area of a plurality of areas of the AN by modifying the electrodes with which the stimulation is delivered to the AN. For example, while lead 20A is in the first position shown in FIG. 11A, stimulation generator 64 can deliver stimulation via electrodes 24C, 24D to deliver stimulation to a first area 141A in the AN and stimulation generator 64 can deliver via a second subset of electrodes 24B, 24C to deliver stimulation to a second, different area of the AN. In this way, an "area" within the AN can be defined by a subset of electrodes. The different subsets of electrodes selected to target different areas of the AN of brain 28 may not have any overlapping electrodes or, in some examples, may have at least one common electrode.

Figure 15:
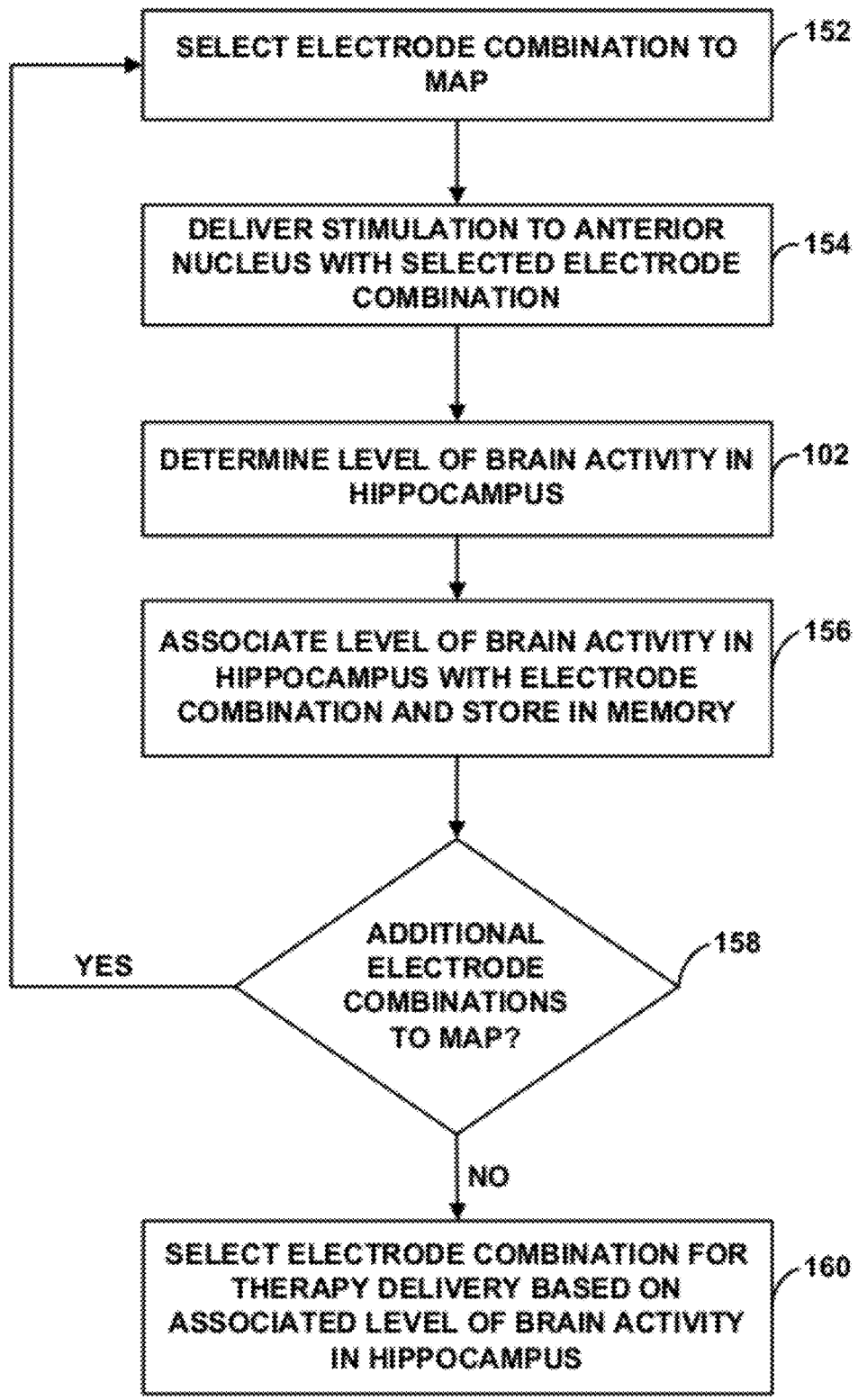
FIG. 15 is a flow diagram of an example technique for selecting an electrode combination with which electrical stimulation is delivered to a brain of a patient or sensed within the brain of the patient based on the mapping of the relative functional connections between a plurality of areas within an anterior nucleus of a thalamus of a brain and a hippocampus of the brain.
Figure 16:
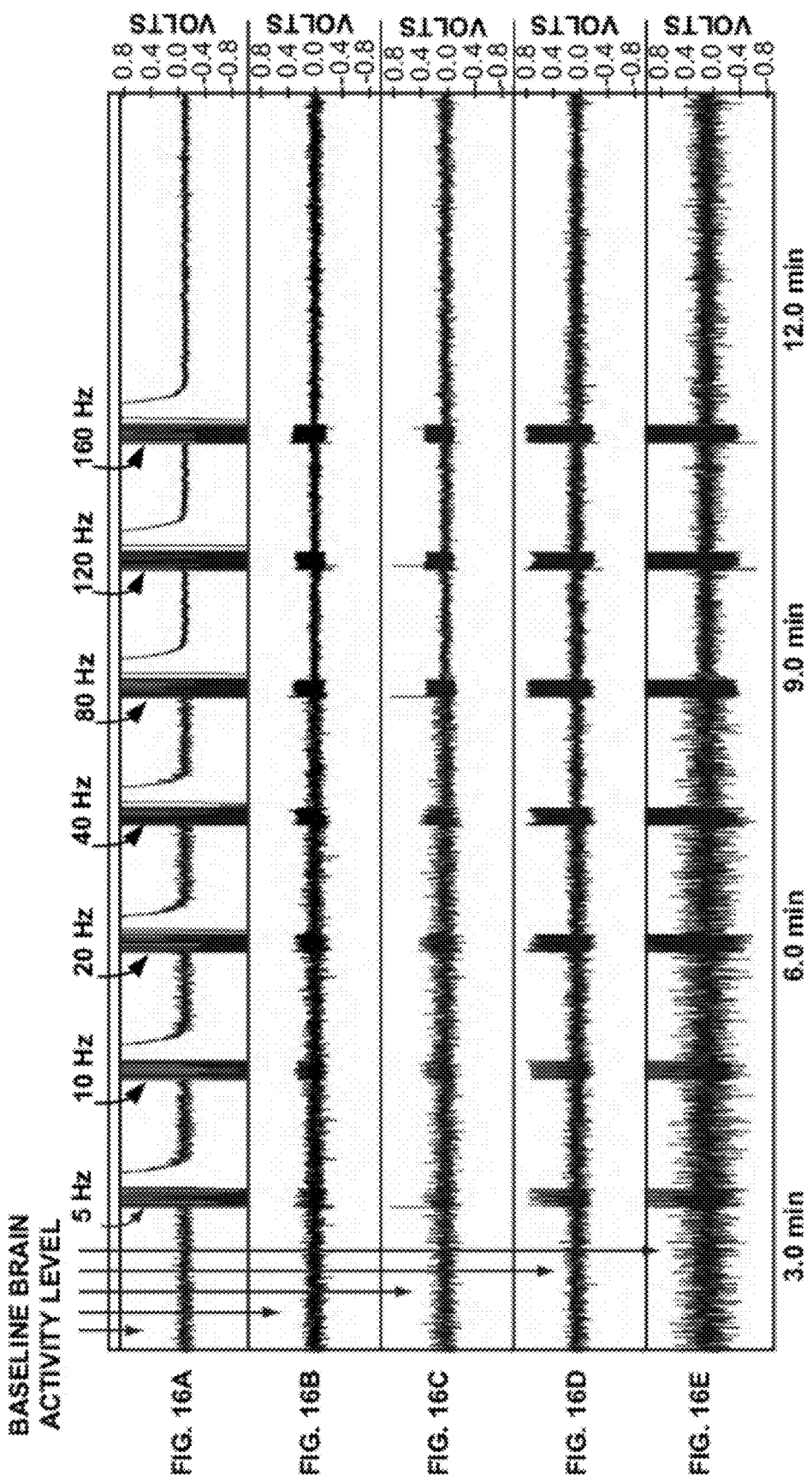
FIGS. 16A-16E, FIGS. 17A-17E, and FIGS. 18A-18E are plots of bioelectrical brain signals sensed within an anterior nucleus of a thalamus and a hippocampus of a brain of an ovine subject, and illustrate the example effects of stimulation delivered to the anterior nucleus at various pulse frequencies.
Figure 17:
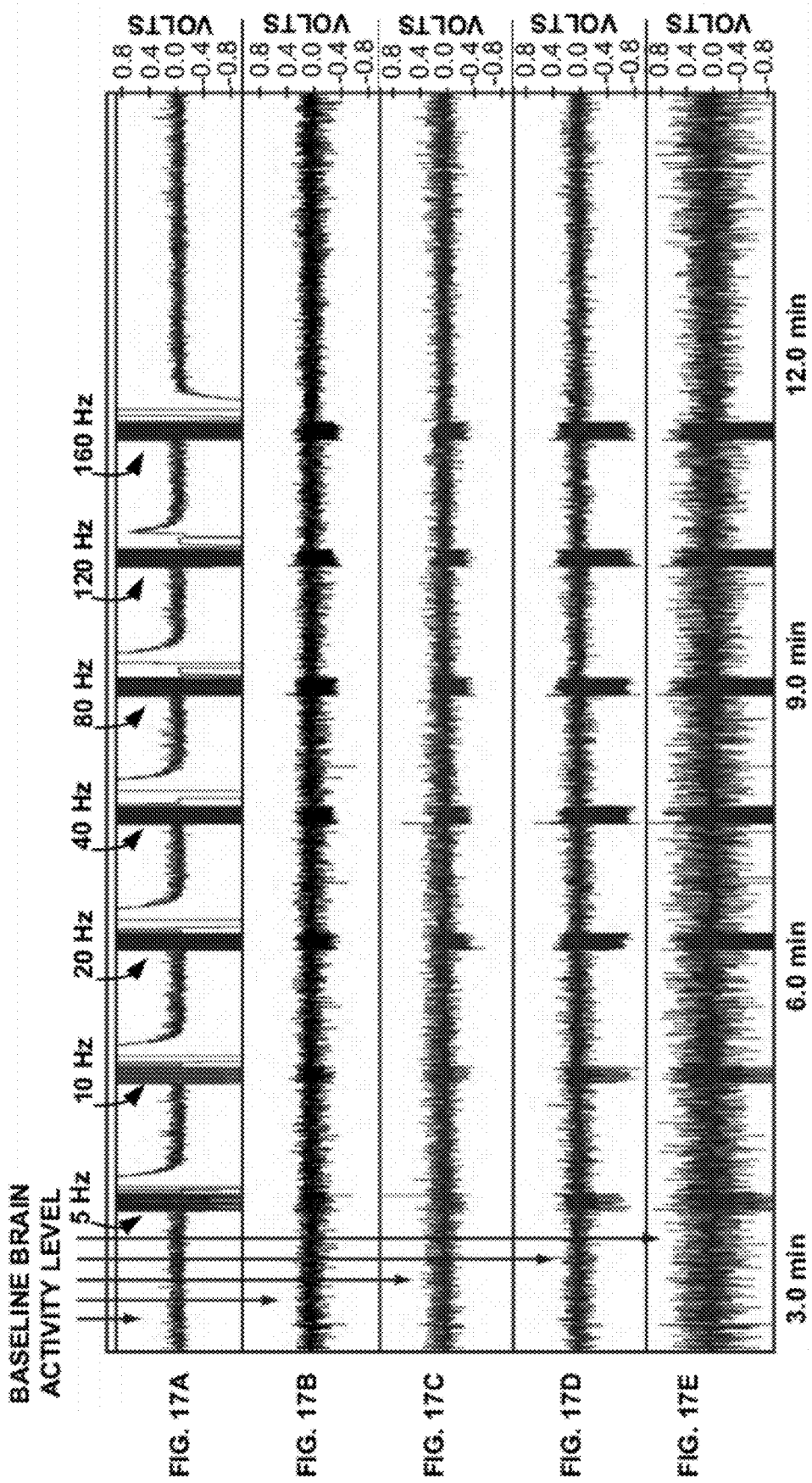
Figure 18:
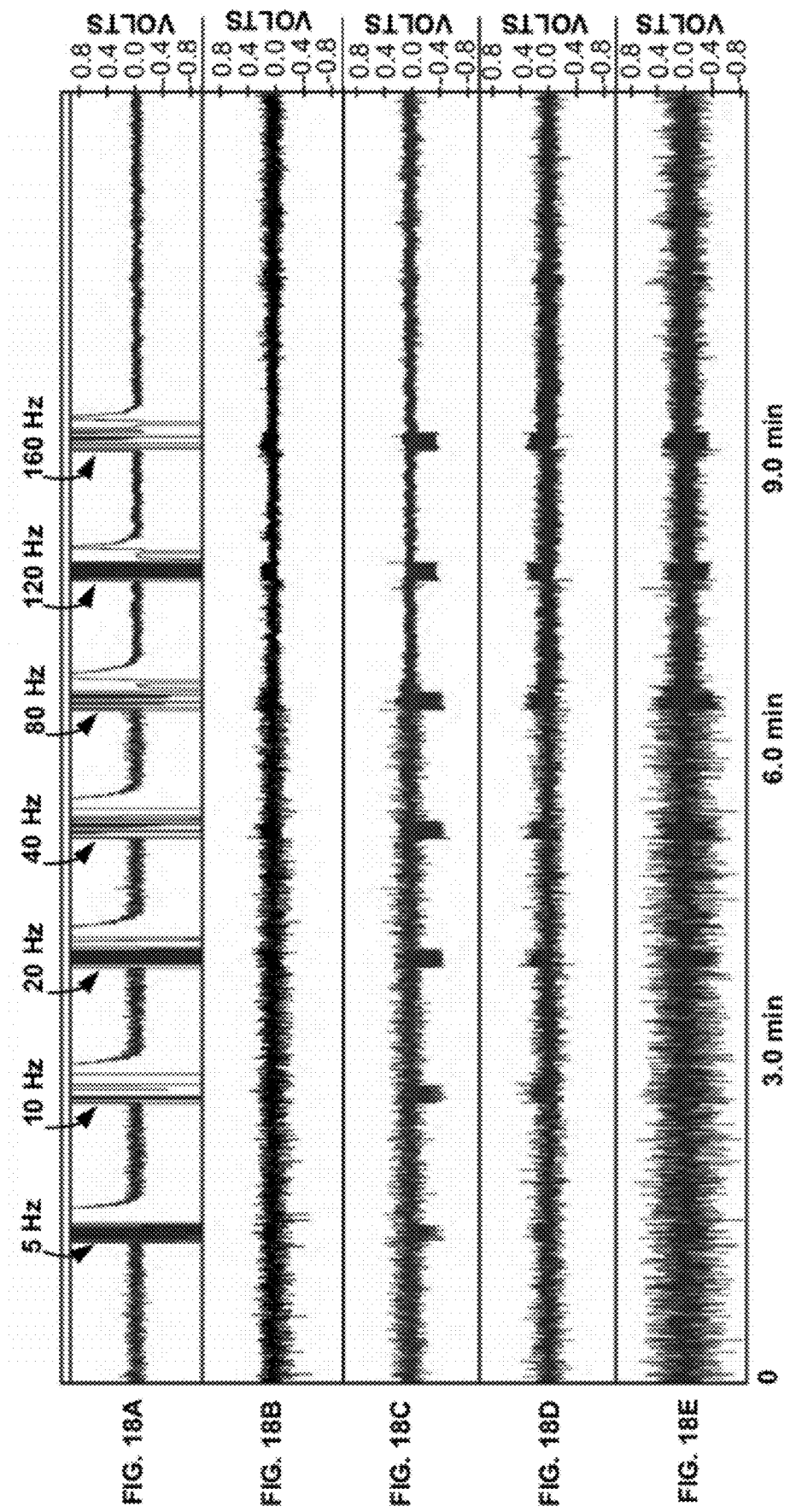

FIG. 15 is a flow diagram of an example technique for mapping a plurality of areas within the AN with the HC, where the areas correspond to different stimulation electrode combinations, and selecting a stimulation electrode combination based on the mapping. The technique shown in FIG. 16 may, in some examples, may also be used to select a sense electrode combination.

In accordance with the technique shown in FIG. 15, while lead 20A is at a first position in brain 28, processor 60 selects an electrode combination, which may be, for example, a subset of electrodes 24 and the respective polarity of the electrodes (152). The electrode combination can be, for example, a bipolar electrode combination, or multipolar (i.e., more than two electrodes). Processor 60 may then control stimulation generator 64 to generate and deliver electrical stimulation to AN of brain 28 via the selected electrode combination (154) and determine the level of brain activity in the HC of brain 28 resulting from the electrical stimulation (102).

Processor 60 may then associate the determined level of brain activity in the HC with the selected electrode combination and store the information in memory 62 (e.g., as brain activity information 76) (156).

After mapping one area of AN (corresponding to the selected electrode combination), processor 60 may determine whether there are additional electrode combinations to map (158). In some examples, processor 60 maps each of the plurality of electrode combinations available from electrodes 24 of lead 20A, while in other examples, processor 60 maps only a subset of the available electrode combinations. Processor 60 may store a list of available electrode combinations in memory 62 and determine whether there are additional electrode combinations to map (158) based on the list. The list may be, for example, provided by a clinician. In other examples, processor 60 may receive electrode combinations to map from programmer 14 and may, therefore, determine whether there are additional electrode combinations to map (158) based on input from programmer 14. Programmer 14 may transmit the electrode combination to map to IMD 16 via the respective telemetry modules.

In response to determining there are additional electrode combinations to map (YES branch of block 158), processor 60 selects the additional electrode combination (152), controls stimulation generator 64 to generate and deliver electrical stimulation to brain 28 using the additional electrode combination (154), determines the evoked level of brain activity in the HC (102), and associates the determined level of brain activity with the additional electrode combination (156). Processor 60 may repeat this process for each additional electrode combination to map.

On the other hand, in response to determining there are no additional electrode combinations to map (NO branch of block 158), processor 60 may stop the electrode combination mapping process for the particular lead position. In some examples, processor 60 may repeat the technique shown in FIG. 15 for each of a plurality of lead positions (e.g., lead positions being described with respect to FIGS. 12 and 13), such that the mapped information distinguishes areas of the AN based on the lead position and the subset of electrodes of lead 20A. Regardless of whether processor 60 maps the electrode combinations for one lead position or a plurality of lead positions, processor 60 may select an electrode combination for therapy delivery to brain 28 based on the level of brain activity in HC associated with the electrode combination (and, in some cases, electrode combination and lead position) (160). For example, in the case of seizure disorder therapy, processor 60 may select the electrode combination that is associated with the lowest level of activity in the HC. As another example, in the case of therapy delivered to manage Alzheimer's, processor 60 select the electrode combination associated with the highest level of activity in the HC.

FIGS. 16A-16E are plots that illustrate the example effects of stimulation delivered to the AN of a brain of an ovine subject at various pulse frequencies. To generate the test results shown in FIGS. 16A-16E, stimulation pulses were delivered to the AN of the ovine subject in ten second bursts at frequencies of about 5 Hz, about 10 Hz, about 20 Hz, about 40 Hz, about 80 Hz, about 120 Hz, and about 160 Hz, progressing in that order as the plots in FIGS. 16A-16E move from left to right when viewing FIGS. 16A-16E. For each stimulation frequency, a single, approximately 10 second burst was delivered, followed by an approximately 60 second "off" period, during which no stimulation was delivered to the brain of the ovine subject. The pulse width of the stimulation was approximately 120 microseconds and the pulse amplitude was approximately 10 volts.

In conjunction with the therapy delivery, activity in the both the AN and HC of the brain of the ovine subject was monitored to determine the changes resulting from the delivery of the stimulation pulses to the AN. To evaluate the changes to brain activity, brain signals were monitored in both the AN and HC prior to delivery of the electrical stimulation to determine a baseline level of brain activity (labeled "Baseline" in FIGS. 16A-16E) for each region. FIG. 16A is a plot illustrating changes in the AN of the ovine subject resulting from the delivery of electrical stimulation to the AN for the described stimulation conditions relative to the baseline brain activity level in the AN, and FIGS. 16B-16E are plots illustrating changes in brain activity in the HC of the ovine subject resulting from the delivery of electrical stimulation to the AN for the described stimulation conditions relative to the baseline brain activity level in the HC. The plots illustrated in FIGS. 16A-16E are aligned, such that the corresponding portions of each plot illustrate the activity within the respective region of the brain of the ovine subject at substantially the same time.

The plot shown in FIG. 16A illustrates a bioelectrical brain signal sensed in the AN of the ovine subject, and the plots shown in FIGS. 16B-16E illustrate a bioelectrical brain signal sensed in the HC of the subject via four different bi-polar electrode configurations. The electrode configuration for sensing bioelectrical brain signals within the HC of the ovine subject can affect the proximity to the AN, which, therefore, can affect the activity sensed within the HC resulting from delivery of stimulation to the AN. Accordingly, the different electrode combinations may sense different bioelectrical brain signals. However, each of the plots illustrating brain activity in the HC illustrates similar behavior in response to the stimulation delivered to the AN.

As illustrated by the plots of FIGS. 16A-16E, the suppression of brain activity in the AN and the HC of the brain of the ovine subject increased as the frequency of the stimulation delivered to the AN increased. The plots indicate that, at a stimulation frequency of about 80 Hz, the activity level in the HC decreased significantly, as reflected in the amplitude of the sensed bioelectrical brain signal shown in FIGS. 16B-16E after the 80 Hz stimulation. Accordingly, the plots in FIGS. 16A-16E indicate that the suppression of brain activity in the HC may be greater when a relatively high frequency stimulation (e.g., greater than or equal to about 80 Hz) is delivered to an AN of a subject compared to when a relatively low frequency stimulation (e.g., lower than about 80 Hz, such as about 5 Hz to about 40 Hz). It is believed that for some patient conditions, a duration of the suppression in the HC is not as significant as much as the magnitude of the suppression when identifying a target therapy delivery site in the AN that is functionally related to the HC in a manner that is relevant to deep brain stimulation for managing a seizure disorder.

Based on at least the test results shown in FIGS. 16A-16E, it is believed that mapping the functional connection between different areas of the AN to the HC by delivering a relatively high frequency stimulation (e.g., greater than or equal to about 80 Hz) to the AN can be useful for identifying a target therapy delivery site in the AN that is useful for seizure disorder therapy.

The plots of FIGS. 16A-16E also illustrate a correlation between changes to the brain activity sensed at the AN and changes to the brain activity sensed at the HC. This correlation between HC and AN with regard to the changes in brain activity resulting from delivery of electrical stimulation to the AN indicates that bioelectrical brain signals sensed in the AN may be used as a surrogate of brain activity in the HC, such that the bioelectrical brain signals sensed in the AN may be used to determine changes in the bioelectrical brain signals in the HC resulting from delivery of electrical stimulation to the AN. Therefore, it is believed that, in some cases, leads 20 (FIG. 1) may be implanted in brain 28 of patient 12 such that stimulation generator 64 delivers electrical stimulation via a selected subset of electrodes 24, 26 to the AN and sensing module 66 monitors brain signals via a selected subset of electrodes 24, 26 in the AN to detect changes to the bioelectrical signals, e.g., suppression of brain activity, in the HC resulting from the stimulation delivered to the AN.

In other examples, system 10 may be configured to deliver electrical stimulation directly to the AN via a first set of electrodes and directly sense brain signals via a second set of electrodes located in the HC, where the first and second sets of electrodes are carried by a separate or common leads and have at least one different electrode. However, such a configuration may be more invasive than a configuration in which a single set of electrodes in the AN are used to deliver therapy to the AN and monitor brain signals to detect changes to the brain signal evoked by the therapy delivery.

The correlation between changes to the brain activity sensed at the AN and changes to the brain activity sensed at the HC is further evidenced by the test results shown in FIGS. 17A-17E. As with FIGS. 16A-16E, FIGS. 17A-17E are plots that illustrate the example effects of stimulation delivered to the AN of a brain of an ovine subject at various pulse frequencies. To generate the test results shown in FIGS. 17A-17E, stimulation pulses were delivered to the AN of the ovine subject with the same stimulation parameter values as that used to generate the plots illustrated in FIGS. 16A-16E. In particular, stimulation was delivered to an AN of the brain of the same ovine subject in ten second bursts at frequencies of about 5 Hz, about 10 Hz, about 20 Hz, about 40 Hz, about 80 Hz, about 120 Hz, and about 160 Hz, progressing in that order as the plots in FIGS. 17A-17E move from left to right when viewing FIGS. 17A-17E. For each stimulation frequency, a single, approximately 10 second burst was delivered, followed by an approximately 60 second "off" period, during which no stimulation was delivered to the brain of the ovine subject. The pulse width of the stimulation was approximately 120 microseconds and the pulse amplitude was approximately 10 volts.

FIGS. 17A-17E differ from FIGS. 16A-16E in that different electrode combinations were used to deliver the stimulation to the AN of the brain of the ovine subject. Referring to lead 20A illustrated in FIG. 11A as an example of the lead that was implanted in the ovine subject to deliver stimulation to the AN of the ovine subject, electrode 24C was assigned as a cathode and electrode 24D was assigned as an anode in the electrode combination that was used to deliver stimulation to the AN of the ovine subject when the test results shown in FIGS. 16A-16E were generated.

To generate the results shown in FIGS. 17A-17E, lead 20A was moved in a deep direction into the brain of the ovine subject by a distance D, which is substantially equal to the length of an electrode (measured in a direction along a longitudinal axis of the lead) plus the distance between adjacent electrodes. At the second position of lead 20A (shown in FIG. 11B), stimulation was delivered to the AN of the brain of the ovine subject with an electrode combination in which electrode 24B was assigned as an anode and 24C was assigned as a cathode.

As discussed above with respect to FIGS. 11A and 11B, in the second position of lead 20A shown in FIG. 11B, electrode 24C substantially aligns with electrode 24D when lead 20A was in the first position shown in FIG. 11A, and electrode 24B substantially aligns with electrode 24C when lead 20A was in the first position. Thus, when stimulation was delivered to the AN of the ovine subject during the tests performed to generate the results shown in FIGS. 16A-16E (referred to as the first test) and FIGS. 17A-17E (referred to as the second test), electrodes at substantially the same position within the AN of the subject were used. However, the polarity of the electrodes was switched between the first and second tests.

As shown in FIG. 17A, when stimulation was delivered to the AN of the ovine subject at the second lead position and the reversed electrode polarity (as compared to the first test), the stimulation had a minimal suppressive effect on the brain activity of in the HC of the ovine subject, but the activity in the AN was not reduced. This indicates that the stimulation delivered to the AN in both the first and second tests did not have a direct effect (e.g., a local effect and/or a relatively low functional connection to the HC) on the activity in the AN, but, rather, that the suppression to the activity in the AN that was observed in the first test (as shown in FIG. 16A) may have resulted from suppression of activity in the HC (as shown in FIGS. 16B-16E). Thus, based on the results of the first and second tests, as well as the understanding of the Circuit of Papez, it is believed that suppression of brain activity in the HC of a brain can be reflected back to the AN. As a result, brain activity in the AN (e.g., as indicated by a bioelectrical brain signal sensed in the AN) can be a surrogate for brain activity in the HC of the brain.

To confirm that the delivery of stimulation to the AN at a relatively high frequency (e.g., greater than about 80 Hz) can result in suppression of activity in the HC, a third test was conducted on the same ovine subject. FIGS. 18A-18E are plots that illustrate the effects of stimulation delivered to the AN of a brain of an ovine subject at various pulse frequencies, where the stimulation was delivered using a different set of electrodes. In particular, while the lead was at the second position (e.g., as shown in FIG. 11B), which was also the lead position used when the results shown in FIGS. 17A-17E were generated, electrode 24A (FIG. 11B) was selected as an anode and electrode 24B was selected as a cathode, such that stimulation was delivered to a different area of the AN compared to the areas to which stimulation was delivered in the first and second tests (FIGS. 16A-16E and FIGS. 17A-17E, respectively). Stimulation pulses were delivered to the AN of the ovine subject with the same stimulation parameter values as that used to generate the plots illustrated in FIGS. 16A-16E and FIGS. 17A-17E.

As illustrated by the plots of FIGS. 18A-18E, the brain activity in the AN and the HC of the brain of the ovine subject began to decrease at a stimulation frequency of about 80 Hz. These plots, in combination with the plots shown in FIGS. 17A-17E in which no suppressive effect was observed in the AN, though there was minimal suppressive stimulation effect on in the HC, confirms that stimulation delivery to the AN at a relatively high frequency (e.g., greater than or equal to about 80 Hz) can have a suppressive effect on brain activity in the HC, which may then be reflected back to the AN and observed as a lower brain activity level in the AN following the delivery of the relatively high frequency stimulation to the AN.

Figure 19:
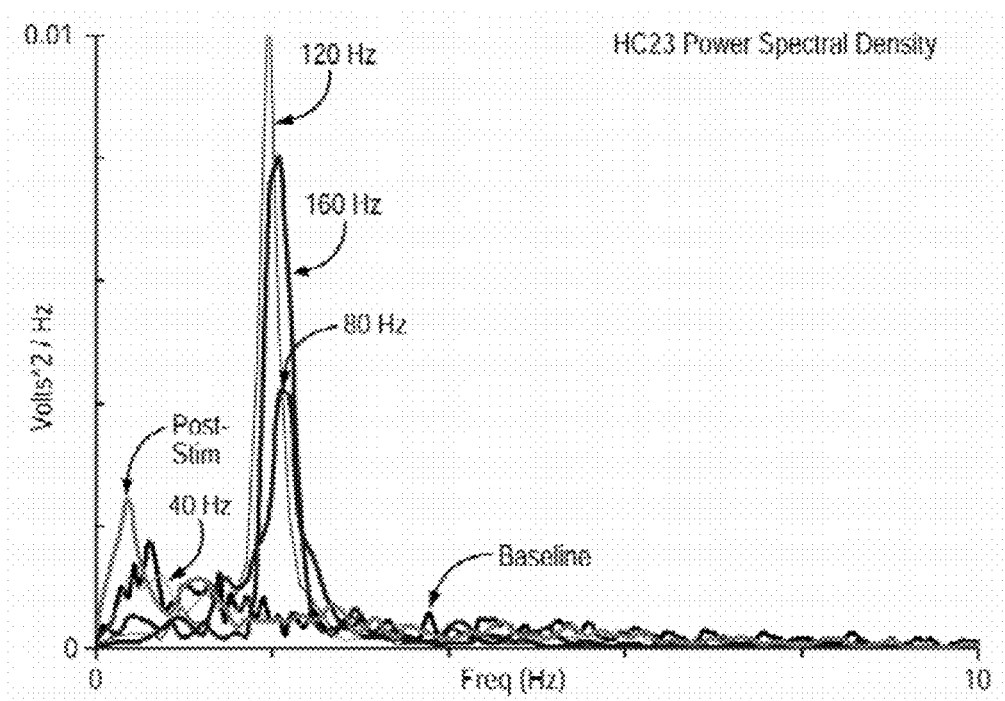
FIG. 19 is a plot illustrating the power spectral density of a bioelectrical brain signal sensed in a hippocampus of a brain of an ovine subject following the delivery of different stimulation frequencies to an anterior nucleus of a thalamus the brain of the ovine subject.

FIG. 19 is a plot illustrating the power spectral density of a bioelectrical brain signal sensed in the HC of a brain of an ovine subject following the delivery of different stimulation frequencies to the AN. The power density shown is proportional to power given a particular resistance. Stimulation pulses were delivered to the AN of an ovine subject in ten second bursts at frequencies of about 5 Hz, about 10 Hz, about 20 Hz, about 40 Hz, about 80 Hz, about 120 Hz, and about 160 Hz, and the fast Fourier Transform (FFT) of each of the bioelectrical brain signals sensed in the HC were plotted, as shown in FIG. 19. Also shown in FIG. 19 is the power spectral density of a bioelectrical brain signal in a post-stimulation period, approximately six minutes after the final stimulation burst (at a frequency of about 160 Hz) was delivered to the AN of the subject.

The plots shown in FIG. 19 indicate that the power level in the lower frequency bands (e.g., less than about 5 Hz) of a bioelectrical brain signal sensed in the HC began to increase as the stimulation frequency increased. A bioelectrical brain signal power level distribution in which the power levels are relatively high in lower frequency bands as compared to higher frequency bands indicates that the brain activity level reflected by the bioelectrical brain signal is relatively low. Thus, the plots shown in FIG. 19 indicate that the brain activity in the HC began to decrease (i.e., the stimulation suppressed the brain activity level) as the stimulation frequency increased. As shown in FIG. 19, a first substantial jump in the power level in the approximately 2 Hz frequency band was observed at a stimulation frequency of about 80 Hz, and the power level increased at the stimulation frequencies of about 120 Hz and about 160 Hz.

The results shown in FIG. 19 further indicate that the suppression of brain activity in the HC may increase when a relatively high frequency stimulation (e.g., greater than or equal to about 80 Hz) is delivered to an AN of a subject compared to when a relatively low frequency stimulation (e.g., lower than about 80 Hz, such as about 5 Hz to about 40 Hz). This further indicates that in the case of a seizure disorder therapy in which stimulation is delivered to the AN of a brain of a patient to reduce activity in the HC of the brain, mapping the functional connection between different areas of the AN to the HC by delivering a relatively high frequency stimulation (e.g., greater than or equal to about 80 Hz) to the AN can be useful for identifying a target therapy delivery site in the AN that may provide efficacious seizure disorder therapy.

Figure 20:
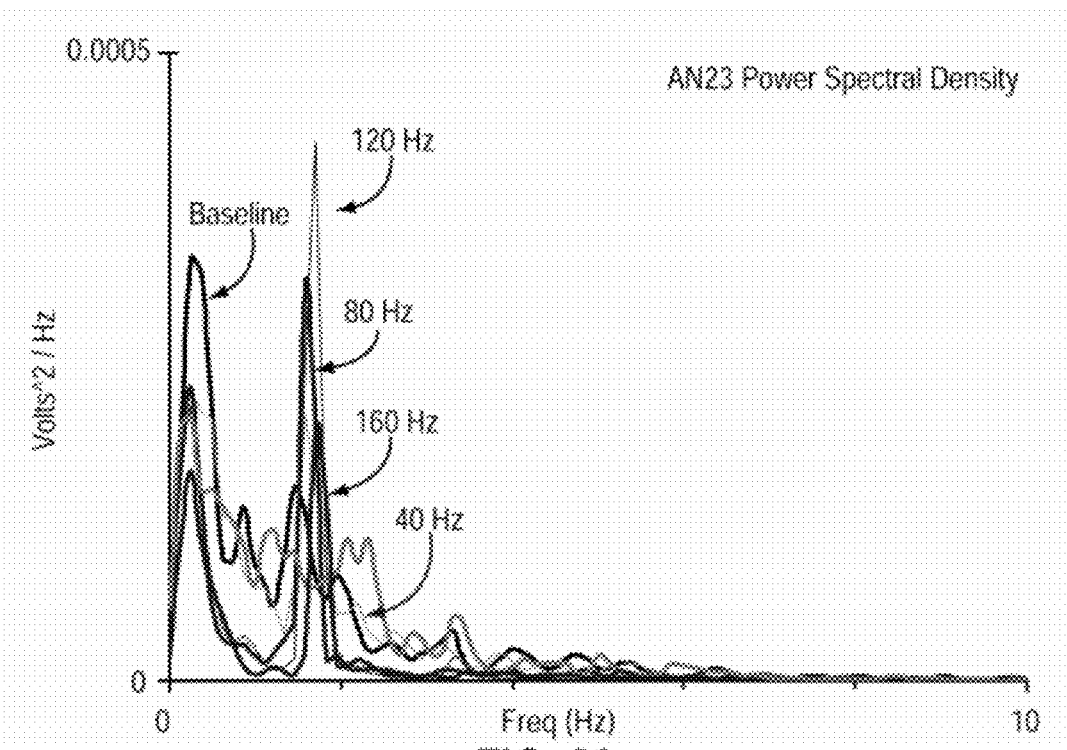
FIG. 20 is a plot illustrating the power spectral density of a bioelectrical brain signal sensed in the anterior nucleus of the thalamus the brain of the same ovine subject from which the plots shown in FIG. 19 were generated following the delivery of different stimulation frequencies to the anterior nucleus.

FIG. 20 is a plot illustrating the power spectral density of a bioelectrical brain signals sensed in the AN of a brain of the same ovine subject used to generate the plots shown in FIG. 19 following the delivery of different stimulation frequencies to the AN. The plots shown in FIG. 20 were generated based on bioelectrical brain signals sensed in the AN at substantially the same time the bioelectrical brain signals from which the plots shown in FIG. 19 were generated was sensed. As the plots in FIG. 19 indicated, the delivery of stimulation signal having a frequency of about 80 Hz or more to the AN of the subject resulted in suppression of brain activity in the HC. As previously indicated, the suppression of brain activity in the HC in response to stimulation delivery to a particular area of the AN can indicate a physiologically significant functional connection between the area of the AN and the HC for purposes of seizure disorder therapy delivery.

The plots shown in FIGS. 19 and 20 indicate that, following the delivery of the relatively high frequency stimulation (e.g., about 80 Hz or greater) to the AN of the subject, the bioelectrical brain signals sensed in the AN and HC of the subject reflected a relatively high activity level in at the 2 Hz frequency. This suggests that the relatively high frequency stimulation delivered to the AN may have effected a change in the oscillation activity of the activity in the HC that is indicated by the relatively high activity level in at the 2 Hz frequency level. Based on these test results, it is believed that at least one metric that can be used to indicate a meaningful functional connection between the HC and the AN for seizure disorder therapy is the power level in a frequency band including and around 2 Hz. As previously indicated, FIGS. 21A-22B illustrate results of a fourth test that further indicate that delivery of stimulation signal having a frequency of about 80 Hz or higher to the AN of an ovine subject can result in suppression of brain activity in the HC. FIGS. 21A and 21B are plots illustrating example effects on brain activity in the HC by delivery of stimulation to the AN of an ovine subject at various example stimulation pulse rates. As indicated in FIG. 21A, stimulation was sequentially delivered at pulse rates of about 5 Hz, about 10 Hz, about 20 Hz, about 40 Hz, about 80 Hz, about 120 Hz, and about 160 Hz, separated by periods during which no stimulation delivered to the AN. The stimulation pulses had pulse widths of approximately 120 microseconds and pulse amplitudes of approximately 10 volts. For each frequency, the stimulation was delivered in a single, 10 second burst.

As shown in FIG. 21A, the effect of the electrical stimulation delivered to the AN on the brain activity in the HC of the ovine subject varied according to the pulse rate of the delivered electrical stimulation. Changes to the brain activity are illustrated by a comparison of the brain activity sensed in the HC during a baseline state (as labeled in FIG. 21A) where the activity in the HC was not influenced by electrical stimulation, and the brain activity sensed in the HC following delivery of electrical stimulation to the AN at each stimulation pulse rate. As shown in FIG. 21A, the delivery of relatively high frequency stimulation (e.g., stimulation signals having a frequency of about 80 Hz, about 120 Hz, and about 160 Hz) to the AN significantly suppressed brain activity in the HC in the period directly following delivery of the electrical stimulation compared to after the delivery of lower frequency stimulation (e.g., 5 Hz, 10 Hz, and 20 Hz).

In FIG. 21B, stimulation was sequentially delivered to the AN at pulse rates of about 160 Hz, about 120 Hz, about 80 Hz, about 40 Hz, about 20 Hz, about 10 Hz, and about 5 Hz separated by periods during which no stimulation delivered to the AN. The stimulation pulses had pulse widths of approximately 120 microseconds and pulse amplitudes of approximately 8.1 volts. For each frequency, the stimulation was delivered in a single, 10 second burst. As shown in FIG. 21B, even when the relatively high frequency stimulation was delivered to the AN first, the delivery of relatively high frequency stimulation (e.g., stimulation signals having a frequency of about 80 Hz, about 120 Hz, and about 160 Hz) to the AN significantly suppressed brain activity in the HC in the period directly following delivery of the electrical stimulation. The suppressive effect of the stimulation delivery to the AN decreased as the stimulation frequency decreased.

FIGS. 22A and 22B are bar graphs illustrating the amplitudes of the bioelectrical brain signals shown in FIGS. 21A and 21B, respectively. In FIGS. 22A and 22B, "BL" indicates the baseline level of brain activity in the HC prior to delivery of any stimulation to the AN, and the "R1," "R2," "R3," "R4," "R5," "R6," "R7," "R8," and "R9" indicate the level of brain activity after a certain time period after the final stimulation burst (at approximately 160 Hz) was delivered to the subject. For example, "R1" indicates the brain activity measurement take approximately one minute after the final stimulation burst, "R2" indicates the brain activity measurement take approximately two minutes after the final stimulation burst, and so forth for the "R3," "R4," "R5," "R6," "R7," "R8," and "R9" indicators. The brain activity in FIGS. 22A and 22B is indicated by root mean square amplitude value of a bioelectrical brain signal as a percentage of a baseline for the subject (e.g., when no stimulation effects were observed).

As FIGS. 22A and 22B illustrate, the amplitude of the bioelectrical brain signals decreased as the frequency of the stimulation delivered to the AN increased. Thus further indicates that the delivery of relatively high frequency stimulation (e.g., stimulation signals having a frequency of about 80 Hz, about 120 Hz, and about 160 Hz) to the AN may suppress brain activity level (resulting in a bioelectrical brain signal with a lower amplitude) in the HC in the period directly following delivery of the electrical stimulation.

In general, the results of the fourth test conducted on the ovine subject indicate that suppressive effect that the stimulation had on brain activity sensed in the HC compared to the baseline state increased as the frequency of the stimulation delivered to the AN increased.

In some examples, processor 80 of programmer 14 (FIG. 4) can generate and present a graphical user interface via user interface 86 of programmer 14, where the graphical user interface presents information that can be used to compare the functional connection between each area of a plurality of areas of the AN and the HC. The information that is displayed can include, for example, one or more metrics related to the brain activity in the HC resulting from stimulation delivery to the AN of brain 28. Example metrics include, but are not limited to, a characteristic of a bioelectrical brain signal sensed in the HC and/or AN of brain 28 of patient 12 following the delivery of stimulation to the AN. The characteristic may include, for example, an amplitude of the bioelectrical brain signal, the variance of the bioelectrical brain signal over time, or a frequency domain characteristic (e.g., an energy level within one or more specific frequency bands) of the bioelectrical brain signal. The amplitude value may comprise an average, peak, peak-to-peak, mean or instantaneous amplitude value over a period of time or a maximum amplitude or an amplitude in a particular percentile of the maximum. In addition, the amplitude value may be an absolute amplitude value or a root mean square amplitude value.

Figure 23:
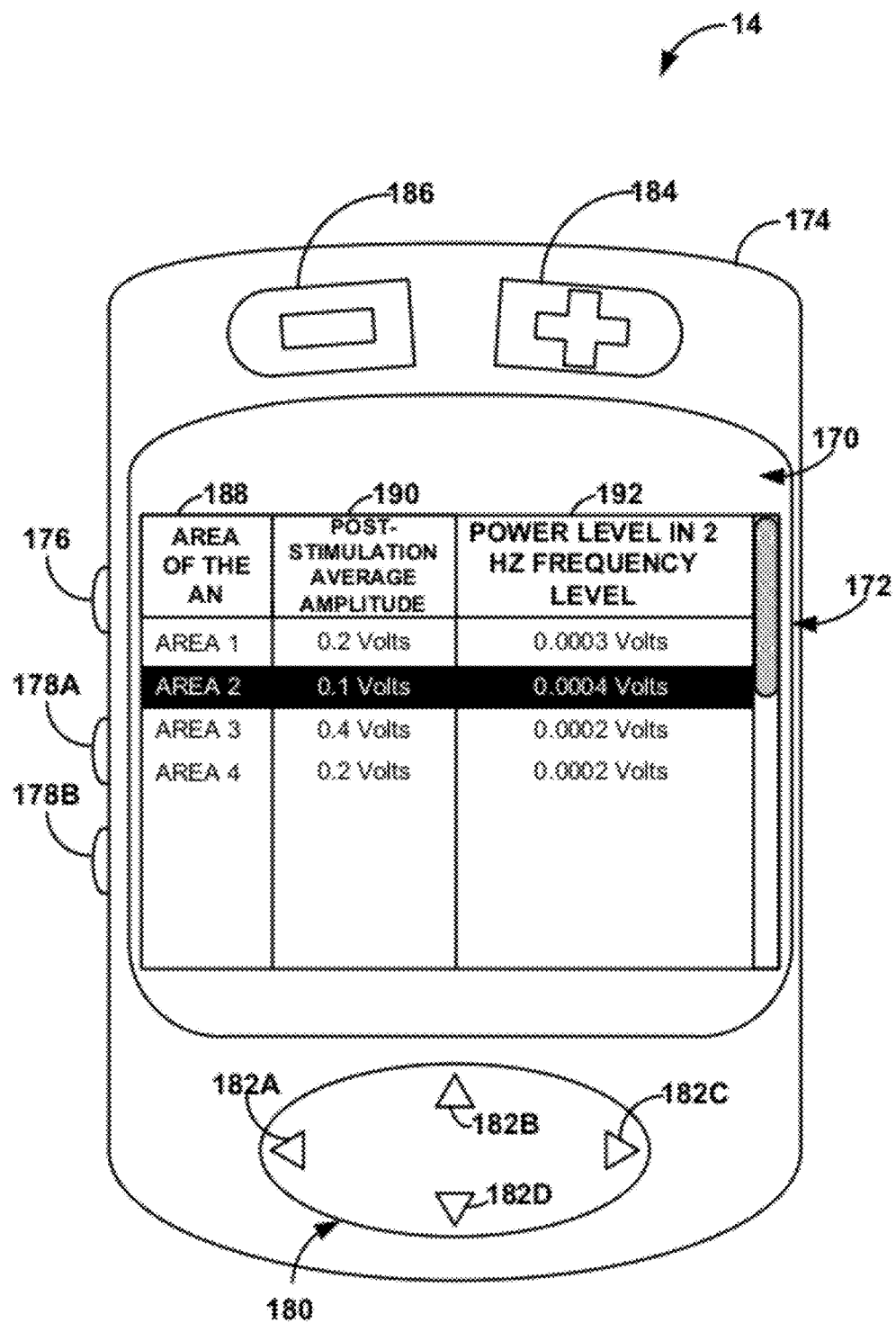
FIGS. 23-25 each illustrate an example graphical user interface (GUI) that presents indications of a plurality of areas of an anterior nucleus of a thalamus of a brain of a patient and one or more associated metrics, where each metric provides an indication of a relative functional connection between the area of the anterior nucleus and a hippocampus of the brain.

FIG. 23 is an example is a schematic illustration of programmer 14, which illustrates an example graphical user interface (GUI) 170 presented on display 172 of programmer 14, where GUI 170 lists a plurality of areas of the AN and associated metrics that indicate the relative degree of the functional connection between the area of the AN and the HC of brain 28 of patient 12. Programmer 14 includes housing 174, power button 176, contrast buttons 178A, 178B, control pad 180 with directional buttons 182A, 182B, 182C, and 182D, increase button 184, and decrease button 186. Housing 174 may substantially enclose the components of programmer 14, such as processor 80, memory 82, telemetry module 84, and power source 88 (FIG. 4). A user may depress power button 176 to turn programmer 14 on or off. Programmer 14 may include safety features to prevent programmer 14 from shutting down during a telemetry session with IMD 16 or another device in order to prevent the loss of transmitted data or the stalling of normal operation. In addition or instead, programmer 14 and IMD 16 may include instructions for handling possible unplanned telemetry interruption, such as battery failure or inadvertent device shutdown.

Display 172, which is a part of user interface 86 of programmer 14, may be any suitable display, such as an LED display, an LCD, a touch screen display, or another type of monochrome or color display capable of presenting information to a user, e.g., a clinician. Contrast buttons 158A, 158B may be used to control the contrast of display 172. In addition to displaying a list of mapped areas of the AN and corresponding metrics that indicate the functional connectivity of the area of the AN to the HC, processor 80 of programmer 14 may also present information regarding the type of IMD 16, operational status of IMD 16, patient data, and operational status of programmer 14 on display 172.

Control pad 180 allows the user to navigate through items presented on display 172. For example, the clinician may press control pad 180 on any of arrows 182A-182D in order to move between items presented on display 172 or move to another screen not currently shown by display 172. For example, the clinician may depress or otherwise activate arrows 182A, 182C to navigate between screens of GUI 170, and depress or otherwise activate arrows 182B, 182D to scroll through the areas of the AN and/or metrics presented by GUI 170. The clinician may press the center portion of control pad 180 in order to select any highlighted element in GUI 170. For example, the clinician may scroll to and "AREA 2," which is shown to be highlighted in FIG. 23, in order to receive more information about the selected area, such as a graphical representation of the raw bioelectrical brain signal indicative of activity in the HC after the delivery of stimulation to AREA 2. In other examples, scroll bars, a touch pad, scroll wheel, individual buttons, a stylus (in combination with a touch screen display 172) or a joystick may perform the complete or partial function of control pad 180.

Increase button 184 and decrease button 186 provide input mechanisms for a user, such as clinician or patient 12. If, for example, GUI 170 displays a therapy parameter value for adjustment by the user, depressing decrease button 186 one or more times may decrease the value of a highlighted therapy parameter and depressing increase button 184 one or more times may increase the value of a highlighted therapy parameter. In addition, patient 12, the clinician or another user may utilize control pad 180, buttons 184, 186 or display 172 in examples in which display 172 comprises a touch screen to input information.

Programmer 14 may take other shapes or sizes not described herein. For example, programmer 14 may take the form of a clam-shell shape, similar to cellular phone designs. In any shape, programmer 14 may be capable of performing the requirements described herein. Furthermore, in other examples, the buttons of programmer 14 may perform different functions than the functions provided in FIG. 23. In addition, other examples of programmer 14 may include different button layouts or number of buttons. For example, display 172 may be a touch screen that incorporates all user interface and user input mechanism functionality.

In the example shown in FIG. 23, GUI 170 includes a list of areas of the AN 188 to which a relatively high frequency stimulation (e.g., greater than or equal to about 80 Hz) was delivered to map the areas of the AN to the HC of brain 28 of patient 12, e.g., using any one or more of the techniques described with respect to FIGS. 6-9. The areas are listed as "AREA 1," "AREA 2," "AREA 3," and "AREA 4." Programmer 14 can indicate the areas of the AN of brain 28 using other indicators, such as other alphanumeric text or graphical indications of the areas. In some examples, the listed areas correspond to areas of the AN to which stimulation is delivered via a the same subset of electrodes, but different lead positions. In other examples, each listed area of the AN of brain 28 corresponds to the area of the AN to which stimulation is delivered when leads 20 are in the same position, but different electrode combinations (i.e., different subsets of electrodes 24, 26) are used to deliver stimulation to the AN. Although four areas of the AN are shown in FIG. 23, in other examples, GUI can list any suitable number of areas of AN, which may depend upon the number of electrodes on the one or more leads implanted in AN of brain 28 of patient 12.

GUI 170 also provides, for each area of the AN, two metrics for comparing different areas of the AN. Each area of the AN may have a different level of functional connectivity to the HC (e.g., because of the neural pathways between the AN and HC), and, as a result, the delivery of stimulation to the different areas of the AN may have different effects on brain activity in the HC. The metrics provide a means with which the areas of the AN can be compared to each other in a relatively quick manner.

One metric shown in FIG. 23 is the average amplitude of a bioelectrical brain signal 190 that is indicative of activity in the HC of brain 28 resulting from stimulation delivered to the respective area of the AN. Processor 80 of programmer 14 or a processor of another device (e.g., IMD 16) can determine the average amplitude based on a bioelectrical brain signal sensed for some predetermined period of time immediately following the delivery of stimulation to the AN. In some examples, the predetermined period of time approximately 3 minutes to approximately 5 minutes, although other time ranges can be used. In addition, in some examples, the bioelectrical brain signal of interest can be the bioelectrical brain signal sensed substantially immediately after initiation of the stimulation to the AN of the patient to several minutes after stimulation is delivered to the patient, depending on extent of carryover effect of the stimulation. However, the bioelectrical brain signal of interest can also be sensed at other times, such as some period of time after cessation of stimulation to the AN. It was found that an approximately 10 minute observation window is sufficient to observe the effects of the stimulation to the AN in ovine subjects.

In some examples, the bioelectrical brain signal is sensed in the AN of brain 28, while in other examples, the bioelectrical brain signal is sensed in the HC of brain 28. In addition, in some examples, GUI 170 includes the average amplitudes of the bioelectrical brain signals sensed in both the AN and HC of brain 28. The average amplitude of the bioelectrical brain signal that is indicative of activity in the HC can indicate the activity level within the HC. Thus, this metric can indicate the effect of the stimulation delivered to the respective area of the AN on the activity within the HC of brain 28. In other examples, GUI 170 includes other types of amplitude values instead of or in addition to the average amplitude. Example amplitude values that can be used as metrics for comparing different areas of the AN include, but are not limited to, a peak, peak-to-peak, mean, median or instantaneous amplitude value over a period of time or a maximum amplitude or an amplitude in a particular percentile of the maximum.

Another metric provided by GUI 170 is the power level of the bioelectrical brain signal indicative of activity in the HC of brain 28 at a frequency of about 2 Hertz. As discussed above with respect to FIGS. 19 and 20, it is believed that the power level in the 2 Hz frequency level of the bioelectrical brain signal indicative of activity in the HC of brain 28 may indicate whether there is a meaningful functional connection (e.g., to achieve efficacious stimulation therapy delivery) between the area of the AN to which stimulation was delivered and the HC, at least relative to other areas of the AN. In the ovine subject that was studied (discussed with respect to FIGS. 19 and 20), the power level of the bioelectrical brain signal indicative of activity in the HC of the brain of the ovine subject at a frequency of about 2 Hertz increased when the delivery of stimulation to the AN suppressed activity in the HC. This indicates that the power level in the 2 Hz frequency level may be a useful metric for determining whether stimulation delivery to a particular area of the AN suppresses activity in the HC, and for comparing the effects of stimulation in different areas of the AN.

Processor 80 of programmer 14 can generate GUI based on, for example, brain activity information 76 transmitted to processor 80 by IMD 16. The metrics can be provided by IMD 16 as part of brain activity information 76, or processor 80 can determine the metrics for each area based on a bioelectrical brain signal that is indicative of activity in the HC following delivery of stimulation to the respective area of the AN.

A clinician may review GUI 170 and visually ascertain which area of the AN has the best relative functional connection to the HC for purposes of therapy delivery for managing a seizure disorder. The metrics provided by GUI 170 are concise indicators of the effect of stimulation delivery to the respective area of the AN, which may enable the clinician to relatively quickly compare each area of the AN that was mapped. In some examples, to further aid the clinician's review of the areas of the AN, processor 80 can order the list of areas of the AN 188 in a meaningful way. For example, the areas of the AN 188 can be ordered in ascending or descending order according to the values of one or both metrics 190, 192. In some cases, the clinician can interact with GUI 170 and select the header of one of the metrics columns 190, 192, and in response to receiving the input, processor 80 can order the areas of the AN 188 based on the values of the selected metric.

In some examples, the clinician can select one of the areas of the AN as a target therapy delivery site by highlighting the area of the AN (as shown by the darker box in FIG. 23), and providing input to processor 80 that indicates the area is selected (e.g., depressing a button of user interface 86). In some examples, processor 80 of IMD 16 provides a suggestion to the clinician, such as by automatically highlighting the area of the AN that is associated with the metrics that indicate the best relative functional connection to the HC. Processor 80 may transmit an indication to processor 60 of IMD 16 that indicates the selected area, and, at a later time, such as during trial or chronic therapy delivery, processor 60 can control stimulation generator 64 of IMD 16 (FIG. 3) to generate and deliver stimulation to the selected area of the AN.

In order to translate the selected area of the AN into a usable format for therapy delivery, processor 60 and/or processor 80 can determine which electrodes 24, 26 correspond to the selected area of the AN. Memory 62 of IMD 16 and/or memory 82 of programmer 14 or another device can, for example, associate each area of the AN listed in FIG. 23 with a particular electrode combination (e.g., a subset of electrodes 24, 26 and the polarities of the electrodes). In this way, processor 80, automatically or with the aid of a clinician, may select an electrode combination for therapy delivery to AN of brain 28 based on the metrics indicative of a level of functional connectivity to the HC.

Figure 24:
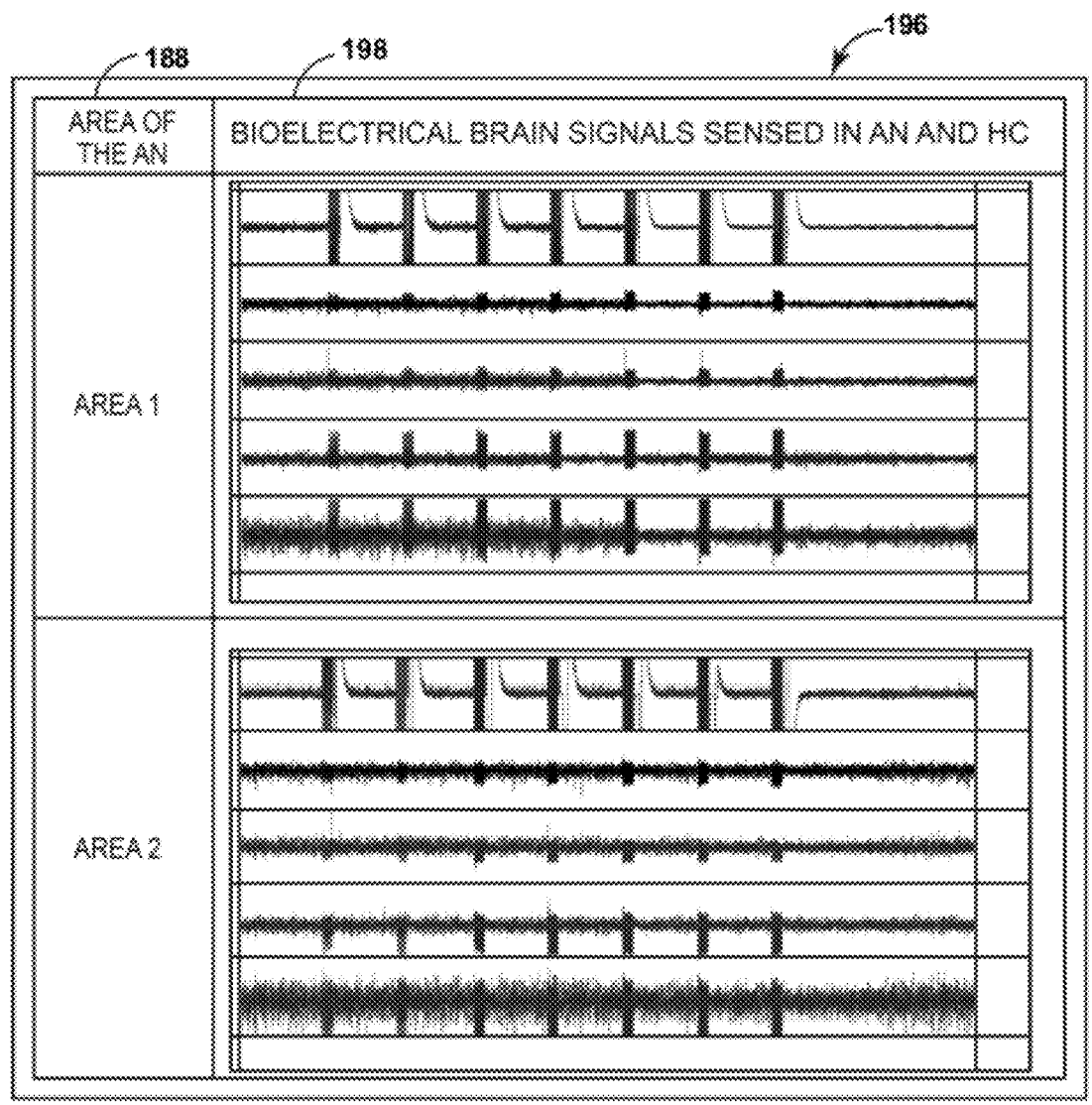

In some examples, rather than illustrating metrics as numerical values listed in a table, GUI 170 can present the metrics in other formats. For example, GUI 170 can include a two-dimensional or three-dimensional graphical representation of the different areas of AN and overlay the relevant HC activity level metric on the graphical representation of the AN, e.g., as numerical values, as color coded indications of the relative level of HC activity suppression, and the like. FIG. 24 is a conceptual illustration of another GUI 196 that can be generated and displayed by programmer 14. GUI 196 includes a list of areas of the AN 188 that have been mapped and bioelectrical brain signals 198 sensed in the AN and HC following the delivery of stimulation to the AN. In FIG. 24, the metric indicative of the functional connectivity between an area of the AN and the HC is the bioelectrical brain signals 198.

Figure 25:
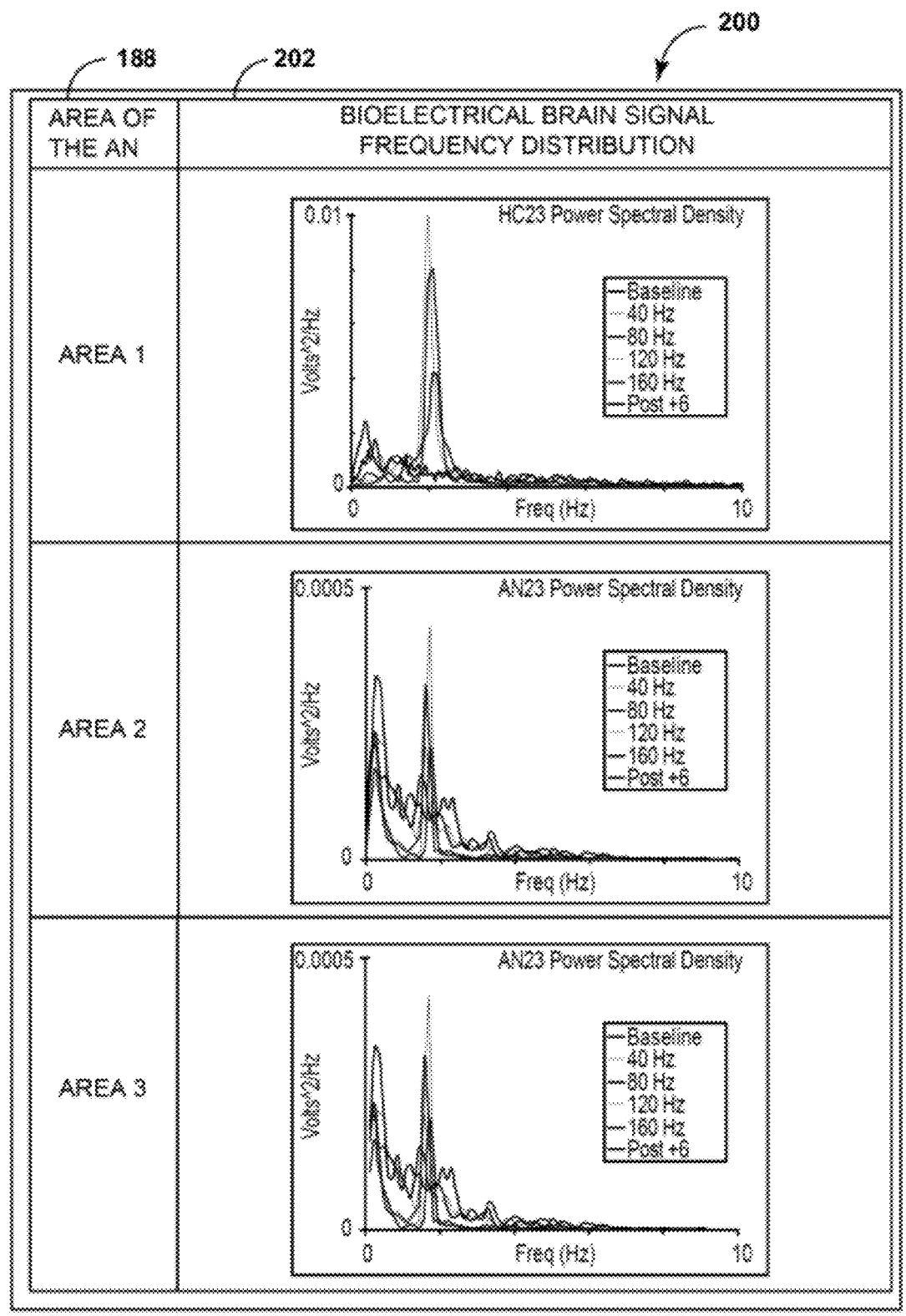

FIG. 25 is a conceptual illustration of another GUI 200 that can be generated and displayed by programmer 14. GUI 200 includes a list of areas of the AN 188 that have been mapped and the frequency distribution 202 of a bioelectrical brain signal sensed in the HC following the delivery of stimulation to the AN. In FIG. 25, the metric indicative of the functional connectivity between an area of the AN and the HC is the frequency distribution 202. In other examples, programmer 14 can generate and display GUIs with a list of areas of the AN and other metrics and/or other combinations of metrics than those described herein.

While devices, systems, and techniques for mapping functions connections of each area of plurality of areas of the AN to the HC are described herein, in other examples, the devices, systems, and techniques can also be used to map each area of a plurality of areas of an AN region to the HC. Example regions with the AN region include the fornix and the mammillothalamic tract (MMT).

In some examples, a method comprises, with a medical device, delivering electrical stimulation to a plurality of different areas of an anterior nucleus of a thalamus of a brain of a patient, wherein the electrical stimulation comprises a frequency greater than or equal to about 80 Hertz, and wherein the electrical stimulation is delivered to each area of the plurality of different areas of the anterior nucleus at a different time; for each area of the plurality of different areas of the anterior nucleus of the thalamus, determining a level of brain activity in a hippocampus of the brain of the patient resulting from the delivery of the electrical stimulation to the area; for each area of the plurality of areas, generating a metric based on the level of brain activity in the hippocampus resulting from the delivery of the electrical stimulation to the area, wherein the metric indicates a relative level of brain activity in the hippocampus resulting from delivery of electrical stimulation to the respective area; and displaying, via a display of a device, indications of each area of the plurality of areas and the respective metric. The metric may, for example, comprise at least one of a characteristic of a bioelectrical brain signal sensed in at least one of the anterior nucleus of the thalamus or the hippocampus of the brain of the patient, a graphical representation of the bioelectrical brain signal, an indication of a distribution of power in the bioelectrical brain signal, a power level of the bioelectrical brain signal at a frequency of about 2 Hertz, or a change in a characteristic of a bioelectrical brain signal relative to a baseline characteristic of the bioelectrical brain signal.

In some examples, a system comprises a stimulation generator that generates and delivers electrical stimulation; a sensing module that senses a bioelectrical brain signal of the patient; and a processor that controls the stimulation generator to deliver electrical stimulation to each area of a plurality of different areas of an anterior nucleus of a thalamus of a brain of a patient at a different time, wherein the electrical stimulation comprises a frequency greater than or equal to about 80 Hertz, and wherein the processor determines, for each area of the plurality of different areas of the anterior nucleus of the thalamus, a level of brain activity in a hippocampus of the brain of the patient resulting from the delivery of the electrical stimulation to the area based on the bioelectrical brain signal, generates a metric based on the level of brain activity in the hippocampus resulting from the delivery of the electrical stimulation to the area, wherein the metric indicates a relative level of brain activity in the hippocampus resulting from delivery of electrical stimulation to the respective area. The system may, in some examples, further comprise a display, the processor displays, via the display, indications of each area of the plurality of areas and the respective metric. The metric may be, for example, any of the metrics described above.

In some examples, a system comprises means for delivering electrical stimulation to a brain of a patient; means for controlling the means for delivering electrical stimulation to deliver electrical stimulation to each area of a plurality of different areas of an anterior nucleus of a thalamus of the brain at a different time, wherein the electrical stimulation comprises a frequency greater than or equal to about 80 Hertz; means for determining, for each area of the plurality of different areas of the anterior nucleus of the thalamus, a level of brain activity in a hippocampus of the brain of the patient resulting from the delivery of the electrical stimulation to the area; and generating a metric for each area of the plurality of areas, based on the level of brain activity in the hippocampus resulting from the delivery of the electrical stimulation to the area, wherein the metric indicates a relative level of brain activity in the hippocampus resulting from delivery of electrical stimulation to the respective area.

In addition, in some examples, a computer readable medium comprises instructions that, when executed by a processor, cause the processor to control a stimulation generator to deliver electrical stimulation to a plurality of different areas of an anterior nucleus of a thalamus of a brain of a patient, wherein the electrical stimulation comprises a frequency greater than or equal to about 80 Hertz, and wherein the electrical stimulation is delivered to each area of the plurality of different areas of the anterior nucleus at a different time; for each area of the plurality of different areas of the anterior nucleus of the thalamus, determine a level of brain activity in a hippocampus of the brain of the patient resulting from the delivery of the electrical stimulation to the area; and for each area of the plurality of areas, generate a metric based on the level of brain activity in the hippocampus resulting from the delivery of the electrical stimulation to the area, wherein the metric indicates a relative level of brain activity in the hippocampus resulting from delivery of electrical stimulation to the respective area.

The techniques described in this disclosure, including those attributed to programmer 14, IMD 16, or various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. While the techniques described herein are primarily described as being performed by processor 60 of IMD 16 and/or processor 80 of programmer 14, any one or more parts of the techniques described herein may be implemented by a processor of one of IMD 16, programmer 14, or another computing device, alone or in combination with each other.

In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed to support one or more aspects of the functionality described in this disclosure.

Various examples have been described. These and other examples are within the scope of the following claims.

What is claimed is:

1. A method comprising:
controlling a medical device to deliver electrical stimulation to a plurality of different areas of an anterior nucleus of a thalamus of a brain of a patient, wherein the electrical stimulation comprises a frequency greater than or equal to about 80 Hertz, and wherein the electrical stimulation is delivered to each area of the plurality of different areas of the anterior nucleus at different times;
for each area of the plurality of different areas of the anterior nucleus of the thalamus, determining a level of brain activity in a hippocampus of the brain of the patient resulting from the delivery of the electrical stimulation to the area; and
with a processor, selecting at least one of the areas of the plurality of different areas of the anterior nucleus of the thalamus of the brain of the patient as a target therapy delivery site based on the associated level of brain activity in the hippocampus of the brain.

2. The method of claim 1, further comprising sensing a bioelectrical brain signal in the hippocampus of the brain of the patient, wherein determining, for each area of the plurality of different areas of the anterior nucleus of the thalamus, the level of brain activity in the hippocampus of the brain of the patient resulting from the delivery of the electrical stimulation to the area comprises determining the level of brain activity in the hippocampus of the brain of the patient based on the sensed bioelectrical brain signal.

3. The method of claim 1, further comprising sensing a bioelectrical brain signal in the anterior nucleus of the thalamus of the brain of the patient, wherein determining, for each area of the plurality of different areas of the anterior nucleus of the thalamus, the level of brain activity in the hippocampus of the brain of the patient resulting from the delivery of the electrical stimulation to the area comprises determining the level of brain activity in the hippocampus of the brain of the patient based on the sensed bioelectrical brain signal.

4. The method of claim 1, wherein controlling the medical device to deliver electrical stimulation to the plurality of different areas of the anterior nucleus of the thalamus of the brain of the patient comprises controlling the medical device to deliver stimulation to a first area of the anterior nucleus via a subset of electrodes of a lead, and wherein determining the level of brain activity in the hippocampus of the brain of the patient resulting from the delivery of the electrical stimulation to the area comprises determining, with the medical device, a first level of brain activity in the hippocampus of the brain of the patient resulting from the delivery of the electrical stimulation to the first area, the method further comprising:
receiving an indication that the lead has been moved within the brain of the patient;
after receiving the indication, controlling the medical device to deliver stimulation to a second area of the anterior nucleus via the subset of electrodes, wherein the plurality of different areas comprises the second area; and
after the medical device delivers stimulation to the second area of the anterior nucleus, determining a second level of brain activity in the hippocampus of the brain of the patient resulting from the delivery of the electrical stimulation to the second area of the anterior nucleus.

5. The method of claim 4, further comprising:
determining whether the second level of brain activity in the hippocampus of the brain of the patient is less than the first level of brain activity in the hippocampus;
wherein if the second level is less than the first level, controlling the medical device to deliver stimulation to a third area of the anterior nucleus via the subset of electrodes, wherein the plurality of different areas comprises the third area, and after the medical device delivers stimulation to the third area of the anterior nucleus, determining a third level of brain activity in the hippocampus of the brain of the patient resulting from the delivery of the electrical stimulation to the third area of the anterior nucleus; and
wherein if the second level is not less than the first level, selecting the first area of the anterior nucleus of the thalamus of the brain of the patient as the target therapy delivery site.

6. The method of claim 1, wherein the plurality of different areas of the anterior nucleus comprises a first area and a second area, wherein controlling the medical device to deliver electrical stimulation to the plurality of different areas of the anterior nucleus of the thalamus of the brain of the patient and, for each area of the plurality of different areas of the anterior nucleus, determining the level of brain activity in the hippocampus of the brain of the patient resulting from the delivery of the electrical stimulation to the area comprises:
controlling the medical device to deliver electrical stimulation to the first area of the anterior nucleus of the thalamus of the brain of the patient, wherein the electrical stimulation comprises a frequency greater than or equal to about 80 Hertz;
immediately after the medical device delivers electrical stimulation to the first area of the anterior nucleus, determining a first level of brain activity in the hippocampus of the brain of the patient;
controlling the medical device to deliver electrical stimulation to the second area of the anterior nucleus of the thalamus of the brain, wherein the electrical stimulation comprises a frequency greater than or equal to about 80 Hertz; and
immediately after the medical device delivers electrical stimulation to the second area of the anterior nucleus, determining a second level of brain activity in the hippocampus of the brain of the patient,
wherein selecting at least one of the areas of the anterior nucleus of the thalamus of the brain of the patient as the target therapy delivery site comprises, with the processor, selecting one of the first area or the second area of the anterior nucleus of the thalamus of the brain of the patient as the target therapy delivery site based on the first and second levels of brain activity in the hippocampus of the brain.

7. The method of claim 6, further comprising:
implanting an implantable medical lead at a first location in the brain of the patient, wherein controlling the medical device to deliver electrical stimulation to the first area of the anterior nucleus of the thalamus of the brain of the patient comprises controlling the medical device to deliver the electrical stimulation via electrodes of the implantable medical lead while the implantable medical lead is at the first location; and moving the implantable medical lead to a second location in the brain of the patient, wherein controlling the medical device to deliver electrical stimulation to the second area of the anterior nucleus of the thalamus of the brain of the patient comprises controlling the medical device to deliver electrical stimulation via the electrodes of the implantable medical lead while the implantable medical lead is at the second location.

8. The method of claim 1, wherein selecting at least one of the areas of the plurality of different areas of the anterior nucleus of the thalamus of the brain of the patient as a target therapy delivery site based on the associated level of brain activity in the hippocampus of the brain comprises selecting the area of the plurality of different areas associated with a lowest level of brain activity in the hippocampus.

9. The method of claim 1, further comprising implanting an implantable medical lead comprising a plurality of electrodes in the anterior nucleus of the thalamus of the brain of the patient, wherein controlling the medical device to deliver electrical stimulation to the plurality of different areas of the anterior nucleus comprises, for each area of the plurality of different areas, controlling the medical device to deliver stimulation to the anterior nucleus using a different subset of electrodes of the lead.

10. The method of claim 1, further comprising associating the level of brain activity in the hippocampus with the respective area of the anterior nucleus and storing the level of brain activity in the hippocampus and associated area of the anterior nucleus in a memory of a device.

11. The method of claim 1, wherein the level of brain activity comprises at least one of a time domain characteristic or a frequency domain characteristic of a bioelectrical brain signal sensed in at least one of the anterior nucleus of the thalamus or the hippocampus of the brain of the patient.

12. The method of claim 11, wherein the level of brain activity comprises an amplitude of the bioelectrical brain signal sensed in the at least one of the anterior nucleus of the thalamus or the hippocampus of the brain of the patient.

13. The method of claim 11, wherein the level of brain activity comprises a power level of the bioelectrical brain signal at a frequency of about 2 Hertz.

14. The method of claim 1, wherein the level of brain activity comprises at least one of a change in a characteristic of a bioelectrical brain signal sensed in at least one of the anterior nucleus of the thalamus or the hippocampus of the brain of the patient relative to a baseline characteristic of the bioelectrical brain signal.

15. The method of claim 1, wherein determining the level of brain activity in the hippocampus of the brain of the patient resulting from the delivery of the electrical stimulation to the area of the plurality of different areas of the anterior nucleus of the thalamus comprises determining the level of brain activity in the hippocampus of the brain while electrical stimulation is being delivered to the area.

16. The method of claim 1, wherein determining the level of brain activity in the hippocampus of the brain of the patient resulting from the delivery of the electrical stimulation to the area of the plurality of different areas of the anterior nucleus of the thalamus comprises determining the level of brain activity in the hippocampus of the brain after terminating the delivery of electrical stimulation to the area.

17. The method of claim 1, further comprising:
for each area of the plurality of areas, generating a metric based on the level of brain activity in the hippocampus resulting from the delivery of the electrical stimulation to the area, wherein the metric indicates a relative level of brain activity in the hippocampus resulting from delivery of electrical stimulation to the respective area of the anterior nucleus; and
displaying, via a display of a device, indications of each area of the plurality of areas and the respective metric.

18. The method of claim 17, wherein the metric comprises at least one of a characteristic of a bioelectrical brain signal sensed in at least one of the anterior nucleus of the thalamus or the hippocampus of the brain of the patient, a graphical representation of the bioelectrical brain signal, an indication of a distribution of power in the bioelectrical brain signal, a power level of the bioelectrical brain signal at a frequency of about 2 Hertz, or a change in a characteristic of a bioelectrical brain signal relative to a baseline characteristic of the bioelectrical brain signal.

19. The method of claim 1, further comprising controlling the medical device to deliver electrical stimulation therapy to the target therapy delivery site.

20. The method of claim 1, wherein controlling the medical device to deliver electrical stimulation to the plurality of different areas of the anterior nucleus comprises controlling the medical device to deliver electrical stimulation via each electrode combination of a plurality of electrode combinations, and wherein selecting at least one of the areas of the plurality of different areas of the anterior nucleus as the target therapy delivery site based on the associated level of brain activity in the hippocampus of the brain comprises selecting at least one electrode combination of the plurality of electrode combinations based on the associated level of brain activity in the hippocampus of the brain.

21. A system comprising:
a stimulation generator configured to generate and deliver electrical stimulation;
a sensing module configured to sense a bioelectrical brain signal of the patient; and
a processor configured to control the stimulation generator to deliver electrical stimulation to each area of a plurality of different areas of an anterior nucleus of a thalamus of a brain of a patient at a different time, wherein the electrical stimulation comprises a frequency greater than or equal to about 80 Hertz, and determine, for each area of the plurality of different areas of the anterior nucleus of the thalamus, a level of brain activity in a hippocampus of the brain of the patient resulting from the delivery of the electrical stimulation to the area based on the bioelectrical brain signal, and select at least one of the areas of the anterior nucleus of the thalamus of the brain of the patient as a target therapy delivery site based on the associated level of brain activity in the hippocampus of the brain.

22. The system of claim 21, wherein the sensing module is configured to sense the bioelectrical brain signal in the hippocampus of the brain of the patient and the processor is configured to determine, for each area of the plurality of different areas of the anterior nucleus of the thalamus, the level of brain activity in the hippocampus of the brain of the patient resulting from the delivery of the electrical stimulation to the area based on the bioelectrical brain signal sensed in the hippocampus of the brain.

23. The system of claim 21, wherein the sensing module is configured to sense the bioelectrical brain signal in the anterior nucleus of the thalamus of the brain of the patient and the processor is configured to determine, for each area of the plurality of different areas of the anterior nucleus of the thalamus, the level of brain activity in the hippocampus of the brain of the patient resulting from the delivery of the electrical stimulation to the area based on the bioelectrical brain signal sensed in the anterior nucleus of the thalamus of the brain.

24. The system of claim 21, further comprising a lead comprising electrodes, wherein the processor is configured to control the stimulation generator to deliver stimulation to a first area of the anterior nucleus via a subset of the electrodes of the lead, and determine the level of brain activity in the hippocampus of the brain of the patient resulting from the delivery of the electrical stimulation to the area by at least determining a first level of brain activity in the hippocampus of the brain of the patient resulting from the delivery of the electrical stimulation to the first area, wherein the processor is further configured to receive an indication that the lead has been moved within the brain of the patient and, after receiving the indication, control the stimulation generator to deliver stimulation to a second area of the anterior nucleus via the subset of electrodes, wherein the plurality of different areas comprises the second area, and, determine a second level of brain activity in the hippocampus of the brain of the patient resulting from the delivery of the electrical stimulation to the second area of the anterior nucleus.

25. The system of claim 24, wherein the processor is configured to determine whether the second level of brain activity in the hippocampus of the brain of the patient is less than the first level of brain activity in the hippocampus, and, in response to determining the second level is less than the first level, control the stimulation generator to deliver stimulation to a third area of the anterior nucleus via the subset of electrodes, wherein the plurality of different areas comprises the third area, and determine a third level of brain activity in the hippocampus of the brain of the patient resulting from the delivery of the electrical stimulation to the third area of the anterior nucleus, and wherein the processor is configured to, in response to determining the second level is not less than the first level, select the first area of the anterior nucleus of the thalamus of the brain of the patient as the target therapy delivery site.

26. The system of claim 21, wherein the plurality of different areas of the anterior nucleus comprises a first area and a second area, wherein the processor is configured to control the stimulation generator to deliver electrical stimulation to the plurality of different areas of the anterior nucleus of the thalamus of the brain of the patient and, for each area of the plurality of different areas of the anterior nucleus, determine the level of brain activity in the hippocampus of the brain of the patient resulting from the delivery of the electrical stimulation to the area by at least:
controlling the stimulation generator to deliver electrical stimulation to the first area of the anterior nucleus of the thalamus of the brain of the patient, wherein the electrical stimulation comprises a frequency greater than or equal to about 80 Hertz;
immediately after the stimulation generator delivers the electrical stimulation to the first area of the anterior nucleus, determining a first level of brain activity in the hippocampus of the brain of the patient;
after determining the first level of brain activity in the hippocampus of the brain, controlling the stimulation generator to deliver stimulation to the second area of the anterior nucleus of the thalamus of the brain, wherein the electrical stimulation comprises a frequency greater than or equal to about 80 Hertz; and
immediately after the stimulation generator delivers electrical stimulation to the second area of the anterior nucleus, determining a second level of brain activity in the hippocampus of the brain of the patient,
wherein the processor is configured to select one of the first area or the second area of the anterior nucleus of the thalamus of the brain of the patient as the target therapy delivery site based on the first and second levels of brain activity in the hippocampus of the brain.

27. The system of claim 26, further comprising a lead, wherein the processor is configured to control the stimulation generator to deliver electrical stimulation to the first area of the anterior nucleus of the thalamus of the brain of the patient when the lead is implanted at a first location in the brain of the patient and control the stimulation generator to deliver electrical stimulation to the second area of the anterior nucleus of the thalamus of the brain of the patient when the lead is implanted at a second location in the brain of the patient, wherein the first and second locations are different.

28. The system of claim 21, further comprising a lead comprising a plurality of electrodes, wherein the stimulation generator is configured to deliver electrical stimulation to at least two different areas of the plurality of different areas of the anterior nucleus via a different subset of electrodes of the lead.

29. The system of claim 21, further comprising a memory, wherein the processor is configured to associate the level of brain activity in the hippocampus with the respective area of the anterior nucleus and stores the level of brain activity in the hippocampus and associated area of the anterior nucleus in the memory.

30. The system of claim 21, wherein the level of brain activity comprises at least one of time domain characteristic or a frequency domain characteristic of a bioelectrical brain signal sensed in at least one of the anterior nucleus of the thalamus or the hippocampus of the brain of the patient.

31. The system of claim 30, wherein the level of brain activity comprises an amplitude of the bioelectrical brain signal sensed in the at least one of the anterior nucleus of the thalamus or the hippocampus of the brain of the patient.

32. The system of claim 30, wherein the level of brain activity comprises a power level of the bioelectrical brain signal at a frequency of about 2 Hertz.

33. The system of claim 21, wherein the level of brain activity comprises at least one of a change in a characteristic of a bioelectrical brain signal sensed in at least one of the anterior nucleus of the thalamus or the hippocampus of the brain of the patient relative to a baseline characteristic of the bioelectrical brain signal.

34. The system of claim 21, further comprising a display, wherein the processor is configured to, for each area of the plurality of areas, generate a metric based on the level of brain activity in the hippocampus resulting from the delivery of the electrical stimulation to the area, wherein the metric indicates a relative level of brain activity in the hippocampus resulting from delivery of electrical stimulation to the respective area, and present, via the display, indications of each area of the plurality of areas and the respective metric.

35. The system of claim 34, wherein the metric comprises at least one of a characteristic of a bioelectrical brain signal sensed in at least one of the anterior nucleus of the thalamus or the hippocampus of the brain of the patient, a graphical representation of the bioelectrical brain signal, an indication of a distribution of power in the bioelectrical brain signal, a power level of the bioelectrical brain signal at a frequency of about 2 Hertz, or a change in a characteristic of a bioelectrical brain signal relative to a baseline characteristic of the bioelectrical brain signal.

36. The system of claim 21, further comprising a medical device programmer comprising the processor.

37. The system of claim 21, wherein the processor is configured to control the stimulation generator to generate and deliver electrical stimulation therapy to the target therapy delivery site.

38. The system of claim 21, wherein the processor is configured to determine, for each area of the plurality of different areas of the anterior nucleus, the level of brain activity in the hippocampus of the brain of the patient resulting from the delivery of the electrical stimulation to the area based on the bioelectrical brain signal while the stimulation generator is delivering the electrical stimulation to the area.

39. The system of claim 21, wherein the processor is configured to determine, for each area of the plurality of different areas of the anterior nucleus, the level of brain activity in the hippocampus of the brain of the patient resulting from the delivery of the electrical stimulation to the area based on the bioelectrical brain signal after the stimulation generator terminates delivery of the electrical stimulation to the area.

40. The system of claim 21, further comprising a plurality of electrodes, wherein the processor is configured to control the stimulation generator to deliver electrical stimulation to the plurality of different areas of the anterior nucleus of the thalamus by at least controlling the stimulation generator to deliver electrical stimulation to the anterior nucleus via each of a plurality of combinations of electrodes of the plurality of electrodes, and wherein the processor is configured to select at least one of the areas of the plurality of different areas of the anterior nucleus as the target therapy delivery site based on the associated level of brain activity in the hippocampus of the brain by at least selecting at least one electrode combination of the plurality of electrode combinations based on the associated level of brain activity in the hippocampus of the brain.

41. The system of claim 21, wherein the processor is configured to select at least one of the areas of the plurality of different areas of the anterior nucleus of the thalamus of the brain of the patient as the target therapy delivery site based on the associated level of brain activity in the hippocampus of the brain by at least selecting the area of the plurality of different areas associated with a lowest level of brain activity in the hippocampus.

42. A system comprising:
   means for delivering electrical stimulation to a brain of a patient;
   means for controlling the means for delivering electrical stimulation to deliver electrical stimulation to each area of a plurality of different areas of an anterior nucleus of a thalamus of the brain at a different time, wherein the electrical stimulation comprises a frequency greater than or equal to about 80 Hertz;
   means for determining, for each area of the plurality of different areas of the anterior nucleus of the thalamus, a level of brain activity in a hippocampus of the brain of the patient resulting from the delivery of the electrical stimulation to the area; and
   means for selecting at least one of the areas of the anterior nucleus of the thalamus of the brain of the patient as a target therapy delivery site based on the associated level of brain activity in the hippocampus of the brain.

43. The system of claim 42, further comprising means for sensing a bioelectrical brain signal of the brain of the patient, wherein the means for determining, for each area of the plurality of different areas of the anterior nucleus of the thalamus, the level of brain activity in the hippocampus of the brain of the patient resulting from the delivery of the electrical stimulation to the area is configured to determine the level of brain activity in the hippocampus based on the sensed bioelectrical brain signal.

44. The system of claim 42, further comprising a lead comprising electrodes, wherein the means for delivering electrical stimulation is configured to deliver electrical stimulation to the plurality of different areas by at least delivering stimulation to a first area of the anterior nucleus via a subset of electrodes of the lead, and wherein the means for determining the level of brain activity in the hippocampus of the brain of the patient resulting from the delivery of the electrical stimulation to the area is configured to determine a first level of brain activity in the hippocampus of the brain of the patient resulting from the delivery of the electrical stimulation to the first area, the system further comprising:
   means for receiving an indication that the lead has been moved within the brain of the patient, wherein the means for delivering electrical stimulation is configured to, after the indication is received by the means for receiving the indication, deliver stimulation to a second area of the anterior nucleus via the subset of electrodes, wherein the plurality of different areas comprises the second area, and the means for determining the level of brain activity in the hippocampus of the brain is configured to determine a second level of brain activity in the hippocampus of the brain of the patient resulting from the delivery of the electrical stimulation to the second area of the anterior nucleus; and
   means for determining whether the second level of brain activity in the hippocampus of the brain of the patient is less than the first level of brain activity in the hippocampus,
   wherein in response to determining the second level is less than the first level, the means for delivering electrical stimulation is configured to deliver electrical stimulation to a third area of the anterior nucleus via the subset of electrodes, wherein the plurality of different areas comprises the third area, and the means for determining the level of brain activity in the hippocampus of the brain is configured to determine a third level of brain activity in the hippocampus of the brain resulting from the delivery of the electrical stimulation to the third area of the anterior nucleus, and
   wherein in response to determining the second level is not less than the first level, the means for selecting at least one of the areas of the anterior nucleus of the thalamus of the brain of the patient as the target therapy delivery site is configured to select the first area of the anterior nucleus of the thalamus of the brain of the patient as the target therapy delivery site.

45. The system of claim 42, further comprising:
   means for generating a metric for each area of the plurality of areas based on the level of brain activity in the hippocampus resulting from the delivery of the electrical stimulation to the area, wherein the metric indicates a relative level of brain activity in the hippocampus resulting from delivery of electrical stimulation to the respective area; and
   means for displaying indications of each area of the plurality of areas and the respective metric.

46. The system of claim 45, wherein the metric comprises at least one of a characteristic of a bioelectrical brain signal sensed in at least one of the anterior nucleus of the thalamus or the hippocampus of the brain of the patient, a graphical representation of the bioelectrical brain signal, an indication of a distribution of power in the bioelectrical brain signal, a power level of the bioelectrical brain signal at a frequency of about 2 Hertz, or a change in a characteristic of a bioelectrical brain signal relative to a baseline characteristic of the bioelectrical brain signal.

47. The system of claim 42, wherein the means for selecting the at least one of the areas of the anterior nucleus of the thalamus as the target therapy delivery site based on the associated level of brain activity in the hippocampus of the brain is configured to select least one of the areas of the anterior nucleus by at least selecting an electrode combination.

48. A non-transitory computer readable medium comprises instructions that, when executed by a processor, cause the processor to:
- control a stimulation generator to deliver electrical stimulation to a plurality of different areas of an anterior nucleus of a thalamus of a brain of a patient, wherein the electrical stimulation comprises a frequency greater than or equal to about 80 Hertz, and wherein the electrical stimulation is delivered to each area of the plurality of different areas of the anterior nucleus at a different time;
- for each area of the plurality of different areas of the anterior nucleus of the thalamus, determine a level of brain activity in a hippocampus of the brain of the patient resulting from the delivery of the electrical stimulation to the area; and
- select at least one of the areas of the anterior nucleus of the thalamus of the brain of the patient as a target therapy delivery site based on the associated level of brain activity in the hippocampus of the brain.

* * * * *